United States Patent
Choi et al.

(10) Patent No.: US 10,050,208 B2
(45) Date of Patent: Aug. 14, 2018

(54) COMPOUND, AND LIGHT-EMITTING ELEMENT AND ELECTRONIC DEVICE COMPRISING SAME

(71) Applicant: LMS Co., Ltd, Pyeongtaek-si (KR)

(72) Inventors: Jeong Og Choi, Seoul (KR); Joon Ho Jung, Hwaseong-si (KR); Oh Kwan Kwon, Anyang-si (KR)

(73) Assignee: LMS CO., LTD., Pyeongtaek-si (KR)

( * ) Notice: Subject to any disclaimer, the term of this patent is extended or adjusted under 35 U.S.C. 154(b) by 347 days.

(21) Appl. No.: 14/647,582

(22) PCT Filed: Nov. 28, 2013

(86) PCT No.: PCT/KR2013/010886
§ 371 (c)(1),
(2) Date: Sep. 21, 2015

(87) PCT Pub. No.: WO2014/084619
PCT Pub. Date: Jun. 5, 2014

(65) Prior Publication Data
US 2016/0248019 A1    Aug. 25, 2016

(30) Foreign Application Priority Data
Nov. 28, 2012   (KR) .......................... 10-2012-0136377

(51) Int. Cl.
*H01L 51/00* (2006.01)
*C07D 487/14* (2006.01)
(Continued)

(52) U.S. Cl.
CPC ........ *H01L 51/0061* (2013.01); *C07D 455/03* (2013.01); *C07D 455/04* (2013.01); *C07D 471/06* (2013.01); *C07D 487/14* (2013.01); *H01L 51/006* (2013.01); *H01L 51/0059* (2013.01); *H01L 51/0072* (2013.01); *H01L 51/0073* (2013.01); *H01L 51/0074* (2013.01); *H01L 51/0094* (2013.01); *H01L 51/0052* (2013.01); *H01L 51/0071* (2013.01); *H01L 51/0081* (2013.01); *H01L 51/0085* (2013.01); *H01L 51/506* (2013.01); *H01L 51/5016* (2013.01); *H01L 51/5056* (2013.01);
(Continued)

(58) Field of Classification Search
CPC combination set(s) only.
See application file for complete search history.

(56) References Cited

U.S. PATENT DOCUMENTS

2012/0319052 A1   12/2012   Brocke et al.

FOREIGN PATENT DOCUMENTS

KR   1020100006072 A   1/2010
KR   1020100048447 A   5/2010
(Continued)

*Primary Examiner* — Jennifer A Chriss
*Assistant Examiner* — Sean M Deguire
(74) *Attorney, Agent, or Firm* — Polsinelli PC

(57) ABSTRACT

The present invention suggest a novel compound for improving the capability of injecting and/or transporting a hole in a light-emitting element, and a light-emitting element and an electronic device including the same, and may improve the light-emitting efficiency of the light-emitting element, and increase the lifespan thereof. In addition, the present invention may improve thermal stability (heat resistance) of the light-emitting element.

9 Claims, 2 Drawing Sheets

(51) Int. Cl.
*C07D 471/06* (2006.01)
*C07D 455/03* (2006.01)
*C07D 455/04* (2006.01)
*H01L 51/50* (2006.01)

(52) U.S. Cl.
CPC ...... *H01L 51/5064* (2013.01); *H01L 51/5088* (2013.01); *H01L 51/5096* (2013.01); *H01L 2251/308* (2013.01); *H01L 2251/5361* (2013.01)

(56) References Cited

FOREIGN PATENT DOCUMENTS

| KR | 1020110106192 A | 9/2011 | | |
|---|---|---|---|---|
| WO | WO 2010050778 A1 * | 5/2010 | ............. | C09K 11/06 |
| WO | 2011107186 A2 | 9/2011 | | |

* cited by examiner

[Fig.1]
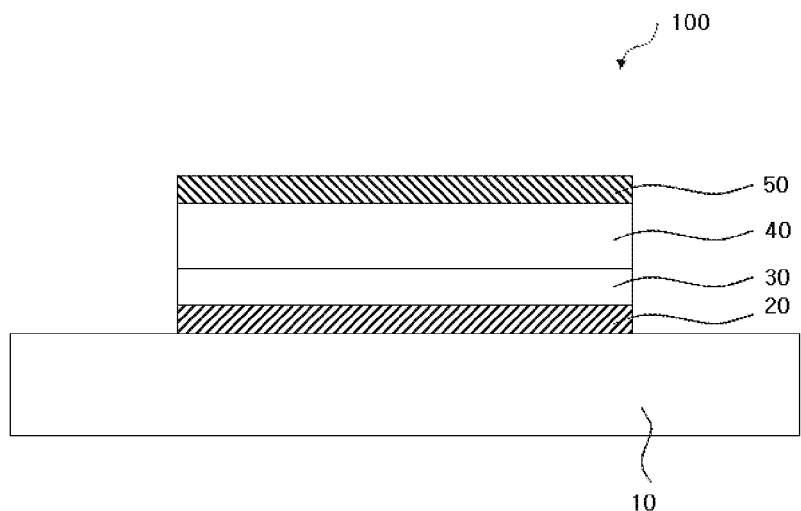
[Fig.2]
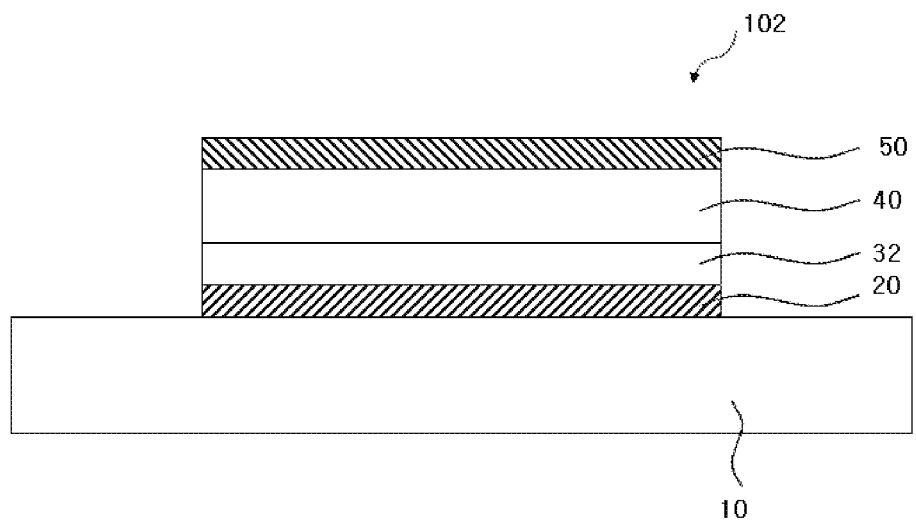

[Fig.3]
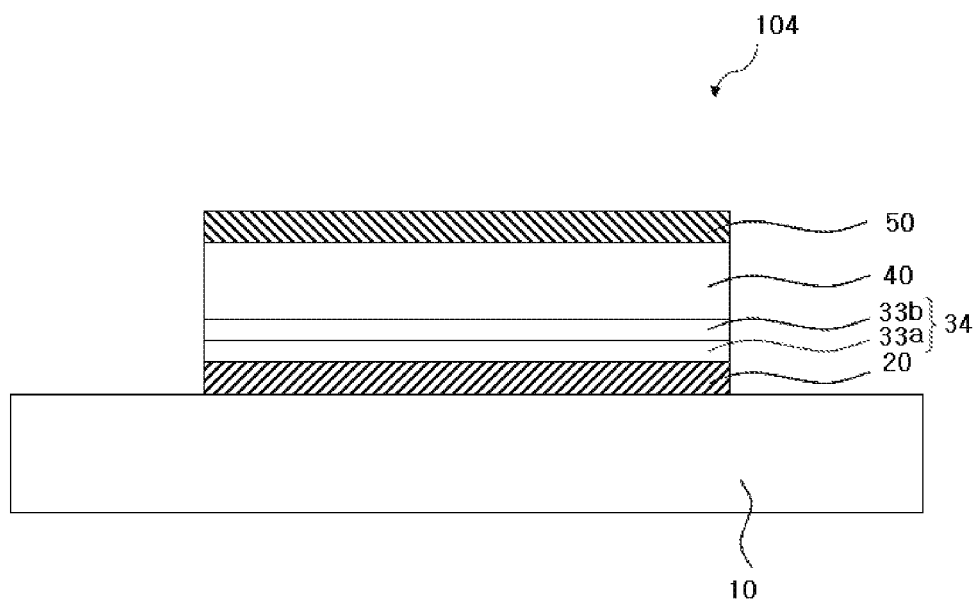

COMPOUND, AND LIGHT-EMITTING ELEMENT AND ELECTRONIC DEVICE COMPRISING SAME

CROSS-REFERENCE TO RELATED APPLICATIONS

This application is the United States national phase of International Application No. PCT/KR2013/010886 filed Nov. 28, 2013, and claims priority to Korean Patent Application No. 10-2012-0136377 filed Nov. 28, 2012, the disclosures of which are hereby incorporated in their entirety by reference.

BACKGROUND

Field of the Invention

The present invention relates to a novel compound, and a light-emitting element and an electronic device including the same, and more particularly, to a compound for an electroluminescence element, and a light-emitting element and an electronic device including the same.

Background Art

In general, a light-emitting diode includes two electrodes facing each other and a light-emitting layer including a light-emitting compound interposed between the electrodes. When current flows between the electrodes, the light-emitting compound produces light. A display device using the light-emitting element does not need a separate light source device, and thus may decrease the weight, size or thickness of the display device. Further, the display device using the light-emitting element has advantages in that the viewing angle, the contrast ratio, the color reproducibility, and the like are excellent and power consumption is low as compared to a display device using a backlight and a liquid crystal.

The light-emitting element may further include a hole transporting layer disposed between an anode and a light-emitting layer. The hole transporting layer may stabilize the interface between the anode and the light-emitting layer, and minimize an energy barrier between the anode and the light-emitting layer.

However, the light-emitting element still has problems in that the lifespan for light emission is short, the power efficiency is low, and thermal stability (heat resistance) is low. In order to solve these problems, various compounds have been developed as a material for the light-emitting element, but there is a limitation in manufacturing a light-emitting element which satisfies all in respect to the lifespan of light emission, power efficiency, and thermal stability.

SUMMARY OF THE INVENTION

Technical Problem

Thus, a technical problem of the present invention has been contrived in view of these circumstances, and an object of the present invention is to provide a novel compound for improving the capability of injecting and transporting a hole in a light-emitting element.

Another object of the present invention is to provide a light-emitting element including the compound.

Still another object of the present invention is to provide an electronic device including the light-emitting element.

Technical Solution

A compound according to an exemplary embodiment for realizing the aforementioned object of the present invention is represented by the following Formula 1.

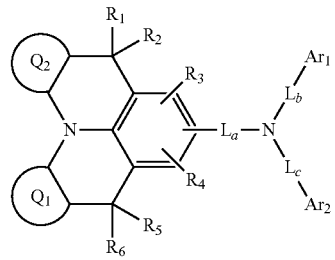
[Formula 1]

in Formula 1, $L_a$, $L_b$, and $L_c$ each independently represent *-$L_1$-$L_2$-$L_3$-$L_4$-*, $L_1$, $L_2$, $L_3$, and $L_4$ each independently represent a single bond, —O—, —S—, an arylene group having 6 to 60 carbon atoms, a heteroarylene group having 2 to 60 carbon atoms, an alkenylene group having 2 to 60 carbon atoms, a cycloalkylene group having 3 to 60 carbon atoms, or a heterocycloalkylene group having 2 to 60 carbon atoms, $Ar_1$ and $Ar_2$ each independently represent *-$A_1$-$A_2$-$A_3$-$A_4$, $A_1$, $A_2$, and $A_3$ each independently represent a single bond, —O—, —S—, a linear or branched alkylene group (—$(CH_2)_j$—, here, j is an integer of 1 to 60) having 1 to 60 carbon atoms, an arylene group having 6 to 60 carbon atoms, a heteroarylene group having 2 to 60 carbon atoms, a cycloalkylene group having 3 to 60 carbon atoms, a heterocycloalkylene group 2 to 60 carbon atoms, an adamantylene group, a bicycloalkylene group having 7 to 60 carbon atoms, or an alkenylene group having 2 to 60 carbon atoms, $A_4$ represents hydrogen, an alkyl group having 1 to 60 carbon atoms, an aryl group having 6 to 60 carbon atoms, a heteroaryl group having 2 to 60 carbon atoms, a cycloalkyl group having 3 to 60 carbon atoms, a heterocycloalkyl group having 2 to 60 carbon atoms, an adamantyl group, a bicycloalkyl group having 7 to 60 carbon atoms, the following Formula 2 or the following Formula 3;

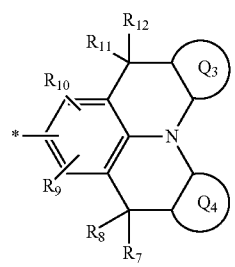
[Formula 2]

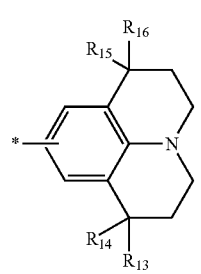
[Formula 3]

$Q_1$, $Q_2$, $Q_3$, and $Q_4$ each independently represent an aryl group having 6 to 60 carbon atoms or a heteroaryl group having 2 to 60 carbon atoms, which is unsubstituted or substituted with one or more selected from the group consisting of an alkyl group having 1 to 12 carbon atoms, an alkoxy group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, or an alkenyl group having 2 to 12 carbon atoms, and $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each independently represent hydrogen, an alkyl group having 1 to 6 carbon atoms, an alkoxy group having 1 to 6 carbon atoms, an aryl group having 6 to 20 carbon atoms, or a heteroaryl group having 2 to 20 carbon atoms.

In this case, one or more hydrogen atoms of $Q_1$, $Q_2$, $L_a$, $L_b$, $L_c$, $Ar_1$, and $Ar_2$ of Formula 1 are each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

A light-emitting element according to an exemplary embodiment for realizing the aforementioned another object of the present invention includes a first electrode, a second electrode, a light-emitting layer, and a hole transporting layer including the compound represented by Formula 1. The first electrode and the second electrode face each other, and the light-emitting layer is interposed between the first and second electrodes. The hole transporting layer is disposed between the first electrode and the light-emitting layer.

In an exemplary embodiment, the hole transporting layer may further include a P-type dopant.

In an exemplary embodiment, the hole transporting layer may include a first layer including the compound and the P-type dopant, and a second layer including the compound. The first layer is disposed between the first electrode and the light-emitting layer, and the second layer may be disposed between the first layer and the light-emitting layer. In this case, the second layer may further include a dopant which is substantially the same as or different from the P-type dopant of the first layer.

An electronic device according to an exemplary embodiment for realizing the aforementioned object of the present invention includes a light-emitting element including a hole transporting layer which includes the compound represented by Formula 1.

Effect of the Invention

According to the novel compound, the light-emitting element and the electronic device including the same, the novel compound of the present invention may improve the capability of injecting and/or transporting a hole in a light-emitting element. Further, by using the compound, the light-emitting efficiency of the light-emitting element may be improved, and the lifespan thereof may be increased. In addition, thermal stability (heat resistance) of the light-emitting element may be improved.

BRIEF DESCRIPTION OF DRAWINGS

FIG. 1 is a cross-sectional view for describing a light-emitting element according to an exemplary embodiment of the present invention.

FIG. 2 is a cross-sectional view for describing a light-emitting element according to another exemplary embodiment of the present invention.

FIG. 3 is a cross-sectional view for describing a light-emitting element according to still another exemplary embodiment of the present invention.

DETAILED DESCRIPTION OF THE INVENTION

Hereinafter, a novel compound according to the present invention will be first described, and a light-emitting element including the compound will be described in more detail with reference to the accompanying drawings.

The compound according to the present invention is represented by the following Formula 1.

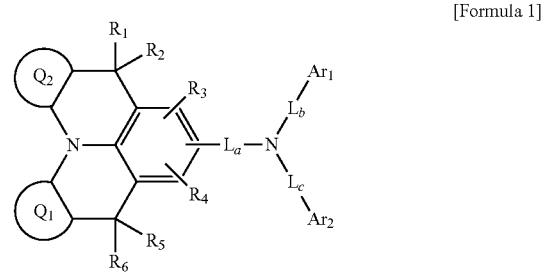

[Formula 1]

In Formula 1, $L_a$, $L_b$, and $L_c$ each independently represent *-$L_1$-$L_2$-$L_3$-$L_4$-* and $Ar_1$ and $Ar_2$ each independently represent *-$A_1$-$A_2$-$A_3$-$A_4$, $L_1$, $L_2$, $L_3$, and $L_4$ each independently represent a single bond, —O—, —S—, an arylene group having 6 to 60 carbon atoms, a heteroarylene group having 2 to 60 carbon atoms, an alkenylene group having 2 to 60 carbon atoms, a cycloalkylene group having 3 to 60 carbon atoms, or a heterocycloalkylene group having 2 to 60 carbon atoms, $A_1$, $A_2$, and $A_3$ each independently represent a single bond, —O—, —S—, a linear or branched alkylene group (—($CH_2$)$_j$—, here, j is an integer of 1 to 60) having 1 to 60 carbon atoms, an arylene group having 6 to 60 carbon atoms, a heteroarylene group having 2 to 60 carbon atoms, a cycloalkylene group having 3 to 60 carbon atoms, a heterocycloalkylene group 2 to 60 carbon atoms, an adamantylene group, a bicycloalkylene group having 7 to 60 carbon atoms, or an alkenylene group having 2 to 60 carbon atoms, and $A_4$ represents hydrogen, an alkyl group having 1 to 60 carbon atoms, an aryl group having 6 to 60 carbon atoms, a heteroaryl group having 2 to 60 carbon atoms, a cycloalkyl group having 3 to 60 carbon atoms, a heterocycloalkyl group having 2 to 60 carbon atoms, an adamantyl group, a bicycloalkyl group having 7 to 60 carbon atoms, the following Formula 2 or the following Formula 3.

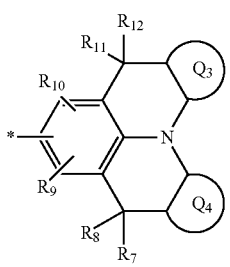

[Formula 2]

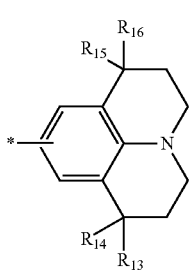

[Formula 3]

In Formulae 1 and 2, $Q_1$, $Q_2$, $Q_3$, and $Q_4$ each independently represent an aryl group having 6 to 60 carbon atoms or a heteroaryl group having 2 to 60 carbon atoms, which is unsubstituted or substituted with one or more selected from the group consisting of an alkyl group having 1 to 12 carbon atoms, an alkoxy group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, or an alkenyl group having 2 to 12 carbon atoms.

In Formulae 1, 2, and 3, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ each independently represent hydrogen, an alkyl group having 1 to 6 carbon atoms, an alkoxy group having 1 to 6 carbon atoms, an aryl group having 6 to 20 carbon atoms, or a heteroaryl group having 2 to 20 carbon atoms.

In this case, hydrogen atoms of $Q_1$, $Q_2$, $L_a$, $L_b$, $L_c$, $Ar_1$, and $Ar_2$ of Formula 1 are each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

In Formulae 1 and 2, $Q_1$, $Q_2$, $Q_3$, and $Q_4$ each mean a fused structure. For example, $Q_1$ represents a substituent fused to a heterocyclic structure, which is a main structure of Formula 1.

In the present invention, "an aryl group" is defined as a monovalent substituent derived from an aromatic hydrocarbon.

Specific examples of the aryl group include a phenyl group, a naphthyl group, an anthracenyl group, a phenanathryl group, a naphthacenyl group, a pyrenyl group, a tolyl group, a biphenylyl group, a terphenylyl group, a chrycenyl group, a spirobifluorenyl group, a fluoranthenyl group, a fluorenyl group, a perylenyl group, an indenyl group, an azulenyl group, a heptalenyl group, a phenalenyl group, a phenanthrenyl group, and the like.

"A heteroaryl group" represents "an aromatic heterocyclic ring" or "a heterocyclic" derived from a monocyclic or fused ring. The heteroaryl group may include at least one of nitrogen (N), sulfur (S), oxygen (O), phosphorus (P), selenium (Se), and silicon (Si) as a heteroatom.

Specific examples of the heteroaryl group include: a nitrogen-containing heteroaryl group including a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolinyl group, a quinolizinyl group, a phthalazinyl group, a naphthylidinyl group, a quinoxalinyl group, a quinazolinyl group, a cinnolinyl group, a pteridinyl group, an imidazotriazinyl group, a pyrazinopyridazinyl group, an acridinyl group, a phenanthridinyl group, a carbazolyl group, a carbazolinyl group, a pyrimidinyl group, a phenanthrolinyl group, a phenazinyl group, an imidazopyridinyl group, an imidazopyrimidinyl group, a pyrazolopyridinyl group, and the like; a sulfur-containing heteroaryl group including a thienyl group, a benzothienyl group, a dibenzothienyl group, and the like; an oxygen-containing heteroaryl group including a furyl group, a pyranyl group, a cyclopentapyranyl group, a benzofuranyl group, an isobenzofuranyl group, a dibenzofuranyl group, and the like; and the like. Further, specific examples of the heteroaryl group include compounds including at least two heteroatoms, such as a thiazolyl group, an isothiazolyl group, a benzothiazolyl group, a benzothiadiazolyl group, a phenothiazinyl group, an isoxazolyl group, a furazanyl group, a phenoxazinyl group, an oxazolyl group, a benzoxazolyl group, an oxadiazolyl group, a pyrazoloxazolyl group, an imidazothiazolyl group, a thienofuranyl group, a furopyrrolyl group, and a pyridoxazinyl group.

The "alkyl group" is defined as a functional group derived from a linear or branched, saturated hydrocarbon.

Specific examples of the alkyl group include a methyl group, an ethyl group, an n-propyl group, an iso-propyl group, an n-butyl group, a sec-butyl group, a tert-butyl group, an n-pentyl group, a 1,1-dimethylpropyl group, a 1,2-dimethylpropyl group, a 2,2-dimethylpropyl group, a 1-ethylpropyl group, a 2-ethylpropyl group, an n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like.

In addition, "an arylene group" may mean a divalent substituent derived from the aryl group described above.

Furthermore, "a heteroarylene group" may mean a divalent substituent derived from the heteroaryl group described above.

In an exemplary embodiment, the compound represented by Formula 1 may include a compound represented by the following Formula 4.

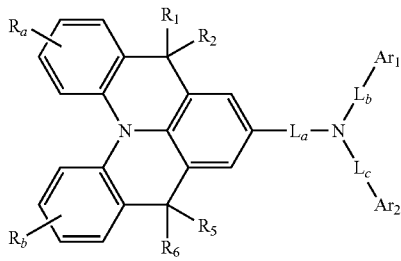

[Formula 4]

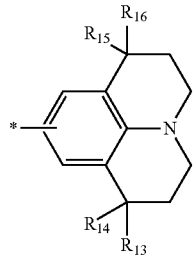

In Formula 4, $L_a$, $L_b$, and $L_c$ each independently represent *-$L_1$-$L_2$-$L_3$-$L_4$-*, $L_1$, $L_2$, $L_3$, and $L_4$ each independently represent a single bond, —O—, —S—, an arylene group having 6 to 60 carbon atoms, a heteroarylene group having 2 to 60 carbon atoms, an alkenylene group having 2 to 60 carbon atoms, a cycloalkylene group having 3 to 60 carbon atoms, or a heterocycloalkylene group having 2 to 60 carbon atoms, but the case where all of $L_1$, $L_2$, $L_3$, and $L_4$ of $L_a$ represent a single bond is excluded. That is, in Formula 4, the case where La is a single bond is excluded from the present invention.

$Ar_1$ and $Ar_2$ each independently represent *-$A_1$-$A_2$-$A_3$-$A_4$, $A_1$, $A_2$, and $A_3$ each independently represent a single bond, —O—, —S—, a linear or branched alkylene group (—(CH$_2$)$_j$—, here, j is an integer of 1 to 60) having 1 to 60 carbon atoms, an arylene group having 6 to 60 carbon atoms, a heteroarylene group having 2 to 60 carbon atoms, a cycloalkylene group having 3 to 60 carbon atoms, a heterocycloalkylene group 2 to 60 carbon atoms, an adamantylene group, or a bicycloalkylene group having 7 to 60 carbon atoms, $A_4$ represents hydrogen, an alkyl group having 1 to 60 carbon atoms, an aryl group having 6 to 60 carbon atoms, a heteroaryl group having 2 to 60 carbon atoms, a cycloalkyl group having 3 to 60 carbon atoms, a heterocycloalkyl group having 2 to 60 carbon atoms, an adamantyl group, a bicycloalkyl group having 7 to 60 carbon atoms, the following Formula 5 or the following Formula 6;

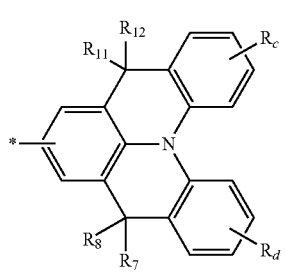

[Formula 5]

[Formula 6]

$R_1$, $R_2$, $R_5$, $R_6$, $R_7$, $R_8$, $R_{11}$, $R_{12}$, $R_{13}$, $R_{14}$, $R_{15}$, and $R_{16}$ each independently represent hydrogen, an alkyl group having 1 to 6 carbon atoms, an alkoxy group having 1 to 6 carbon atoms, an aryl group having 6 to 20 carbon atoms, or a heteroaryl group having 2 to 20 carbon atoms, $R_a$, $R_b$, $R_c$, and $R_d$ each independently represent hydrogen, an alkyl group having 1 to 12 carbon atoms, an alkoxy group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, or an alkenyl group having 2 to 12 carbon atoms, and the hydrogen atoms of $R_a$, $R_b$, $L_a$, $L_b$, $L_c$, $Ar_1$, and $Ar_2$ of Formula 4 may be each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

For example, in Formula 4, $R_1$, $R_2$, $R_5$, and $R_6$ are each independently selected from hydrogen, a methyl group, or a methoxy group, and $R_a$ and $R_b$ are each selected from hydrogen, an alkyl group having 1 to 4 carbon atoms, an alkoxy group having 1 to 4 carbon atoms, or the structures of the following Table 1, and may be the same as each other.

TABLE 1

| No. | Substituent structure |
|---|---|
| 1 | *—⌬ |
| 2 | *—⌬—⌬ |

In this case, in Formula 4, $A_1$ and $A_2$ may be each independently selected from the structures of the following Table 2.

TABLE 2

| No. | Substituent structure |
|---|---|
| 1 | *—⌬ |

TABLE 2-continued
| No. | Subsituent structure |
|---|---|
| 2 | 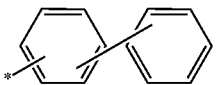 |
| 3 | 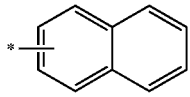 |
| 4 | 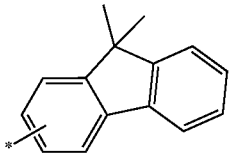 |
| 5 | 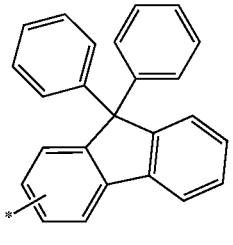 |
| 6 | 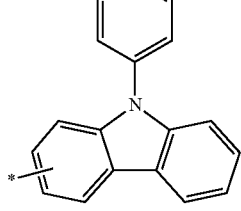 |
| 7 | 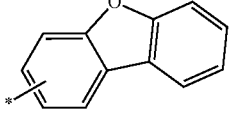 |
| 8 | 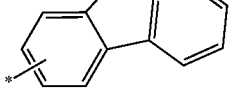 |
| 9 | 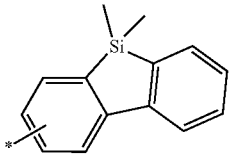 |
| 10 | 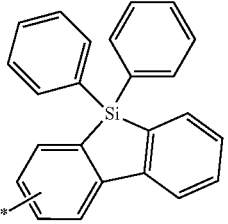 |
| 11 | 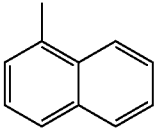 |
| 12 | 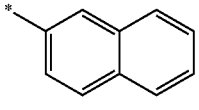 |
Substituent No. 3 in Table 2 may specifically represent the following Formula 2-3a or the following Formula 2-3b.
[Formula 2-3a]
[Formula 2-3b]
Substituent No. 4 in Table 2 may specifically represent the following Formula 2-4a or the following Formula 2-4b.
[Formula 2-4a]
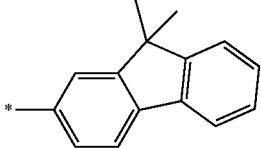

[Formula 2-4b]

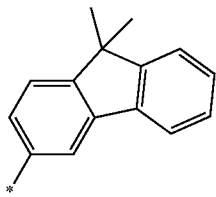

Substituent No. 5 in Table 2 may specifically represent the following Formula 2-5a or the following Formula 2-5b.

[Formula 2-5a]

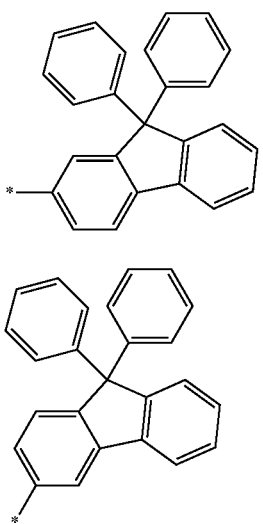

[Formula 2-5b]

Substituent No. 6 in Table 2 may specifically represent the following Formula 2-6a or the following Formula 2-6b.

[Formula 2-6a]

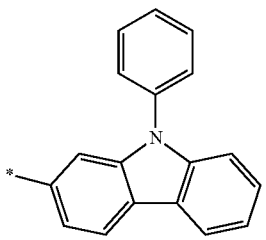

[Formula 2-6b]

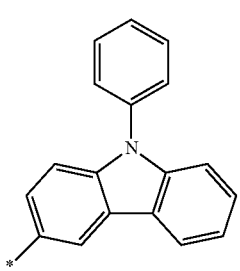

Substituent No. 7 in Table 2 may specifically represent the following Formula 2-7a or the following Formula 2-7b.

[Formula 2-7a]

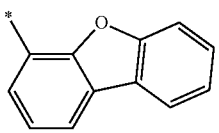

[Formula 2-7b]

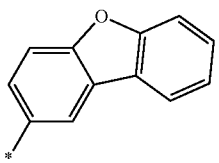

Substituent No. 8 in Table 2 may specifically represent the following Formula 2-8a or the following Formula 2-8b.

[Formula 2-8a]

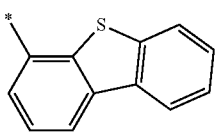

[Formula 2-8b]

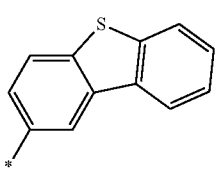

Substituent No. 9 in Table 2 may specifically represent the following Formula 2-9a or the following Formula 2-9b.

[Formula 2-9a]

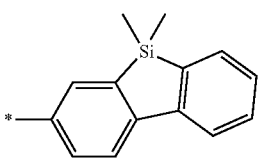

[Formula 2-9b]

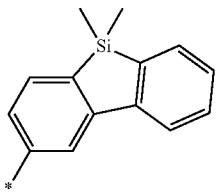

Substituent No. 10 in Table 2 may specifically represent the following Formula 2-10a or the following Formula 2-10b.

[Formula 2-10a]

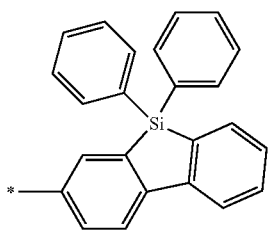

[Formula 2-10b]

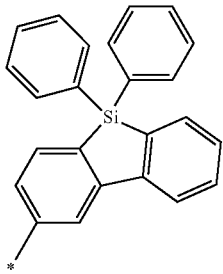

Substituent No. 11 in Table 2 may specifically represent the following Formula 2-11a or the following Formula 2-11b.

[Formula 2-11a]

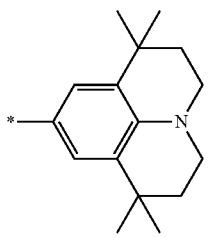

[Formula 2-11b]

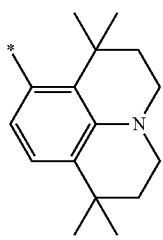

Further, Substituent No. 12 in Table 2 may specifically represent the following Formula 2-12a or the following Formula 2-12b.

[Formula 2-12a]

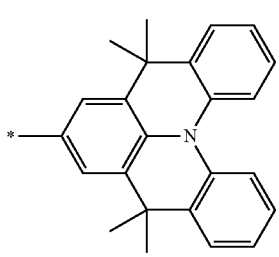

[Formula 2-12b]

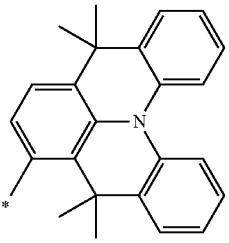

In Formula 4, $L_a$ may be selected from the structures of the following Table 3, $L_b$ and $L_c$ may be each independently selected from a single bond or the structures of the following Table 3.

TABLE 3

| No. | Substituent structure |
|---|---|
| 1 |  |
| 2 |  |
| 3 |  |
| 4 | 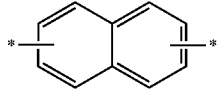 |
| 5 | 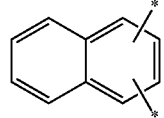 |
| 6 | 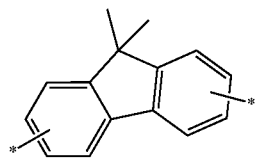 |
| 7 | 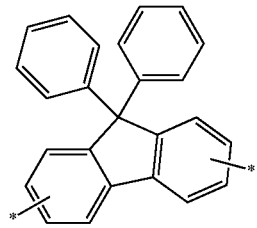 |

TABLE 3-continued

| No. | Subsituent structure |
|---|---|
| 8 | 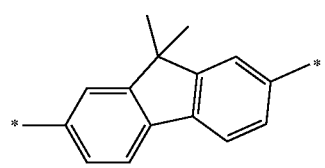 |
| 9 | |
| 10 | |
| 11 | |

Substituent No. 6 in Table 3 may specifically represent the following Formula 3-6a or the following Formula 3-6b.

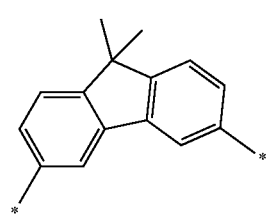

[Formula 3-6a]

[Formula 3-6b]

Substituent No. 7 in Table 3 may specifically represent the following Formula 3-7a or the following Formula 3-7b.

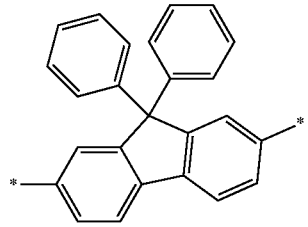

[Formula 3-7a]

[Formula 3-7b]

Substituent No. 8 in Table 3 may specifically represent the following Formula 3-8a or the following Formula 3-8b.

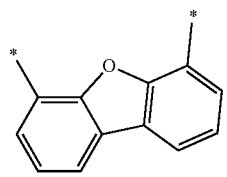

[Formula 3-8a]

[Formula 3-8b]

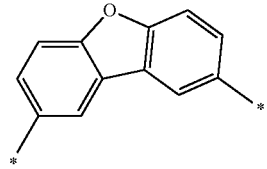

Substituent No. 9 in Table 3 may specifically represent the following Formula 3-9a or the following Formula 3-9b.

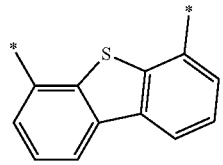

[Formula 3-9a]

[Formula 3-9b]

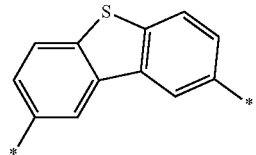

Substituent No. 10 in Table 3 may specifically represent the following Formula 3-10a or the following Formula 3-10b.

[Formula 3-10a]

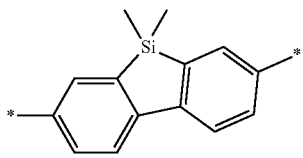

[Formula 3-10b]

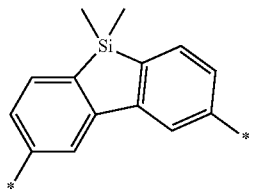

Substituent No. 11 in Table 3 may specifically represent the following Formula 3-11a or the following Formula 3-11b.

[Formula 3-11a]

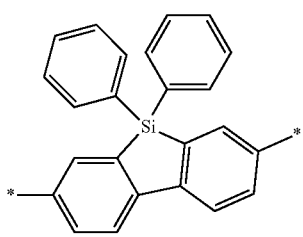

[Formula 3-11b]

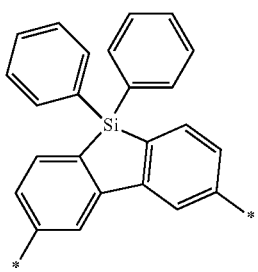

As a specific example, the compound represented by Formula 1 may include a compound represented by the following Formula 7.

[Formula 7]

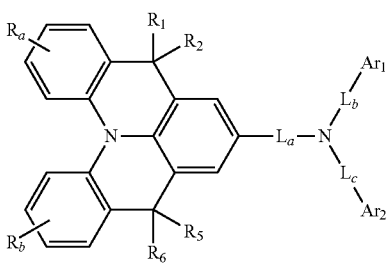

In Formula 7, $L_a$, $L_b$, and $L_c$ each independently represent a single bond, an arylene group having 6 to 30 carbon atoms, or a heteroarylene group having 2 to 30 carbon atoms, but the case where $L_a$ is a single bond is excluded, $Ar_1$ and $Ar_2$ each independently represent hydrogen, an alkyl group having 1 to 10 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, the following Formula 8 or the following Formula 9;

[Formula 8]

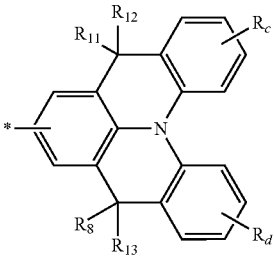

[Formula 9]

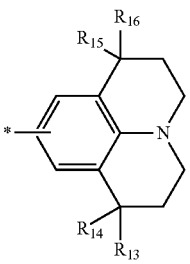

$R_1$, $R_2$, $R_5$, $R_6$, $R_7$, $R_8$, $R_{11}$, $R_{12}$, $R_{13}$, $R_{14}$, $R_{15}$, and $R_{16}$ each independently represent hydrogen, an alkyl group having 1 to 6 carbon atoms, or an alkoxy group having 1 to 6 carbon atoms, $R_a$, $R_b$, $R_c$, and $R_d$ each independently represent hydrogen, an alkyl group having 1 to 12 carbon atoms, an alkoxy group having 1 to 12 carbon atoms, an aryl group having 6 to 30 carbon atoms, or a heteroaryl group having 2 to 30 carbon atoms, and the hydrogen atoms of $R_a$, $R_b$, $L_a$, $L_b$, $L_c$, $Ar_1$, and $Ar_2$ of Formula 7 may be each independently unsubstituted or substituted with one selected from the group consisting of an alkyl group having 1 to 6 carbon atoms, an alkoxy group having 1 to 6 carbon atoms, an aryl group having 6 to 20 carbon atoms, a heteroaryl group having 2 to 20 carbon atoms, a halogen group, a cyano group, and a nitro group.

Specific examples of the compound represented by Formula 1 include compounds represented by the following Structures 1 to 120 in the following Table 4. The present invention is not limited to the following specific structures.

TABLE 4
| No. | Structure |
|---|---|
| 1 | 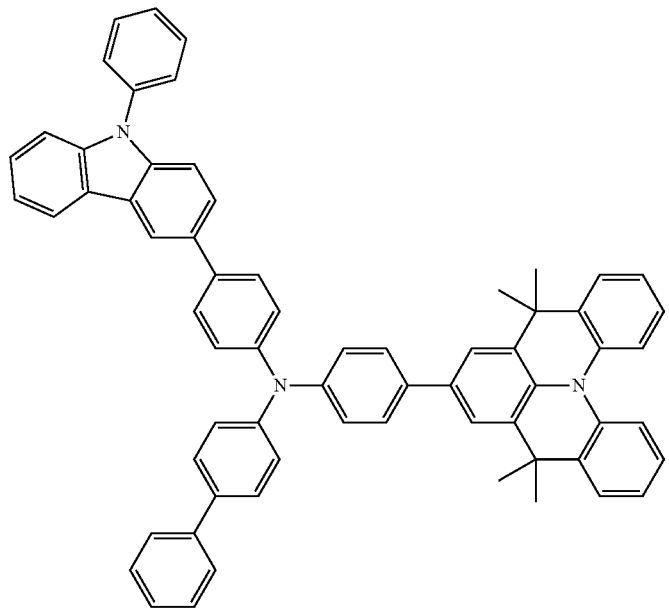 [SMILES: CC1(C)c2ccccc2N2c3ccccc3C(C)(C)c3cc(-c4ccc(N(c5ccc(-c6ccccc6)cc5)c5ccc(-c6ccc7c(c6)c6ccccc6n7-c6ccccc6)cc5)cc4)cc1c32] |
| 2 | 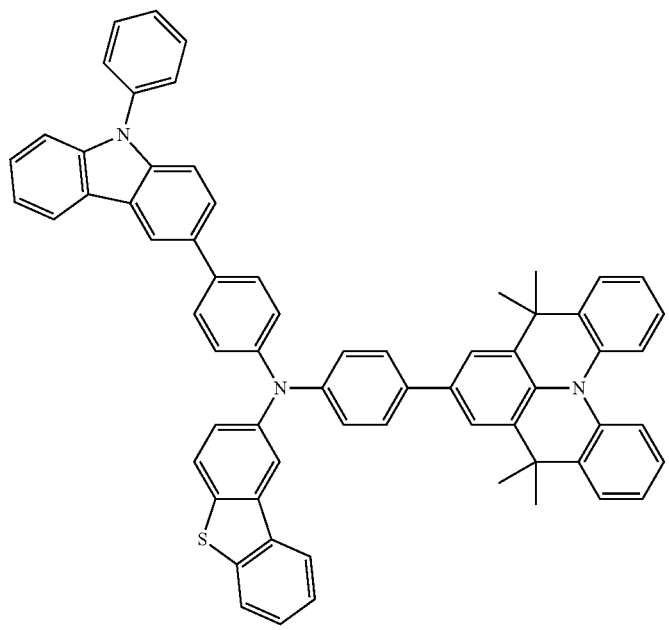 [SMILES: CC1(C)c2ccccc2N2c3ccccc3C(C)(C)c3cc(-c4ccc(N(c5ccc(-c6ccc7c(c6)c6ccccc6n7-c6ccccc6)cc5)c5ccc6sc7ccccc7c6c5)cc4)cc1c32] |

TABLE 4-continued
| No. | Structure |
|---|---|
| 3 | 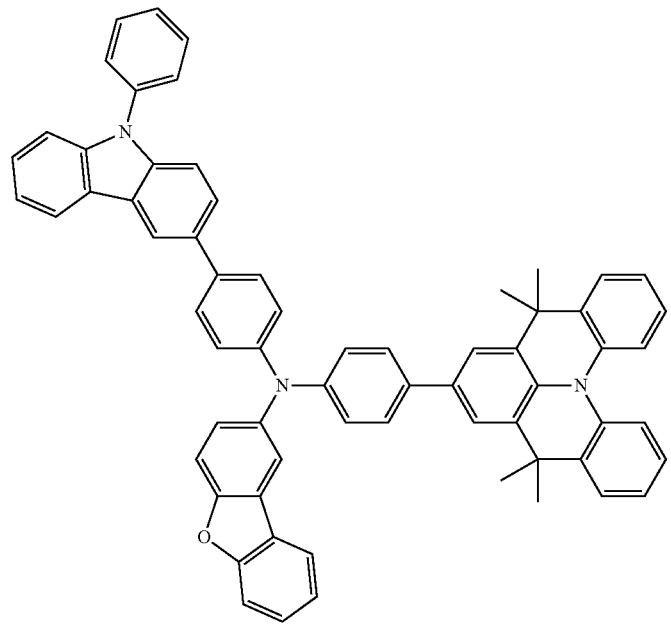 [SMILES: CC1(C)c2ccccc2N2c3ccccc3C(C)(C)c3cc(-c4ccc(N(c5ccc(-c6ccc7c(c6)c6ccccc6n7-c6ccccc6)cc5)c5ccc6oc7ccccc7c6c5)cc4)cc1c32] |
| 4 | 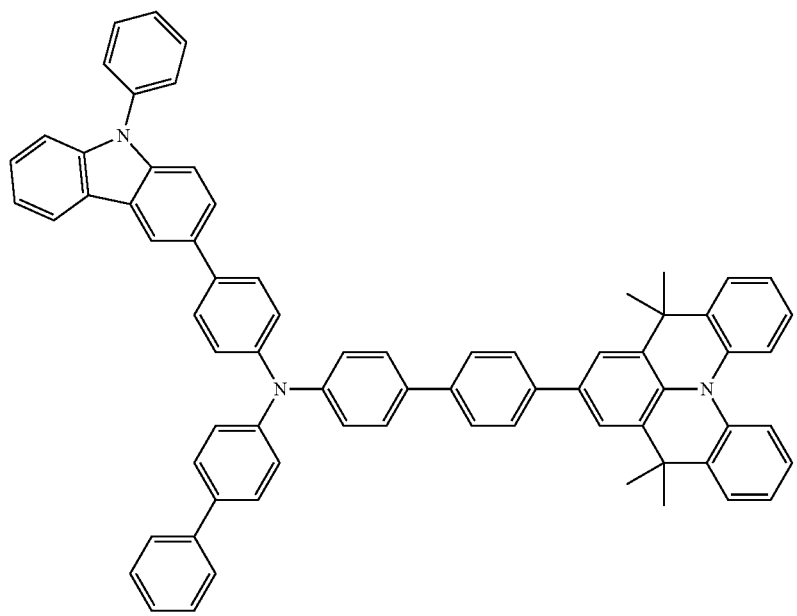 [SMILES: CC1(C)c2ccccc2N2c3ccccc3C(C)(C)c3cc(-c4ccc(-c5ccc(N(c6ccc(-c7ccccc7)cc6)c6ccc(-c7ccc8c(c7)c7ccccc7n8-c7ccccc7)cc6)cc5)cc4)cc1c32] |

TABLE 4-continued

| No. | Structure |
|---|---|
| 5 | 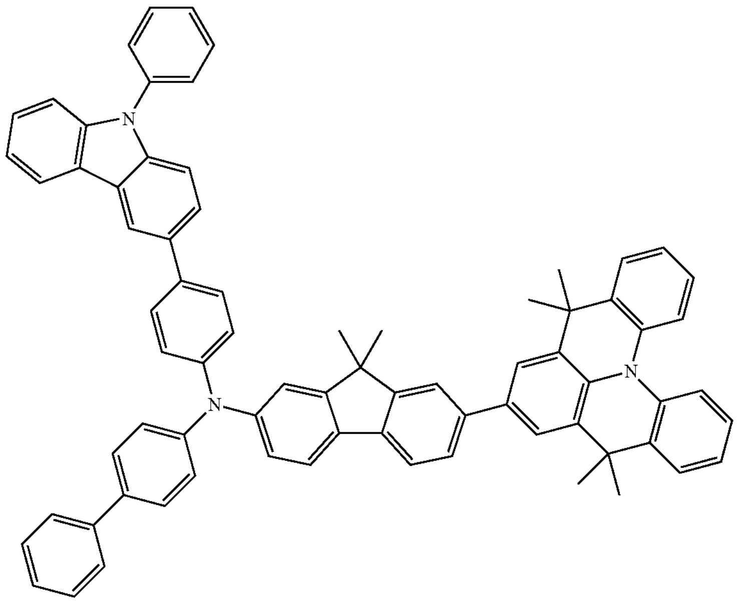 [SMILES: CC1(C)c2cc(-c3cc4c5c(c3)C(C)(C)c3ccccc3N5c3ccccc3C4(C)C)ccc2-c2ccc(N(c3ccc(-c4ccccc4)cc3)c3ccc(-c4ccc5c(c4)c4ccccc4n5-c4ccccc4)cc3)cc21] |
| 6 | 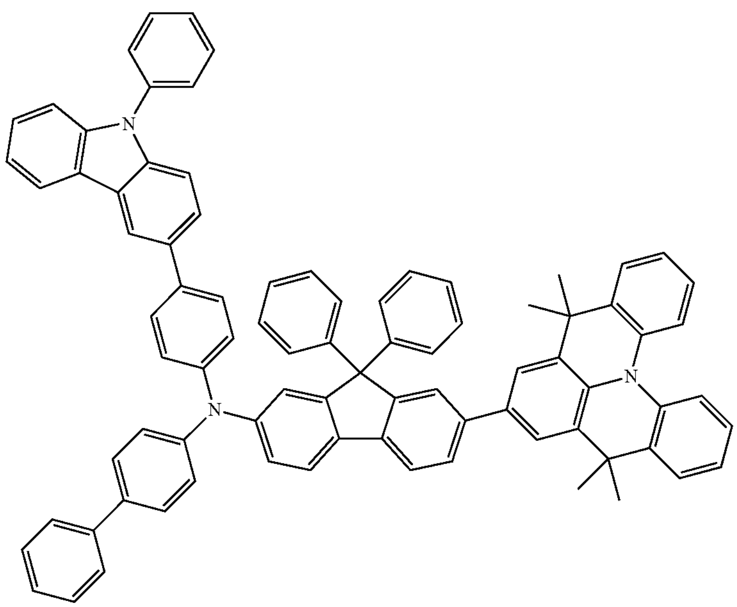 [SMILES: CC1(C)c2ccccc2N2c3ccccc3C(C)(C)c3cc(-c4ccc5c(c4)C(c4ccccc4)(c4ccccc4)c4cc(N(c6ccc(-c7ccccc7)cc6)c6ccc(-c7ccc8c(c7)c7ccccc7n8-c7ccccc7)cc6)ccc4-5)cc1c32] |
| 7 | 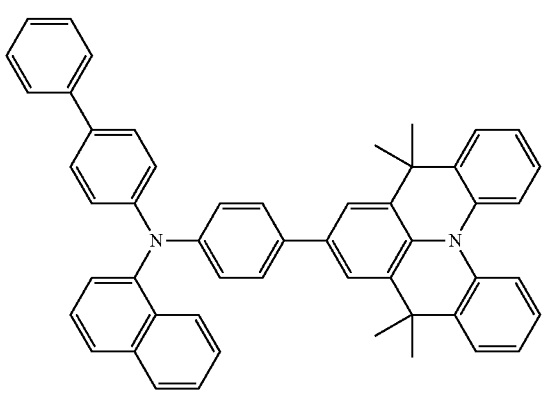 [SMILES: CC1(C)c2ccccc2N2c3ccccc3C(C)(C)c3cc(-c4ccc(N(c5ccc(-c6ccccc6)cc5)c5cccc6ccccc56)cc4)cc1c32] |

TABLE 4-continued
| No. | Structure |
|---|---|
| 8 | 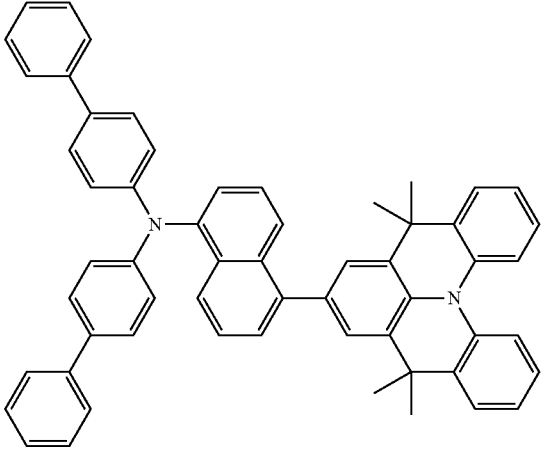 [SMILES: CC1(C)c2ccccc2N2c3ccccc3C(C)(C)c3cc(-c4cccc5c(N(c6ccc(-c7ccccc7)cc6)c6ccc(-c7ccccc7)cc6)cccc45)cc1c32] |
| 9 | 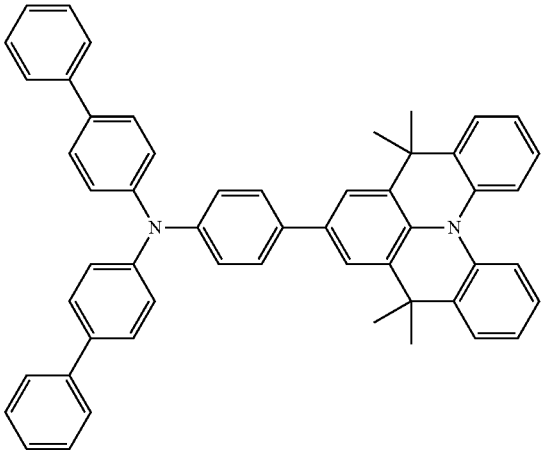 [SMILES: CC1(C)c2ccccc2N2c3ccccc3C(C)(C)c3cc(-c4ccc(N(c5ccc(-c6ccccc6)cc5)c5ccc(-c6ccccc6)cc5)cc4)cc1c32] |
| 10 | 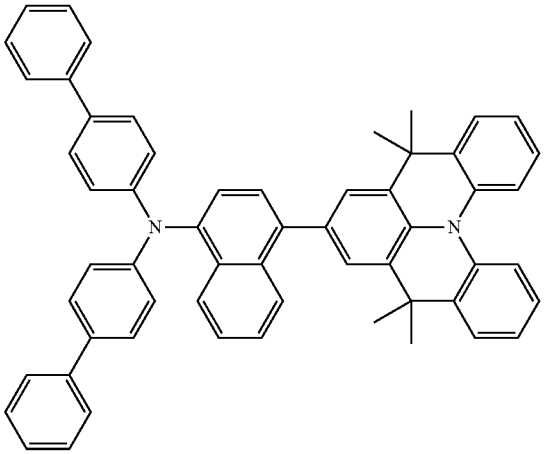 [SMILES: CC1(C)c2ccccc2N2c3ccccc3C(C)(C)c3cc(-c4ccc(N(c5ccc(-c6ccccc6)cc5)c5ccc(-c6ccccc6)cc5)c5ccccc45)cc1c32] |

TABLE 4-continued

| No. | Structure |
| --- | --- |
| 11 | 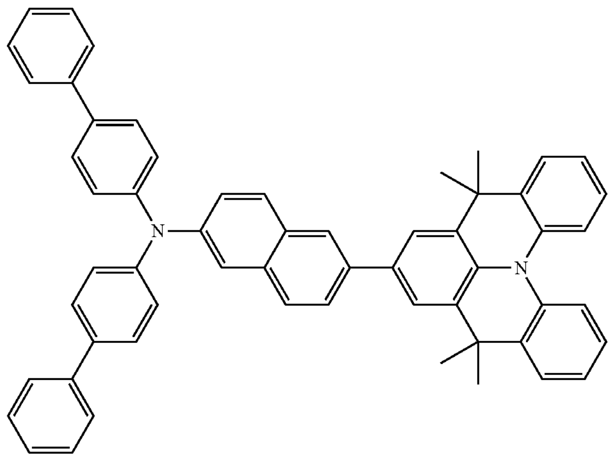 [SMILES: CC1(C)c2ccccc2N2c3ccccc3C(C)(C)c3cc(-c4ccc5cc(N(c6ccc(-c7ccccc7)cc6)c6ccc(-c7ccccc7)cc6)ccc5c4)cc1c32] |
| 12 | 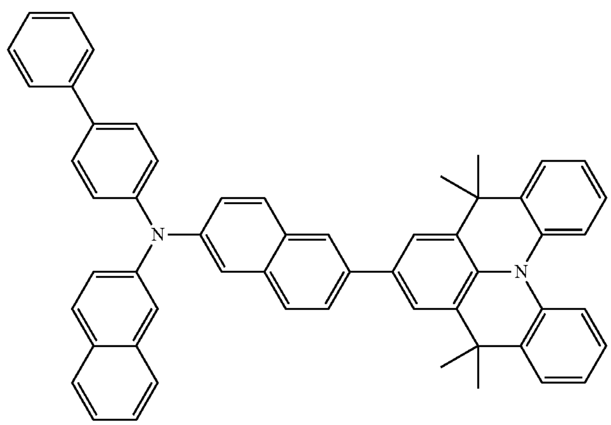 [SMILES: CC1(C)c2ccccc2N2c3ccccc3C(C)(C)c3cc(-c4ccc5cc(N(c6ccc(-c7ccccc7)cc6)c6ccc7ccccc7c6)ccc5c4)cc1c32] |
| 13 | 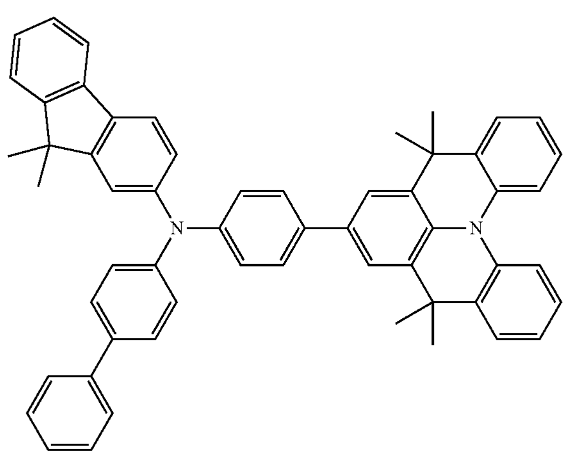 [SMILES: CC1(C)c2ccccc2-c2ccc(N(c3ccc(-c4ccccc4)cc3)c3ccc(-c4cc5c6c(c4)C(C)(C)c4ccccc4N6c4ccccc4C5(C)C)cc3)cc21] |

TABLE 4-continued

| No. | Structure |
| --- | --- |
| 14 | 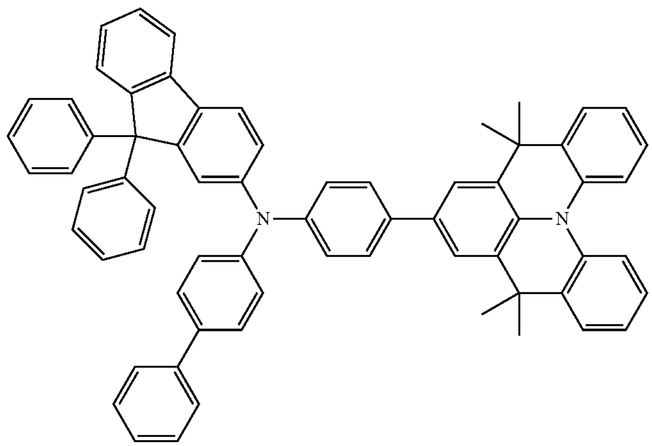 [SMILES: CC1(C)c2ccccc2N2c3ccccc3C(C)(C)c3cc(-c4ccc(N(c5ccc(-c6ccccc6)cc5)c5ccc6c(c5)C(c5ccccc5)(c5ccccc5)c5ccccc5-6)cc4)cc1c32] |
| 15 | 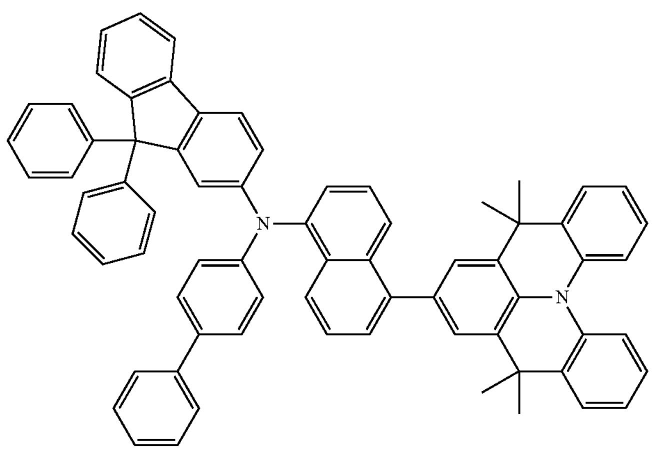 [SMILES: CC1(C)c2ccccc2N2c3ccccc3C(C)(C)c3cc(-c4cccc5c(N(c6ccc(-c7ccccc7)cc6)c6ccc7c(c6)C(c6ccccc6)(c6ccccc6)c6ccccc6-7)cccc45)cc1c32] |
| 16 | 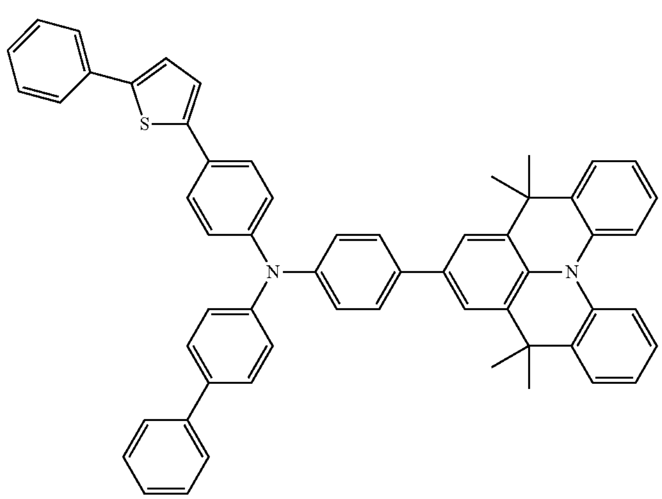 [SMILES: CC1(C)c2ccccc2N2c3ccccc3C(C)(C)c3cc(-c4ccc(N(c5ccc(-c6ccccc6)cc5)c5ccc(-c6ccc(-c7ccccc7)s6)cc5)cc4)cc1c32] |

TABLE 4-continued

| No. | Structure |
| --- | --- |
| 17 | 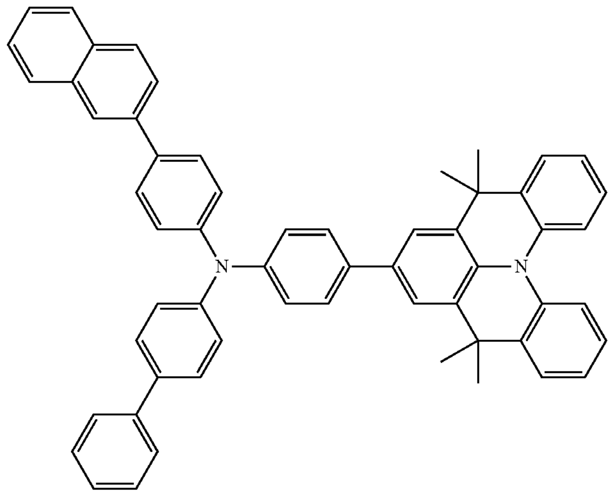 [SMILES: CC1(C)c2ccccc2N2c3ccccc3C(C)(C)c3cc(-c4ccc(N(c5ccc(-c6ccccc6)cc5)c5ccc(-c6ccc7ccccc7c6)cc5)cc4)cc1c32] |
| 18 | 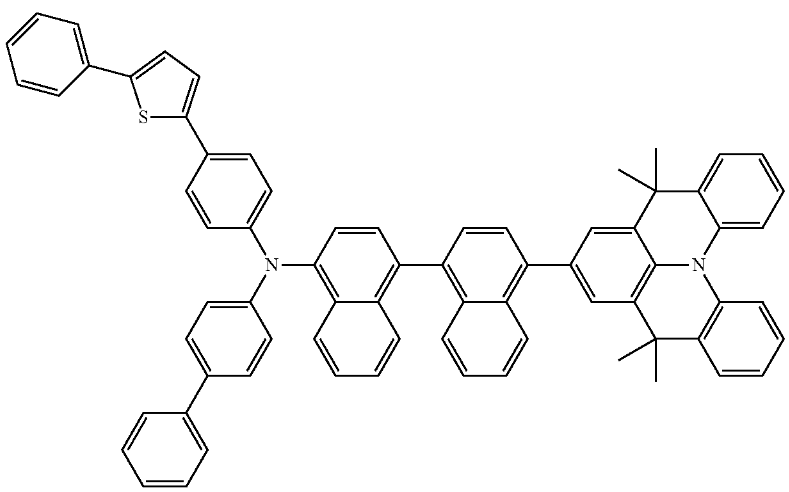 [SMILES: CC1(C)c2ccccc2N2c3ccccc3C(C)(C)c3cc(-c4ccc(-c5ccc(N(c6ccc(-c7ccccc7)cc6)c6ccc(-c7ccc(-c8ccccc8)s7)cc6)c6ccccc56)c5ccccc45)cc1c32] |
| 19 | 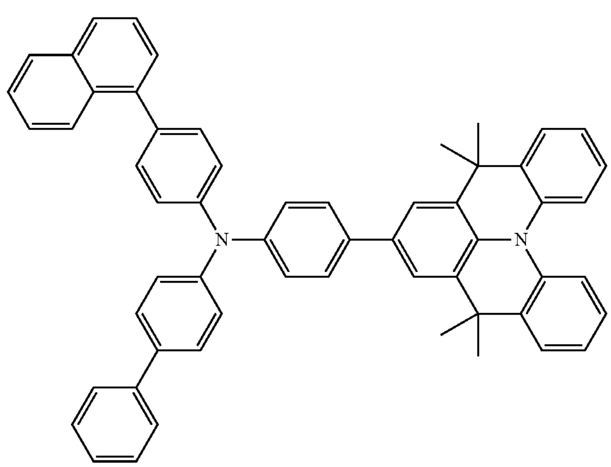 [SMILES: CC1(C)c2ccccc2N2c3ccccc3C(C)(C)c3cc(-c4ccc(N(c5ccc(-c6ccccc6)cc5)c5ccc(-c6cccc7ccccc67)cc5)cc4)cc1c32] |

TABLE 4-continued

| No. | Structure |
|-----|-----------|
| 20 | 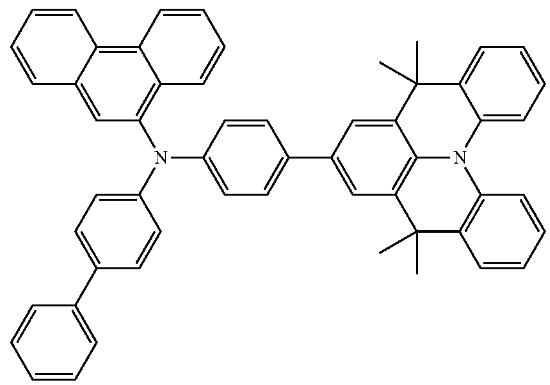 [SMILES: CC1(C)c2ccccc2N2c3ccccc3C(C)(C)c3cc(-c4ccc(N(c5ccc(-c6ccccc6)cc5)c5cc6ccccc6c6ccccc56)cc4)cc1c32] |
| 21 | 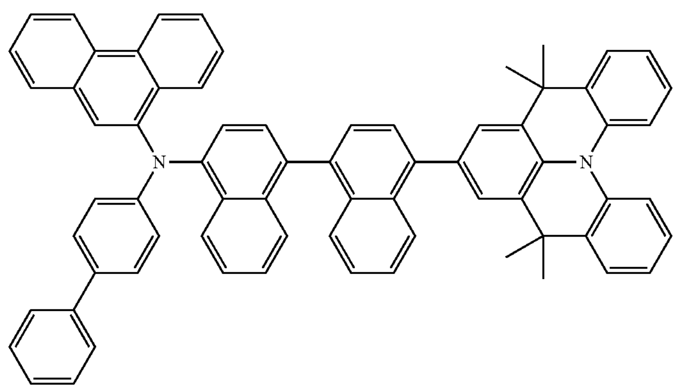 [SMILES: CC1(C)c2ccccc2N2c3ccccc3C(C)(C)c3cc(-c4ccc(-c5ccc(N(c6ccc(-c7ccccc7)cc6)c6cc7ccccc7c7ccccc67)c6ccccc56)c5ccccc45)cc1c32] |
| 22 | 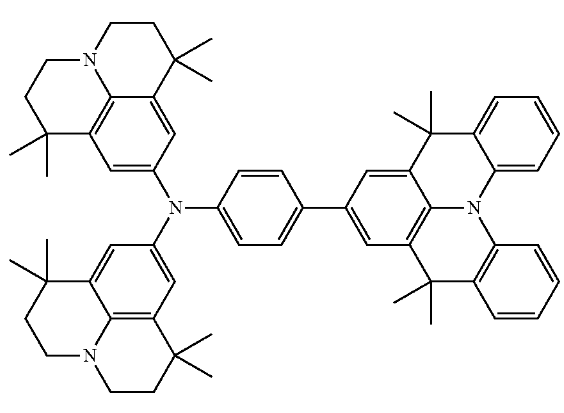 [SMILES: CC1(C)CCN2CCC(C)(C)c3cc(N(c4ccc(-c5cc6c7c(c5)C(C)(C)c5ccccc5N7c5ccccc5C6(C)C)cc4)c4cc5c6c(c4)C(C)(C)CCN6CCC5(C)C)cc1c32] |

TABLE 4-continued
| No. | Structure |
|---|---|
| 23 | 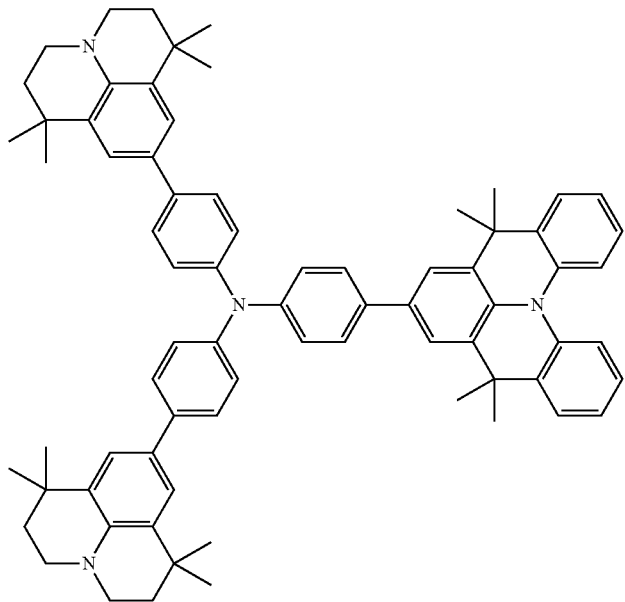 [SMILES: CC1(C)CCN2CCC(C)(C)c3cc(-c4ccc(N(c5ccc(-c6cc7c8c(c6)C(C)(C)CCN8CCC7(C)C)cc5)c5ccc(-c6cc7c8c(c6)C(C)(C)c6ccccc6N8c6ccccc6C7(C)C)cc5)cc4)cc1c32] |
| 24 | 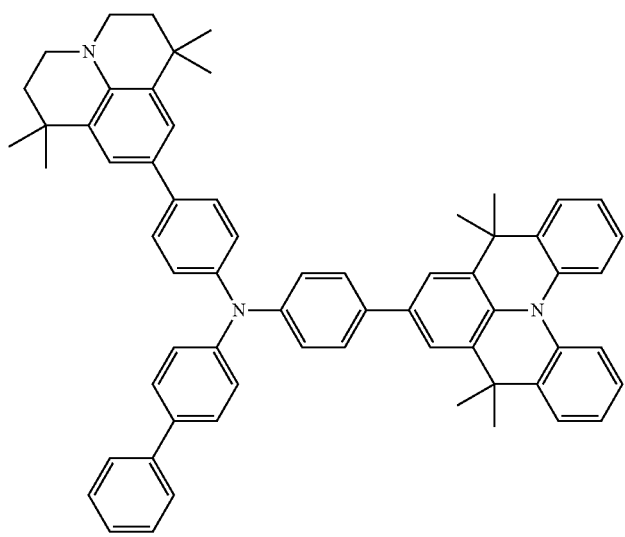 [SMILES: CC1(C)CCN2CCC(C)(C)c3cc(-c4ccc(N(c5ccc(-c6ccccc6)cc5)c5ccc(-c6cc7c8c(c6)C(C)(C)c6ccccc6N8c6ccccc6C7(C)C)cc5)cc4)cc1c32] |

TABLE 4-continued

| No. | Structure |
| --- | --- |
| 25 | 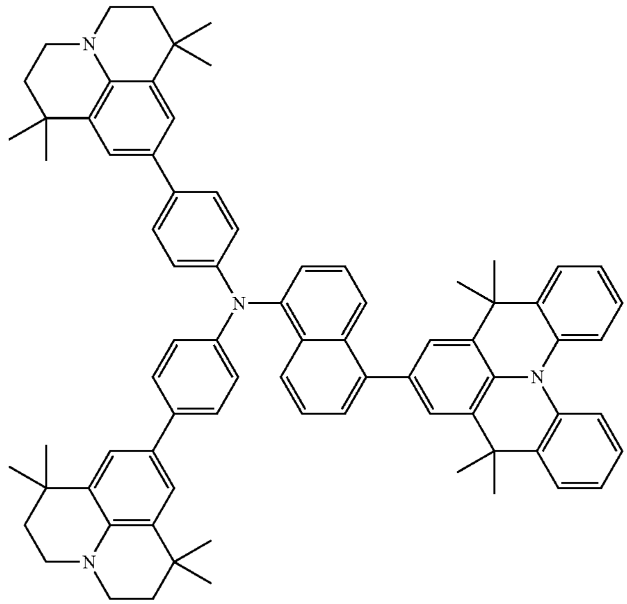 [SMILES: CC1(C)CCN2CCC(C)(C)c3cc(-c4ccc(N(c5ccc(-c6cc7c8c(c6)C(C)(C)CCN8CCC7(C)C)cc5)c5cccc6c(-c7cc8c9c(c7)C(C)(C)c7ccccc7N9c7ccccc7C8(C)C)cccc56)cc4)cc1c32] |
| 26 | 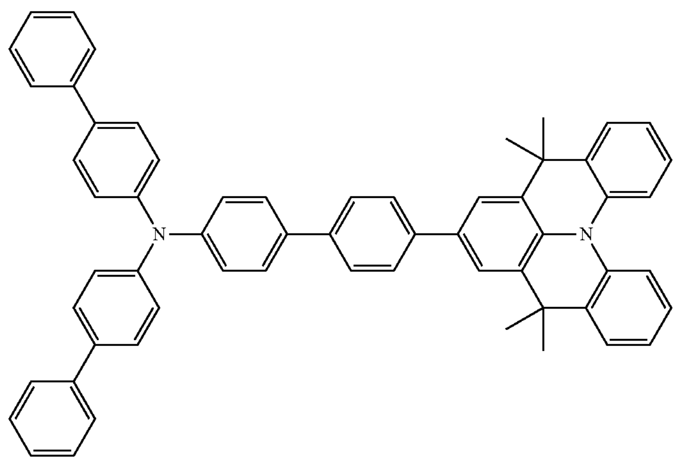 [SMILES: CC1(C)c2ccccc2N2c3ccccc3C(C)(C)c3cc(-c4ccc(-c5ccc(N(c6ccc(-c7ccccc7)cc6)c6ccc(-c7ccccc7)cc6)cc5)cc4)cc1c32] |
| 27 | 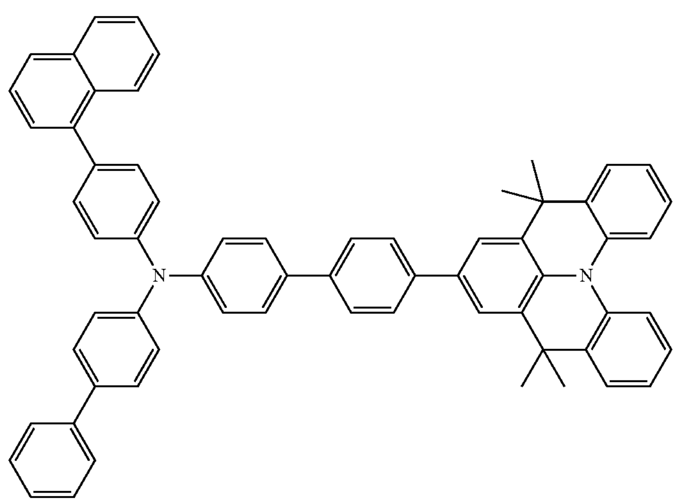 [SMILES: CC1(C)c2ccccc2N2c3ccccc3C(C)(C)c3cc(-c4ccc(-c5ccc(N(c6ccc(-c7ccccc7)cc6)c6ccc(-c7cccc8ccccc78)cc6)cc5)cc4)cc1c32] |

TABLE 4-continued
| No. | Structure |
| --- | --- |
| 28 | 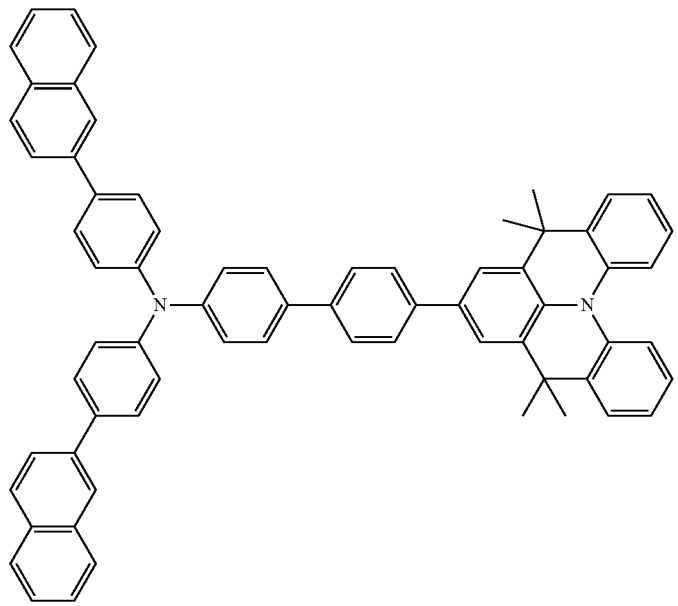 [SMILES: CC1(C)c2ccccc2N2c3ccccc3C(C)(C)c3cc(-c4ccc(-c5ccc(N(c6ccc(-c7ccc8ccccc8c7)cc6)c6ccc(-c7ccc8ccccc8c7)cc6)cc5)cc4)cc1c32] |
| 29 | 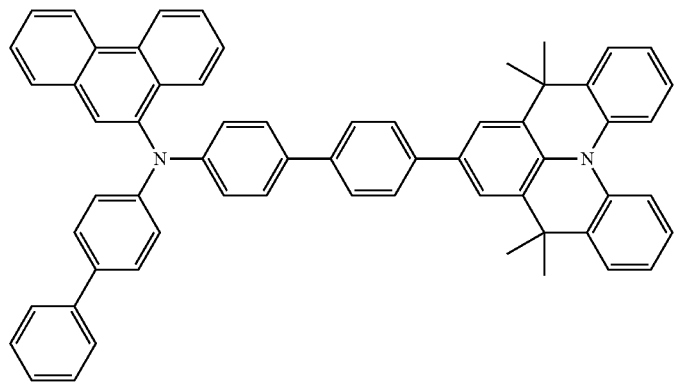 [SMILES: CC1(C)c2ccccc2N2c3ccccc3C(C)(C)c3cc(-c4ccc(-c5ccc(N(c6ccc(-c7ccccc7)cc6)c6cc7ccccc7c7ccccc67)cc5)cc4)cc1c32] |
| 30 | 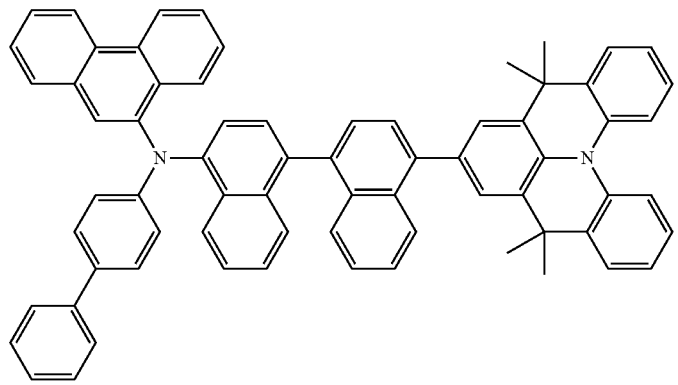 [SMILES: CC1(C)c2ccccc2N2c3ccccc3C(C)(C)c3cc(-c4ccc(-c5ccc(N(c6ccc(-c7ccccc7)cc6)c6cc7ccccc7c7ccccc67)c6ccccc56)c5ccccc45)cc1c32] |

TABLE 4-continued

| No. | Structure |
|---|---|
| 31 | 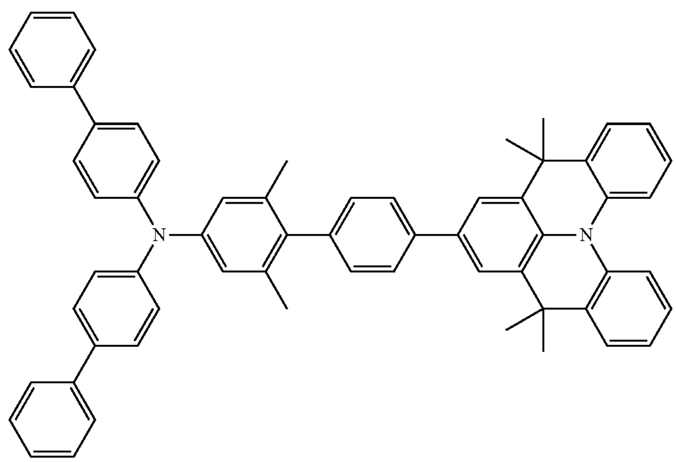 [SMILES: Cc1cc(N(c2ccc(-c3ccccc3)cc2)c2ccc(-c3ccccc3)cc2)cc(C)c1-c1ccc(-c2cc3c4c(c2)C(C)(C)c2ccccc2N4c2ccccc2C3(C)C)cc1] |
| 32 | 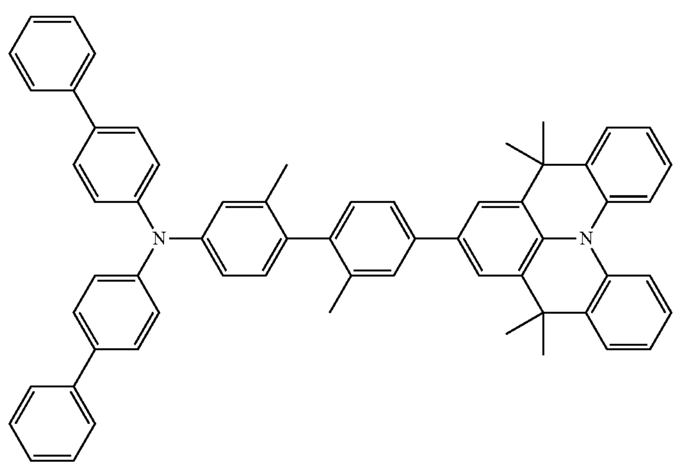 [SMILES: Cc1cc(-c2cc3c4c(c2)C(C)(C)c2ccccc2N4c2ccccc2C3(C)C)ccc1-c1ccc(N(c2ccc(-c3ccccc3)cc2)c2ccc(-c3ccccc3)cc2)cc1C] |
| 33 | 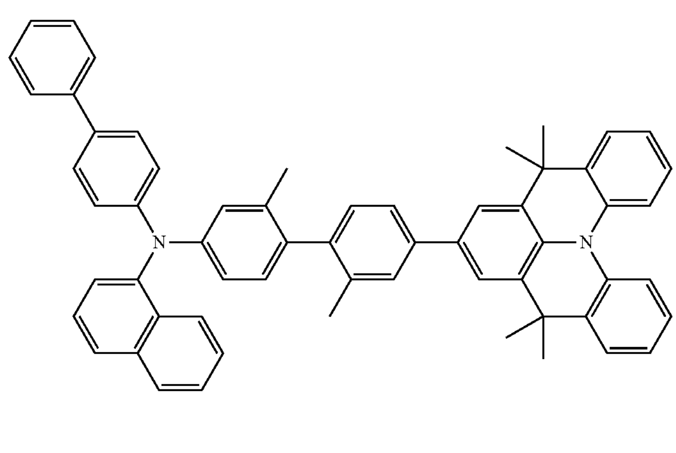 [SMILES: Cc1cc(-c2cc3c4c(c2)C(C)(C)c2ccccc2N4c2ccccc2C3(C)C)ccc1-c1ccc(N(c2ccc(-c3ccccc3)cc2)c2cccc3ccccc23)cc1C] |

TABLE 4-continued
| No. | Structure |
|---|---|
| 34 | 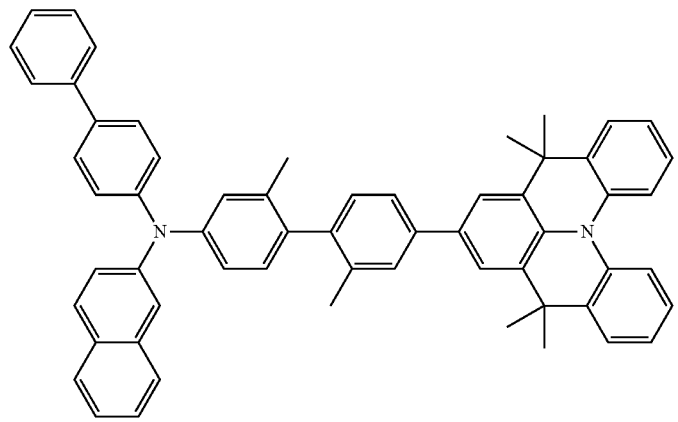 [SMILES: Cc1cc(-c2cc3c4c(c2)C(C)(C)c2ccccc2N4c2ccccc2C3(C)C)ccc1-c1ccc(N(c2ccc(-c3ccccc3)cc2)c2ccc3ccccc3c2)cc1C] |
| 35 | 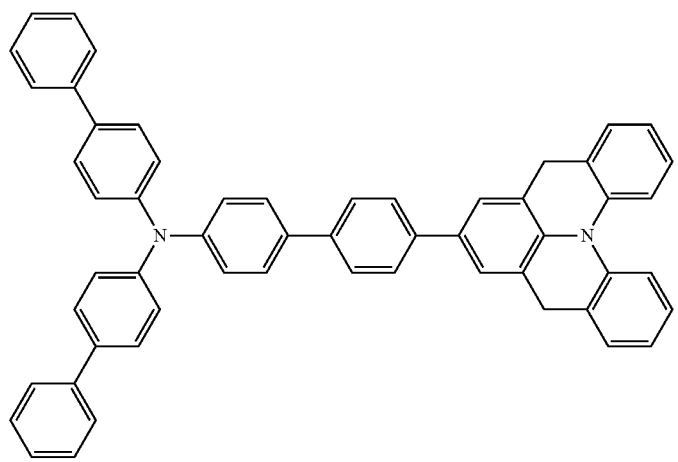 [SMILES: c1ccc(-c2ccc(N(c3ccc(-c4ccccc4)cc3)c3ccc(-c4ccc(-c5cc6c7c(c5)Cc5ccccc5N7c5ccccc5C6)cc4)cc3)cc2)cc1] |
| 36 | 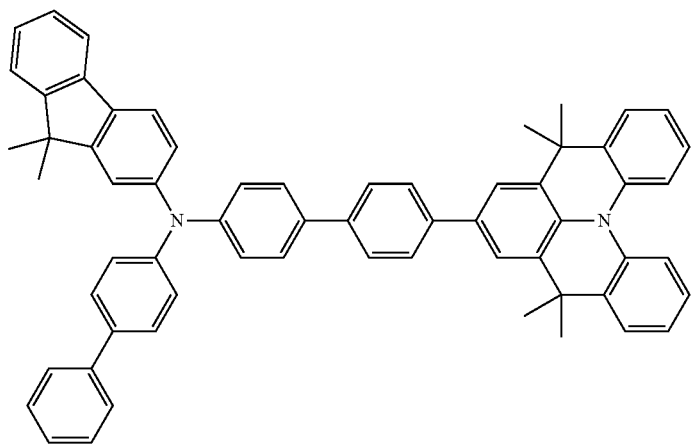 [SMILES: CC1(C)c2ccccc2-c2ccc(N(c3ccc(-c4ccccc4)cc3)c3ccc(-c4ccc(-c5cc6c7c(c5)C(C)(C)c5ccccc5N7c5ccccc5C6(C)C)cc4)cc3)cc21] |

TABLE 4-continued

| No. | Structure |
|---|---|
| 37 | 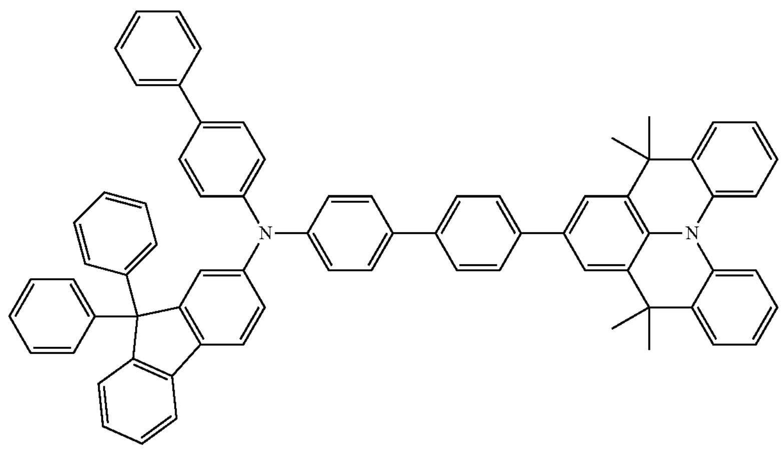 [SMILES: CC1(C)c2ccccc2N2c3ccccc3C(C)(C)c3cc(-c4ccc(-c5ccc(N(c6ccc(-c7ccccc7)cc6)c6ccc7c(c6)C(c6ccccc6)(c6ccccc6)c6ccccc6-7)cc5)cc4)cc1c32] |
| 38 | 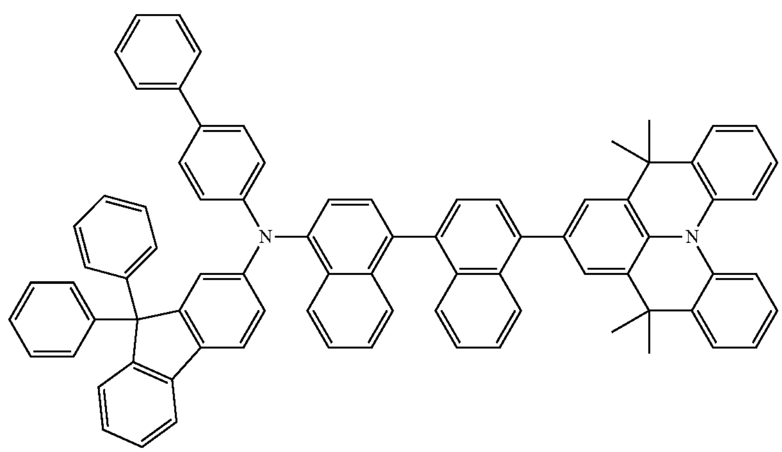 [SMILES: CC1(C)c2ccccc2N2c3ccccc3C(C)(C)c3cc(-c4ccc(-c5ccc(N(c6ccc(-c7ccccc7)cc6)c6ccc7c(c6)C(c6ccccc6)(c6ccccc6)c6ccccc6-7)c6ccccc56)c5ccccc45)cc1c32] |
| 39 | 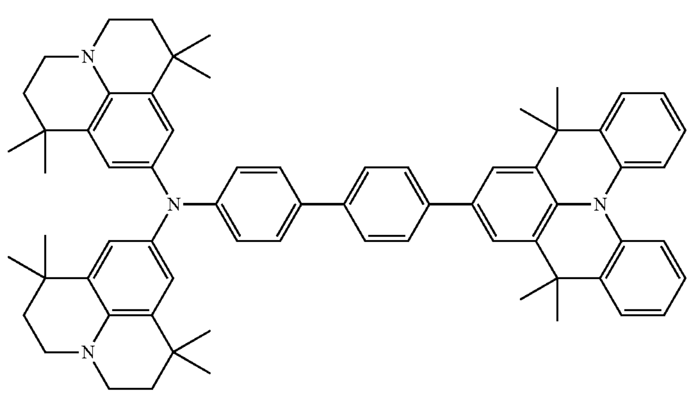 [SMILES: CC1(C)CCN2CCC(C)(C)c3cc(N(c4ccc(-c5ccc(-c6cc7c8c(c6)C(C)(C)c6ccccc6N8c6ccccc6C7(C)C)cc5)cc4)c4cc5c6c(c4)C(C)(C)CCN6CCC5(C)C)cc1c32] |

TABLE 4-continued
| No. | Structure |
|---|---|
| 40 | 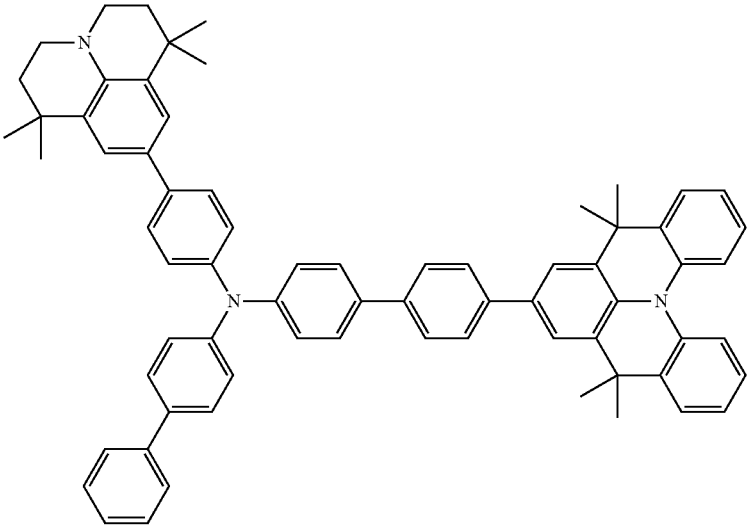 [SMILES: CC1(C)CCN2CCC(C)(C)c3cc(-c4ccc(N(c5ccc(-c6ccccc6)cc5)c5ccc(-c6ccc(-c7cc8c9c(c7)C(C)(C)c7ccccc7N9c7ccccc7C8(C)C)cc6)cc5)cc4)cc1c32] |
| 41 | 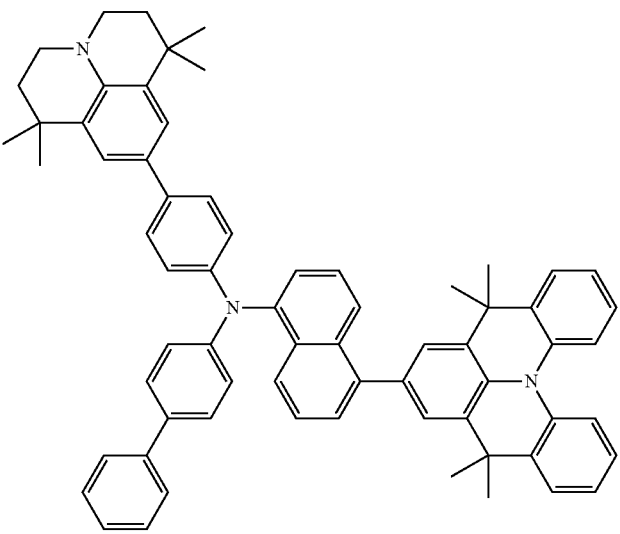 [SMILES: CC1(C)CCN2CCC(C)(C)c3cc(-c4ccc(N(c5ccc(-c6ccccc6)cc5)c5cccc6c(-c7cc8c9c(c7)C(C)(C)c7ccccc7N9c7ccccc7C8(C)C)cccc56)cc4)cc1c32] |
| 42 | 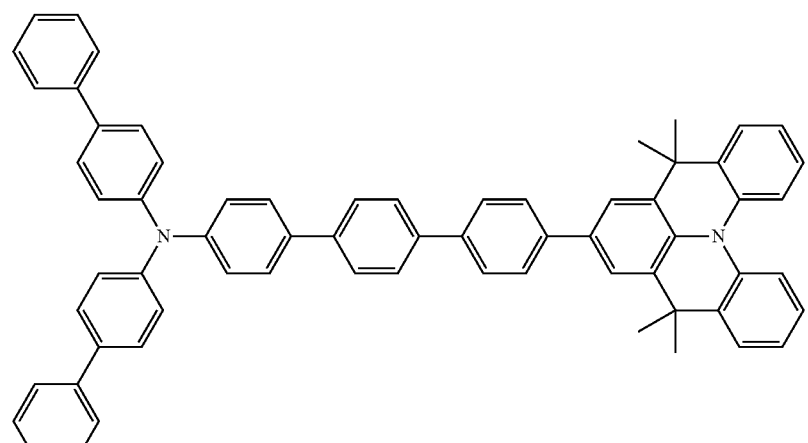 |

TABLE 4-continued
| No. | Structure |
|---|---|
| 43 | 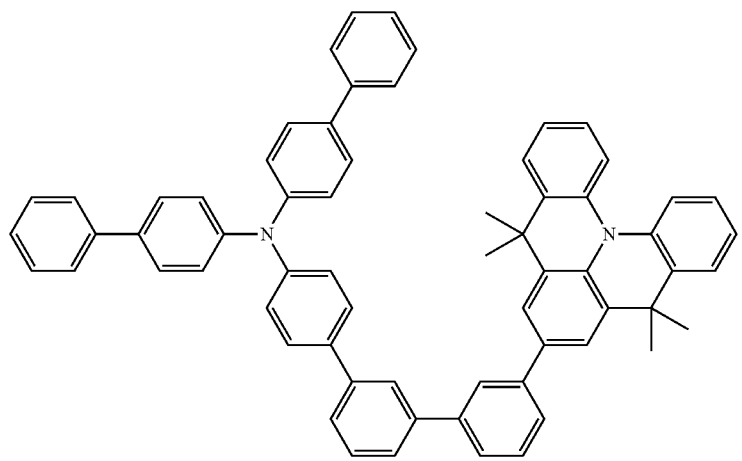 [SMILES: CC1(C)c2ccccc2N2c3ccccc3C(C)(C)c3cc(-c4cccc(-c5cccc(-c6ccc(N(c7ccc(-c8ccccc8)cc7)c7ccc(-c8ccccc8)cc7)cc6)c5)c4)cc1c32] |
| 44 | 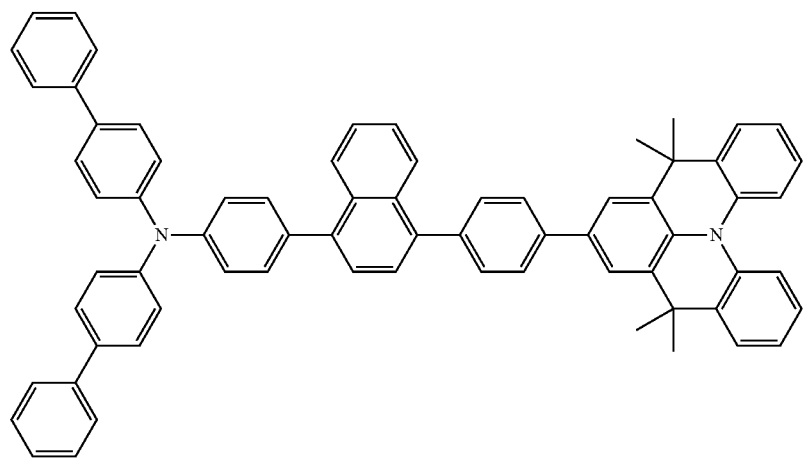 [SMILES: CC1(C)c2ccccc2N2c3ccccc3C(C)(C)c3cc(-c4ccc(-c5ccc(-c6ccc(N(c7ccc(-c8ccccc8)cc7)c7ccc(-c8ccccc8)cc7)cc6)c6ccccc56)cc4)cc1c32] |
| 45 | 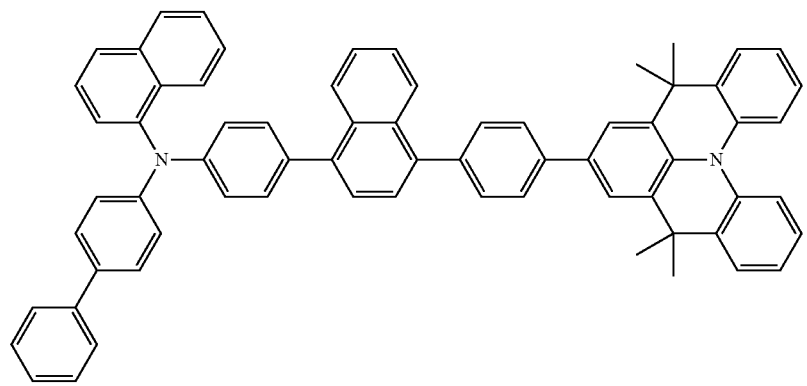 [SMILES: CC1(C)c2ccccc2N2c3ccccc3C(C)(C)c3cc(-c4ccc(-c5ccc(-c6ccc(N(c7ccc(-c8ccccc8)cc7)c7cccc8ccccc78)cc6)c6ccccc56)cc4)cc1c32] |

TABLE 4-continued

| No. | Structure |
|---|---|
| 46 | 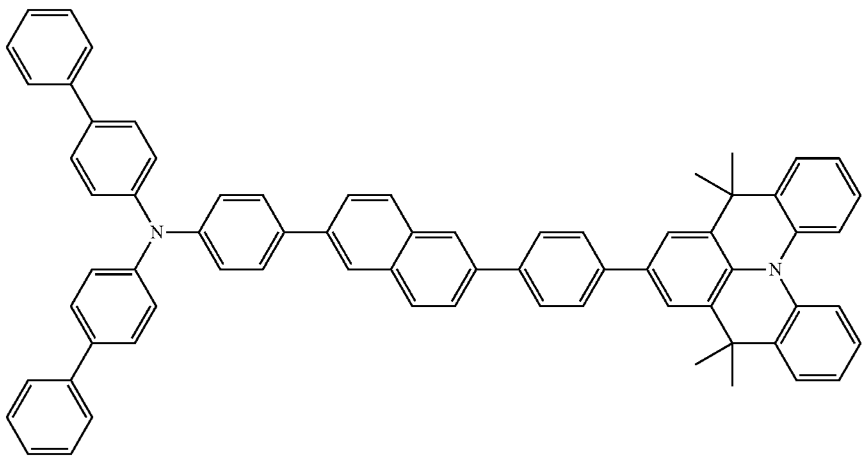 [SMILES: CC1(C)c2ccccc2N2c3ccccc3C(C)(C)c3cc(-c4ccc(-c5ccc6cc(-c7ccc(N(c8ccc(-c9ccccc9)cc8)c8ccc(-c9ccccc9)cc8)cc7)ccc6c5)cc4)cc1c32] |
| 47 | 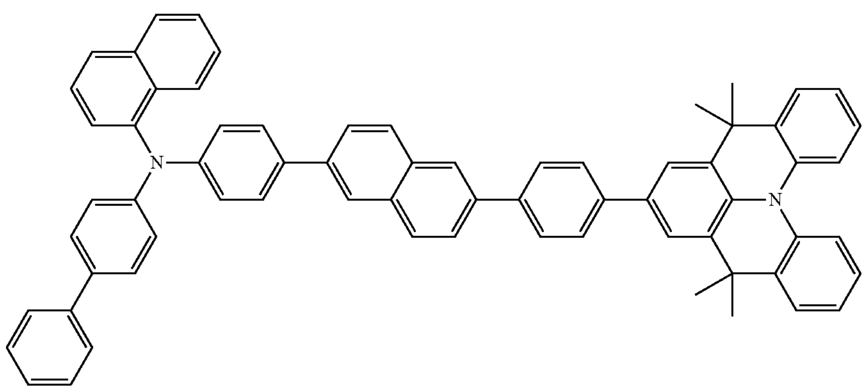 [SMILES: CC1(C)c2ccccc2N2c3ccccc3C(C)(C)c3cc(-c4ccc(-c5ccc6cc(-c7ccc(N(c8ccc(-c9ccccc9)cc8)c8cccc9ccccc89)cc7)ccc6c5)cc4)cc1c32] |
| 48 | 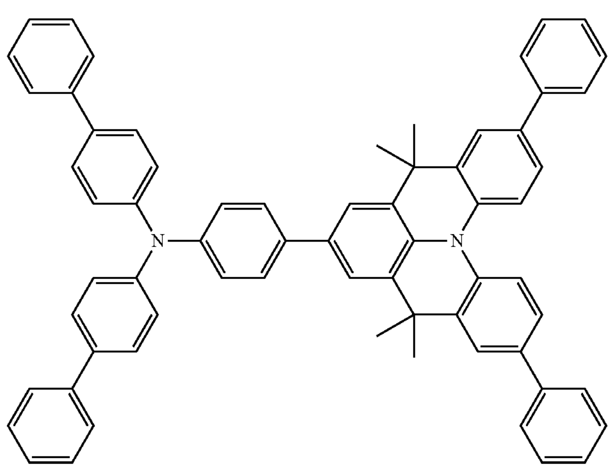 [SMILES: CC1(C)c2cc(-c3ccccc3)ccc2N2c3ccc(-c4ccccc4)cc3C(C)(C)c3cc(-c4ccc(N(c5ccc(-c6ccccc6)cc5)c5ccc(-c6ccccc6)cc5)cc4)cc1c32] |

TABLE 4-continued
| No. | Structure |
|---|---|
| 49 | 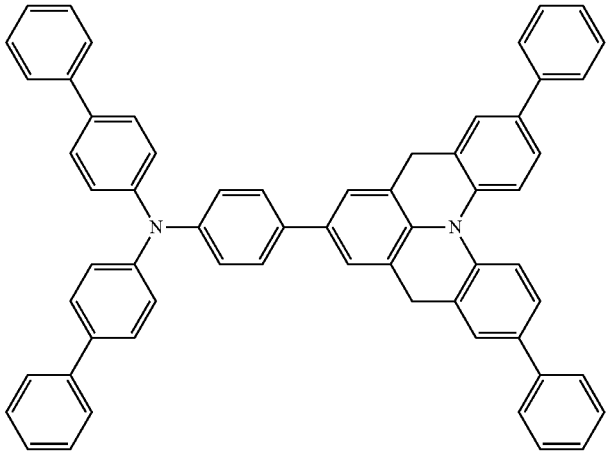 [SMILES: c1ccc(-c2ccc(N(c3ccc(-c4ccccc4)cc3)c3ccc(-c4cc5c6c(c4)Cc4cc(-c7ccccc7)ccc4N6c4ccc(-c6ccccc6)cc4C5)cc3)cc2)cc1] |
| 50 | 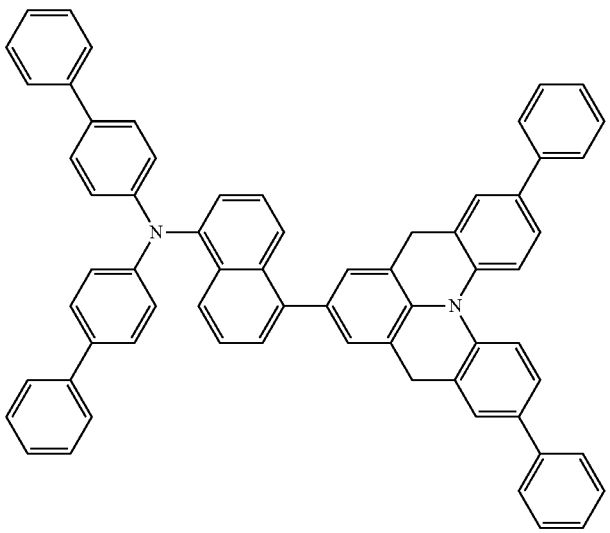 [SMILES: c1ccc(-c2ccc(N(c3ccc(-c4ccccc4)cc3)c3cccc4c(-c5cc6c7c(c5)Cc5cc(-c8ccccc8)ccc5N7c5ccc(-c7ccccc7)cc5C6)cccc34)cc2)cc1] |
| 51 | 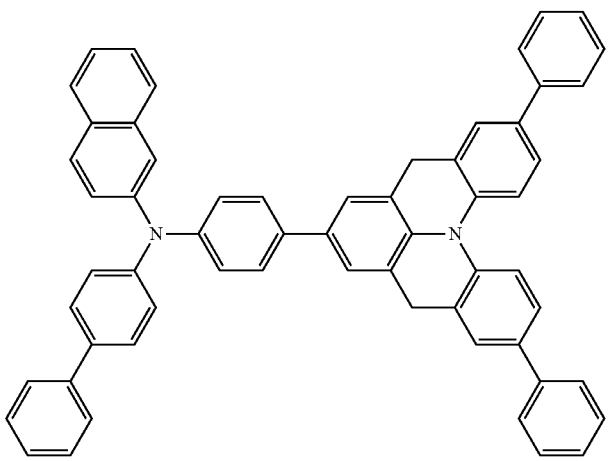 [SMILES: c1ccc(-c2ccc(N(c3ccc(-c4cc5c6c(c4)Cc4cc(-c7ccccc7)ccc4N6c4ccc(-c6ccccc6)cc4C5)cc3)c3ccc4ccccc4c3)cc2)cc1] |

TABLE 4-continued
| No. | Structure |
|---|---|
| 52 | 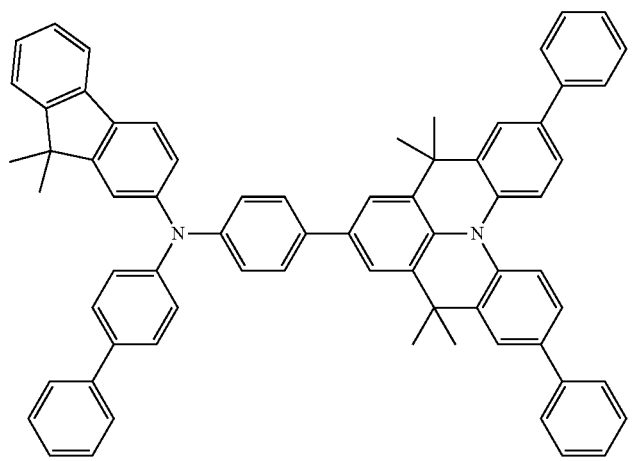 [SMILES: CC1(C)c2ccccc2-c2ccc(N(c3ccc(-c4ccccc4)cc3)c3ccc(-c4cc5c6c(c4)C(C)(C)c4cc(-c7ccccc7)ccc4N6c4ccc(-c6ccccc6)cc4C5(C)C)cc3)cc21] |
| 53 | 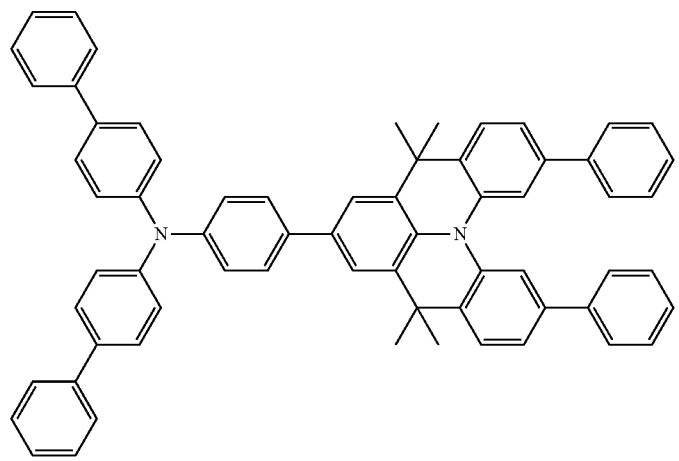 [SMILES: CC1(C)c2ccc(-c3ccccc3)cc2N2c3cc(-c4ccccc4)ccc3C(C)(C)c3cc(-c4ccc(N(c5ccc(-c6ccccc6)cc5)c5ccc(-c6ccccc6)cc5)cc4)cc1c32] |
| 54 | 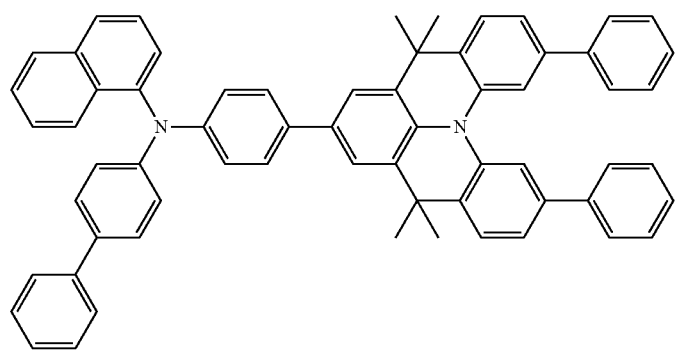 [SMILES: CC1(C)c2ccc(-c3ccccc3)cc2N2c3cc(-c4ccccc4)ccc3C(C)(C)c3cc(-c4ccc(N(c5ccc(-c6ccccc6)cc5)c5cccc6ccccc56)cc4)cc1c32] |

TABLE 4-continued
| No. | Structure |
|---|---|
| 55 | 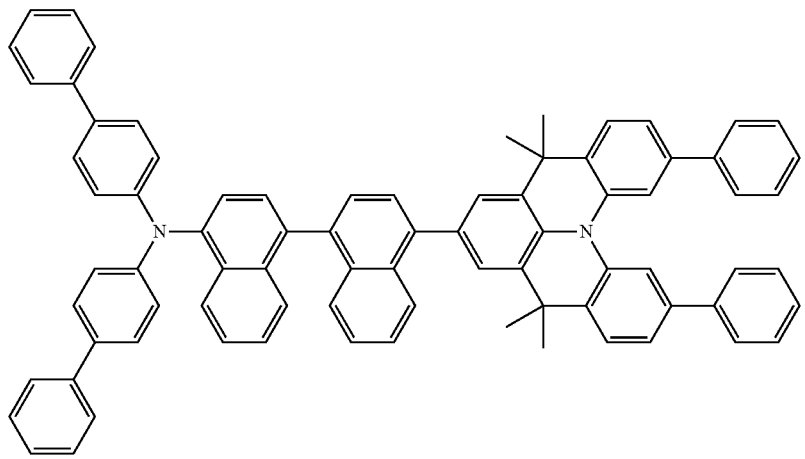 [SMILES: CC1(C)c2ccc(-c3ccccc3)cc2N2c3cc(-c4ccccc4)ccc3C(C)(C)c3cc(-c4ccc(-c5ccc(N(c6ccc(-c7ccccc7)cc6)c6ccc(-c7ccccc7)cc6)c6ccccc56)c5ccccc45)cc1c32] |
| 56 | 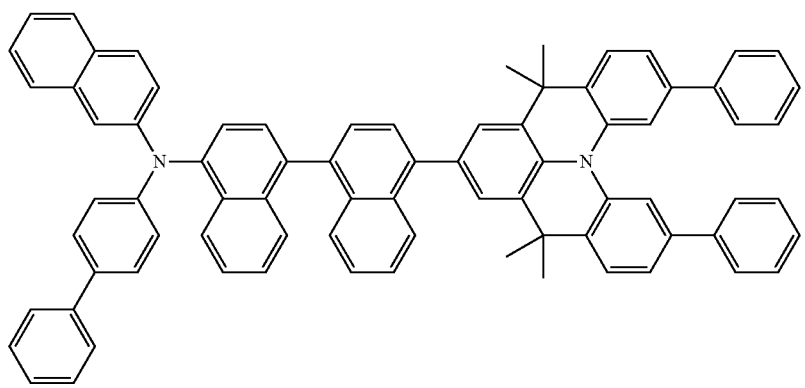 [SMILES: CC1(C)c2ccc(-c3ccccc3)cc2N2c3cc(-c4ccccc4)ccc3C(C)(C)c3cc(-c4ccc(-c5ccc(N(c6ccc(-c7ccccc7)cc6)c6ccc7ccccc7c6)c6ccccc56)c5ccccc45)cc1c32] |
| 57 | 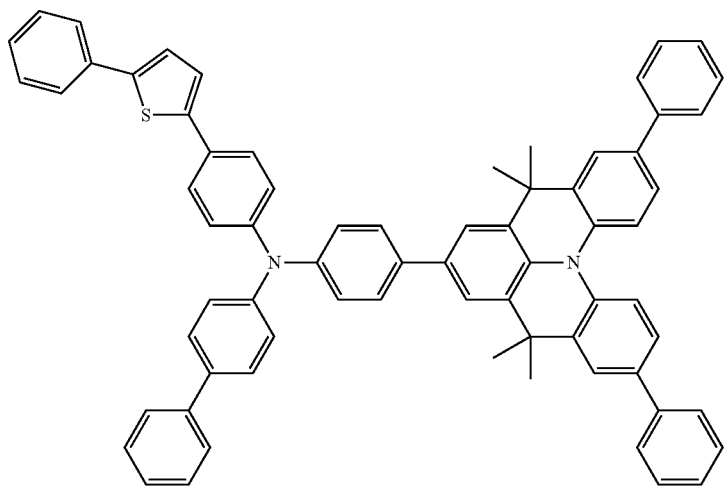 [SMILES: CC1(C)c2cc(-c3ccccc3)ccc2N2c3ccc(-c4ccccc4)cc3C(C)(C)c3cc(-c4ccc(N(c5ccc(-c6ccccc6)cc5)c5ccc(-c6ccc(-c7ccccc7)s6)cc5)cc4)cc1c32] |

TABLE 4-continued

| No. | Structure |
|---|---|
| 58 | 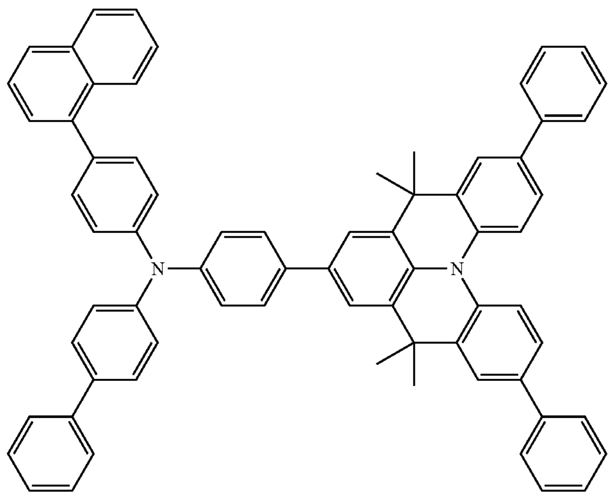 [SMILES: CC1(C)c2cc(-c3ccccc3)ccc2N2c3ccc(-c4ccccc4)cc3C(C)(C)c3cc(-c4ccc(N(c5ccc(-c6ccccc6)cc5)c5ccc(-c6cccc7ccccc67)cc5)cc4)cc1c32] |
| 59 | 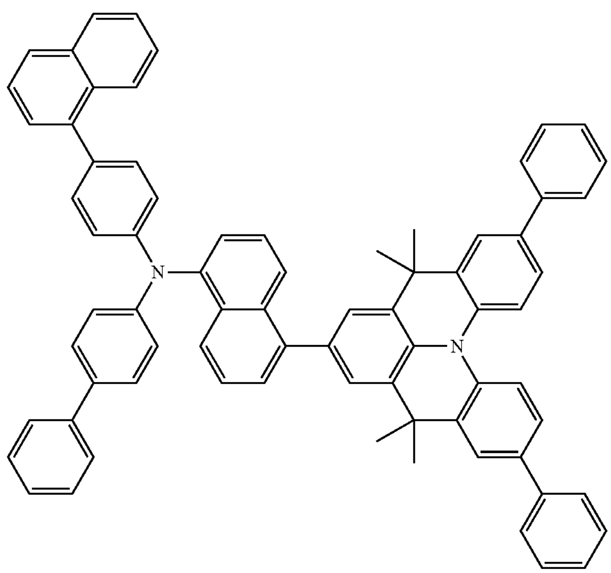 [SMILES: CC1(C)c2cc(-c3ccccc3)ccc2N2c3ccc(-c4ccccc4)cc3C(C)(C)c3cc(-c4cccc5c(N(c6ccc(-c7ccccc7)cc6)c6ccc(-c7cccc8ccccc78)cc6)cccc45)cc1c32] |
| 60 | 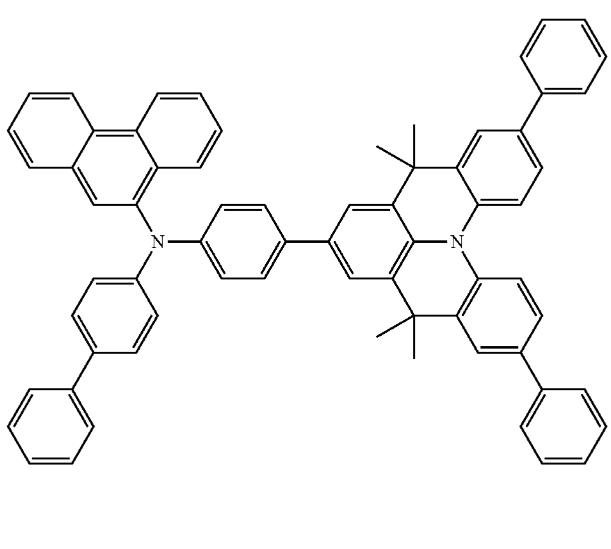 [SMILES: CC1(C)c2cc(-c3ccccc3)ccc2N2c3ccc(-c4ccccc4)cc3C(C)(C)c3cc(-c4ccc(N(c5ccc(-c6ccccc6)cc5)c5cc6ccccc6c6ccccc56)cc4)cc1c32] |

TABLE 4-continued
| No. | Structure |
|---|---|
| 61 | 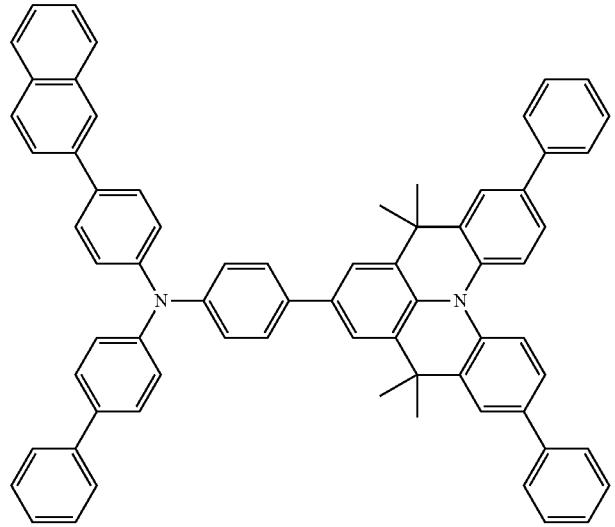 [SMILES: CC1(C)c2cc(-c3ccccc3)ccc2N2c3ccc(-c4ccccc4)cc3C(C)(C)c3cc(-c4ccc(N(c5ccc(-c6ccccc6)cc5)c5ccc(-c6ccc7ccccc7c6)cc5)cc4)cc1c32] |
| 62 | 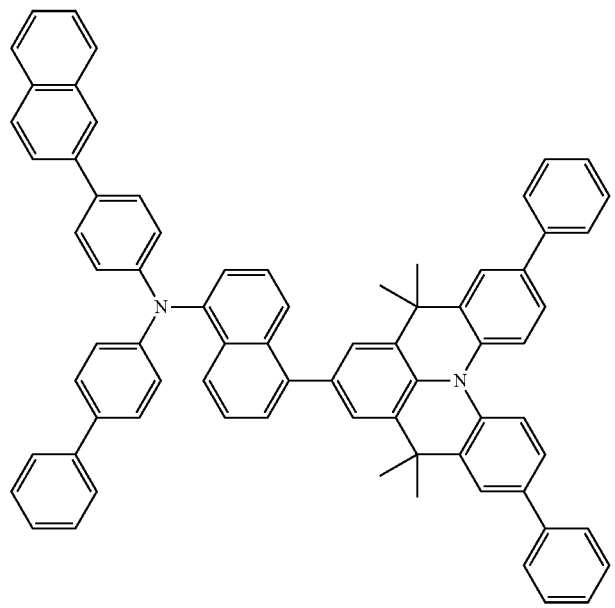 [SMILES: CC1(C)c2cc(-c3ccccc3)ccc2N2c3ccc(-c4ccccc4)cc3C(C)(C)c3cc(-c4cccc5c(N(c6ccc(-c7ccccc7)cc6)c6ccc(-c7ccc8ccccc8c7)cc6)cccc45)cc1c32] |
| 63 | 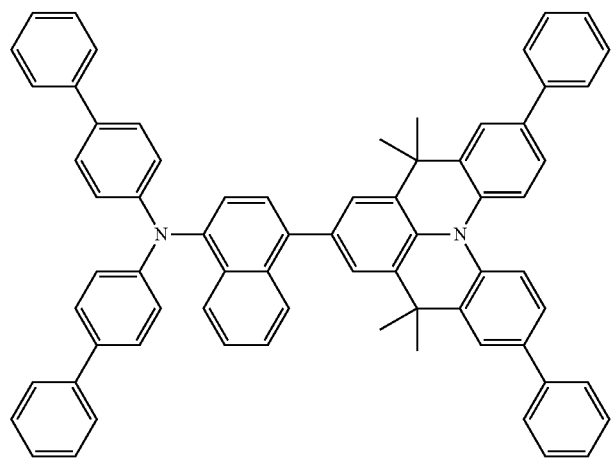 [SMILES: CC1(C)c2cc(-c3ccccc3)ccc2N2c3ccc(-c4ccccc4)cc3C(C)(C)c3cc(-c4ccc(N(c5ccc(-c6ccccc6)cc5)c5ccc(-c6ccccc6)cc5)c5ccccc45)cc1c32] |

TABLE 4-continued
| No. | Structure |
| --- | --- |
| 64 | 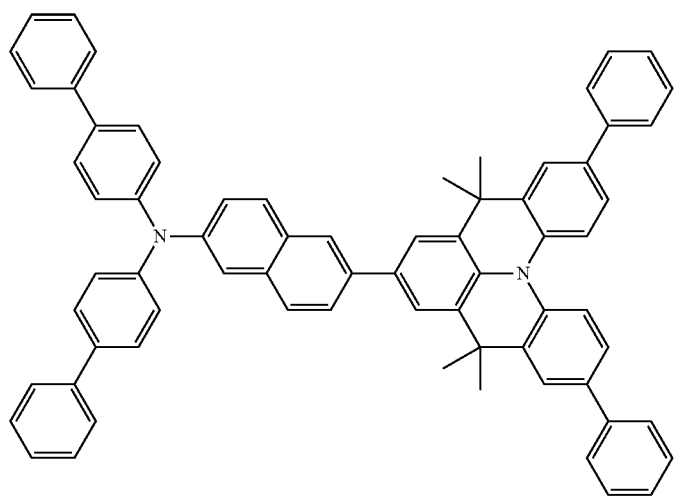 [SMILES: CC1(C)c2cc(-c3ccccc3)ccc2N2c3ccc(-c4ccccc4)cc3C(C)(C)c3cc(-c4ccc5cc(N(c6ccc(-c7ccccc7)cc6)c6ccc(-c7ccccc7)cc6)ccc5c4)cc1c32] |
| 65 | 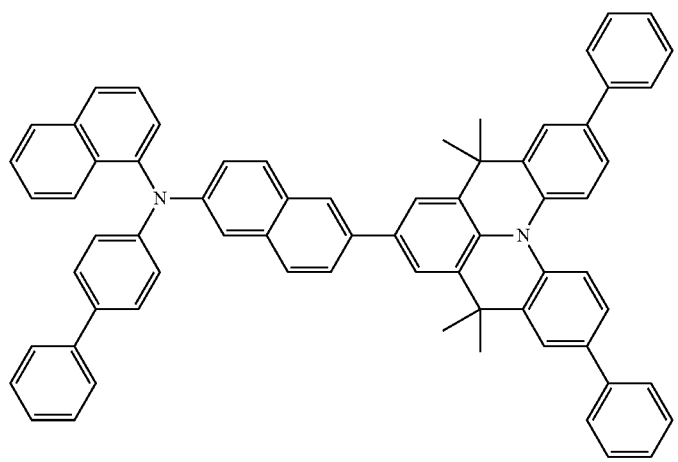 [SMILES: CC1(C)c2cc(-c3ccccc3)ccc2N2c3ccc(-c4ccccc4)cc3C(C)(C)c3cc(-c4ccc5cc(N(c6ccc(-c7ccccc7)cc6)c6cccc7ccccc67)ccc5c4)cc1c32] |
| 66 | 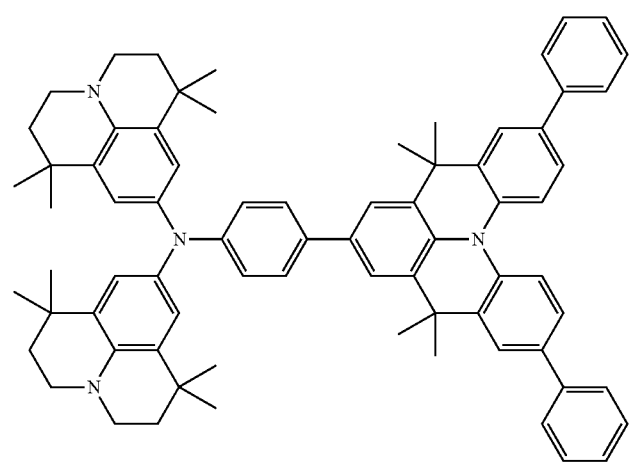 [SMILES: CC1(C)CCN2CCC(C)(C)c3cc(N(c4ccc(-c5cc6c7c(c5)C(C)(C)c5cc(-c8ccccc8)ccc5N7c5ccc(-c7ccccc7)cc5C6(C)C)cc4)c4cc5c6c(c4)C(C)(C)CCN6CCC5(C)C)cc1c32] |

TABLE 4-continued
| No. | Structure |
|---|---|
| 67 | 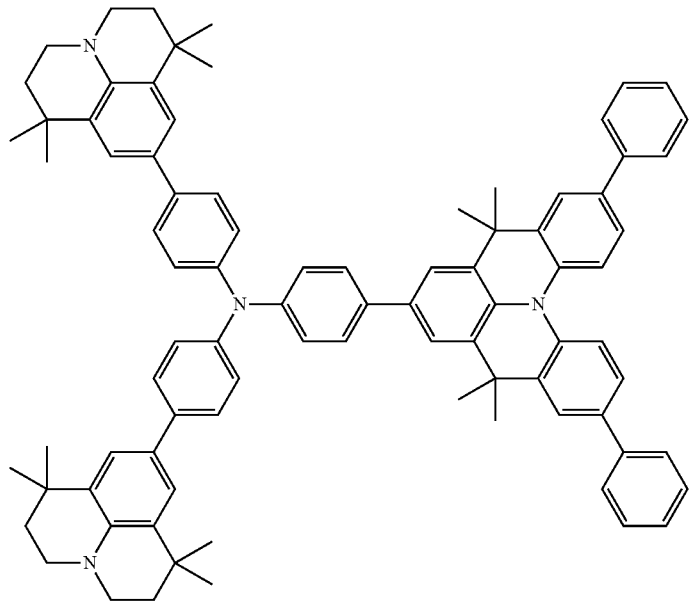 [SMILES: CC1(C)CCN2CCC(C)(C)c3cc(-c4ccc(N(c5ccc(-c6cc7c8c(c6)C(C)(C)CCN8CCC7(C)C)cc5)c5ccc(-c6cc7c8c(c6)C(C)(C)c6cc(-c9ccccc9)ccc6N8c6ccc(-c8ccccc8)cc6C7(C)C)cc5)cc4)cc1c32] |
| 68 | 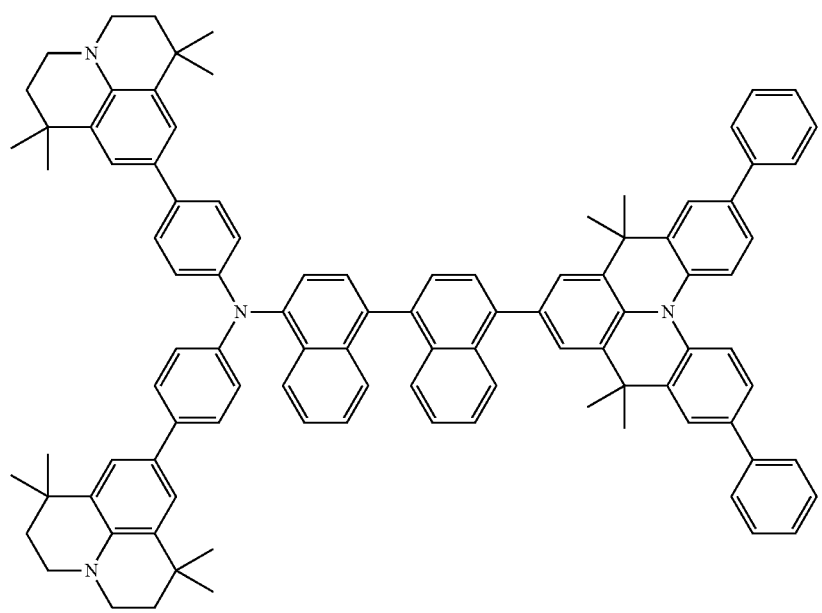 [SMILES: CC1(C)CCN2CCC(C)(C)c3cc(-c4ccc(N(c5ccc(-c6cc7c8c(c6)C(C)(C)CCN8CCC7(C)C)cc5)c5ccc(-c6ccc(-c7cc8c9c(c7)C(C)(C)c7cc(-c%10ccccc%10)ccc7N9c7ccc(-c9ccccc9)cc7C8(C)C)c7ccccc67)c6ccccc56)cc4)cc1c32] |

TABLE 4-continued
| No. | Structure |
|---|---|
| 69 | 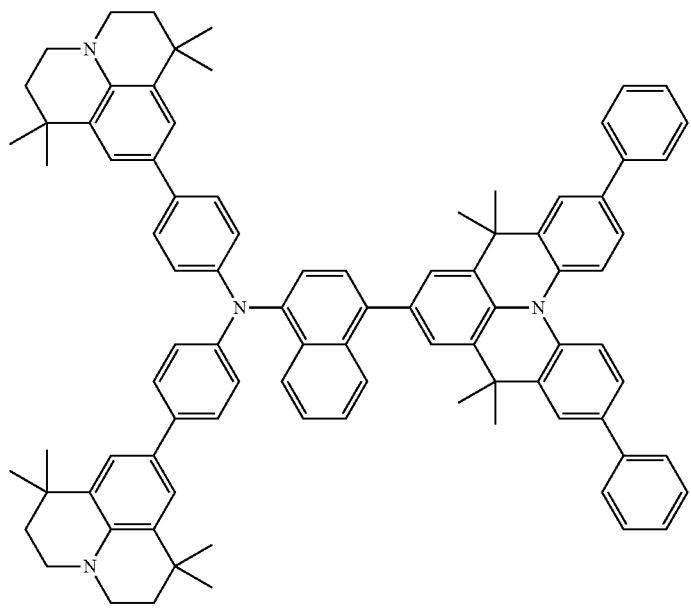 [SMILES: CC1(C)CCN2CCC(C)(C)c3cc(-c4ccc(N(c5ccc(-c6cc7c8c(c6)C(C)(C)CCN8CCC7(C)C)cc5)c5ccc(-c6cc7c8c(c6)C(C)(C)c6cc(-c9ccccc9)ccc6N8c6ccc(-c8ccccc8)cc6C7(C)C)c6ccccc56)cc4)cc1c32] |
| 70 | 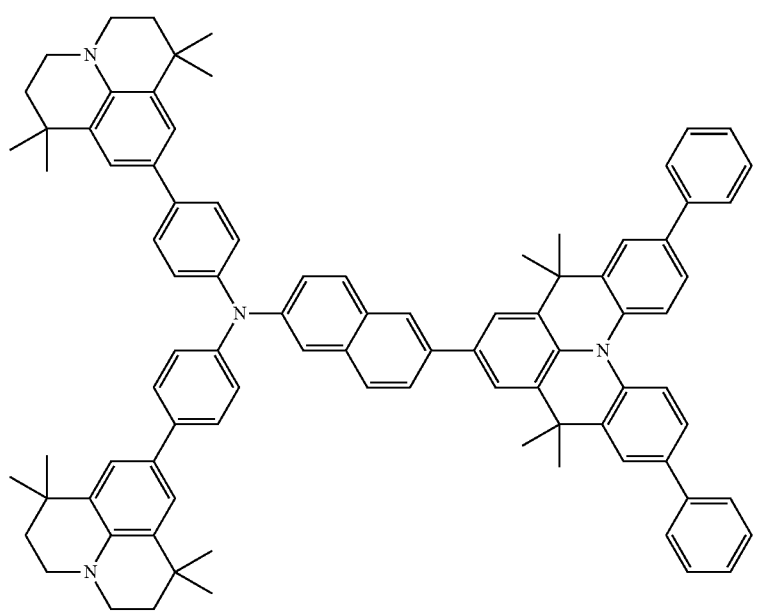 [SMILES: CC1(C)CCN2CCC(C)(C)c3cc(-c4ccc(N(c5ccc(-c6cc7c8c(c6)C(C)(C)CCN8CCC7(C)C)cc5)c5ccc6cc(-c7cc8c9c(c7)C(C)(C)c7cc(-c%10ccccc%10)ccc7N9c7ccc(-c9ccccc9)cc7C8(C)C)ccc6c5)cc4)cc1c32] |

TABLE 4-continued
| No. | Structure |
|---|---|
| 71 | 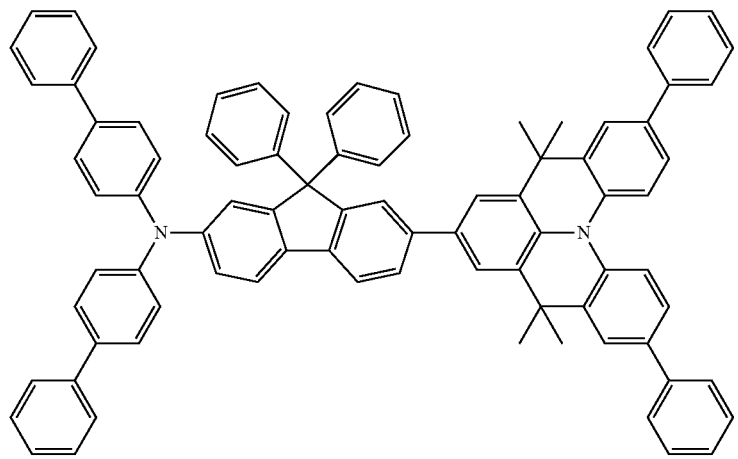 [SMILES: CC1(C)c2cc(-c3ccccc3)ccc2N2c3ccc(-c4ccccc4)cc3C(C)(C)c3cc(-c4ccc5c(c4)C(c4ccccc4)(c4ccccc4)c4cc(N(c6ccc(-c7ccccc7)cc6)c6ccc(-c7ccccc7)cc6)ccc4-5)cc1c32] |
| 72 | 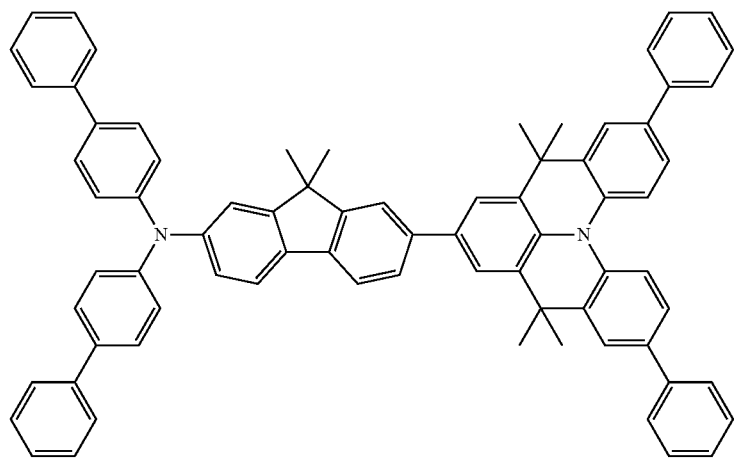 |
| 73 | 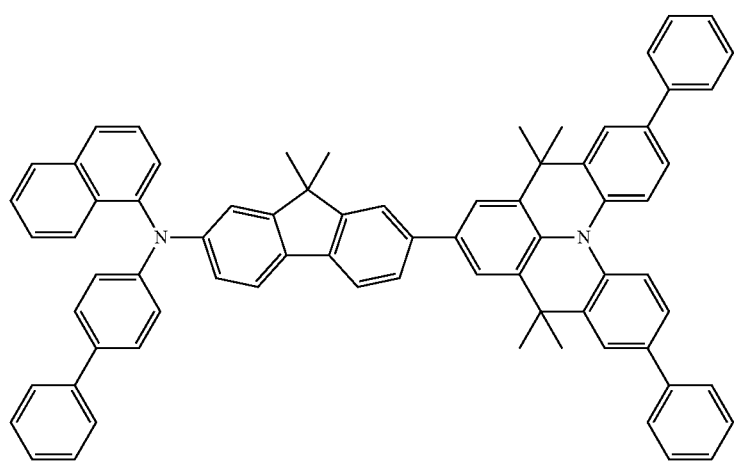 [SMILES: CC1(C)c2cc(-c3cc4c5c(c3)C(C)(C)c3cc(-c6ccccc6)ccc3N5c3ccc(-c5ccccc5)cc3C4(C)C)ccc2-c2ccc(N(c3ccc(-c4ccccc4)cc3)c3cccc4ccccc34)cc21] |

TABLE 4-continued
| No. | Structure |
|---|---|
| 74 | 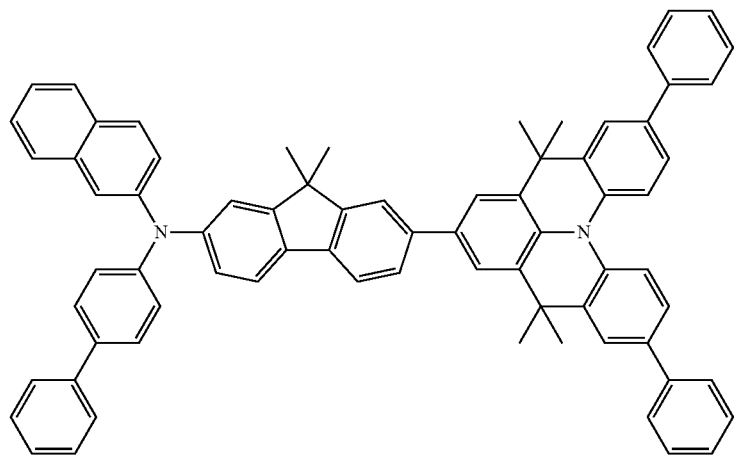 [SMILES: CC1(C)c2cc(-c3cc4c5c(c3)C(C)(C)c3cc(-c6ccccc6)ccc3N5c3ccc(-c5ccccc5)cc3C4(C)C)ccc2-c2ccc(N(c3ccc(-c4ccccc4)cc3)c3ccc4ccccc4c3)cc21] |
| 75 | 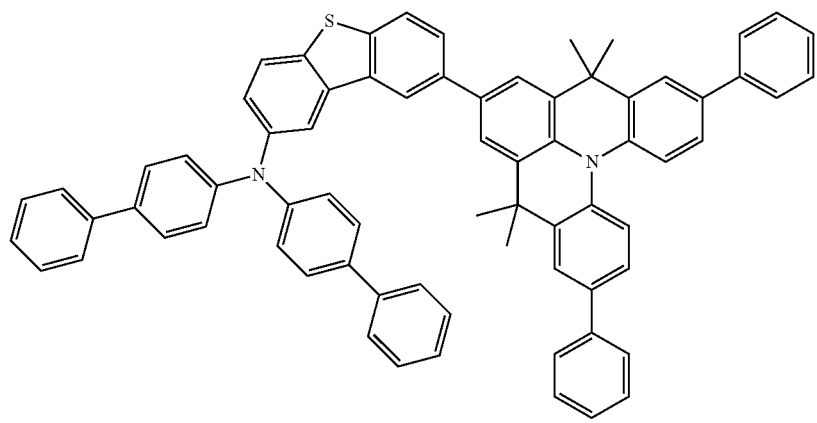 [SMILES: CC1(C)c2cc(-c3ccccc3)ccc2N2c3ccc(-c4ccccc4)cc3C(C)(C)c3cc(-c4ccc5sc6ccc(N(c7ccc(-c8ccccc8)cc7)c7ccc(-c8ccccc8)cc7)cc6c5c4)cc1c32] |
| 76 | 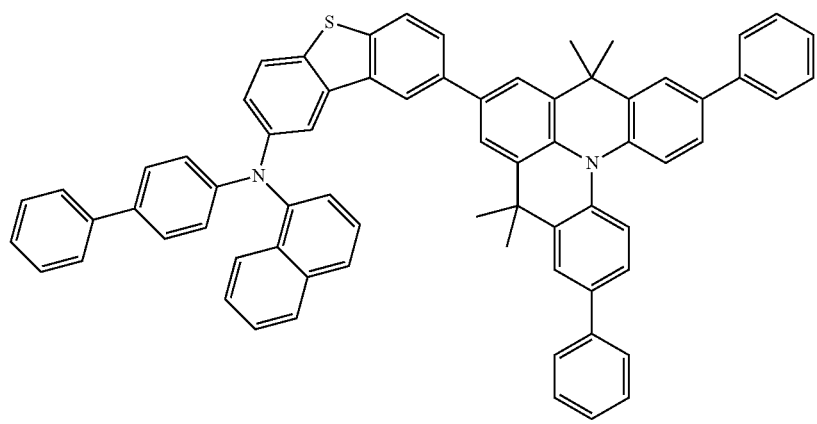 [SMILES: CC1(C)c2cc(-c3ccccc3)ccc2N2c3ccc(-c4ccccc4)cc3C(C)(C)c3cc(-c4ccc5sc6ccc(N(c7ccc(-c8ccccc8)cc7)c7cccc8ccccc78)cc6c5c4)cc1c32] |

TABLE 4-continued
| No. | Structure |
|---|---|
| 77 | 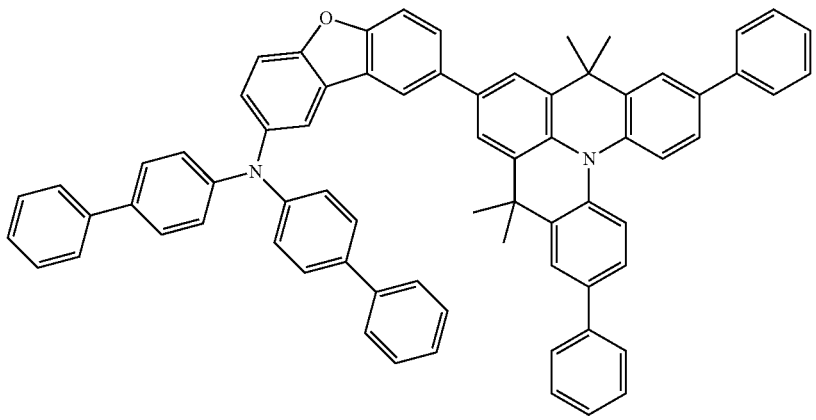 [SMILES: CC1(C)c2cc(-c3ccccc3)ccc2N2c3ccc(-c4ccccc4)cc3C(C)(C)c3cc(-c4ccc5oc6ccc(N(c7ccc(-c8ccccc8)cc7)c7ccc(-c8ccccc8)cc7)cc6c5c4)cc1c32] |
| 78 | 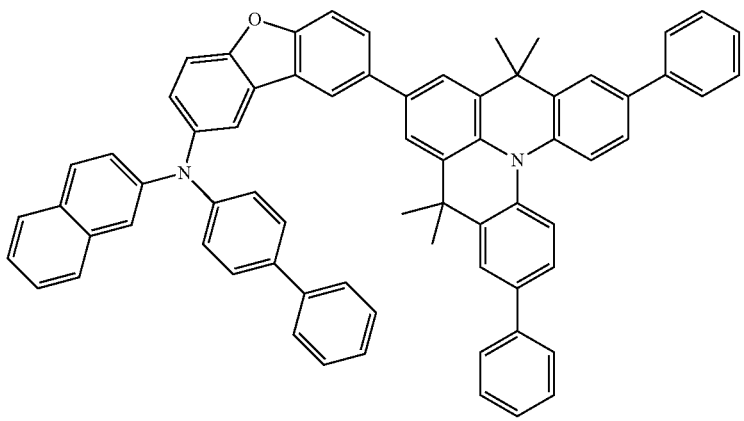 [SMILES: CC1(C)c2cc(-c3ccccc3)ccc2N2c3ccc(-c4ccccc4)cc3C(C)(C)c3cc(-c4ccc5oc6ccc(N(c7ccc(-c8ccccc8)cc7)c7ccc8ccccc8c7)cc6c5c4)cc1c32] |
| 79 | 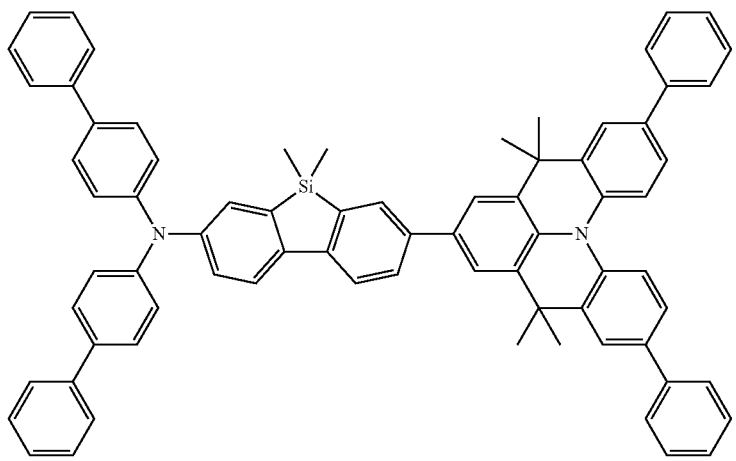 |

TABLE 4-continued
| No. | Structure |
|---|---|
| 80 | 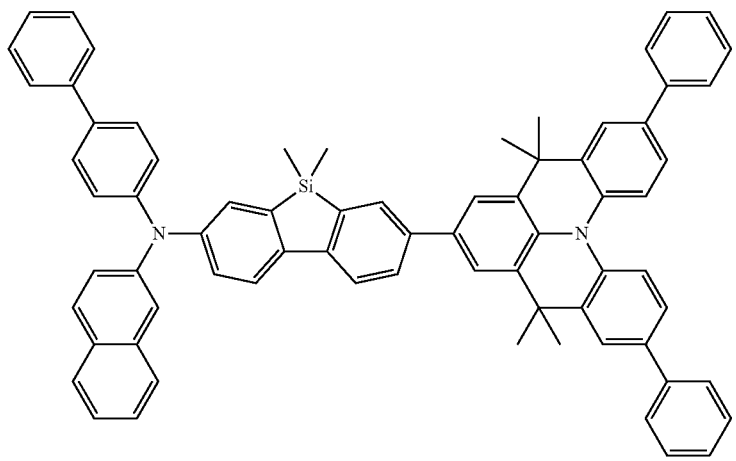 [SMILES: CC1(C)c2cc(-c3ccccc3)ccc2N2c3ccc(-c4ccccc4)cc3C(C)(C)c3cc(-c4ccc5c(c4)[Si](C)(C)c4cc(N(c6ccc(-c7ccccc7)cc6)c6ccc7ccccc7c6)ccc4-5)cc1c32] |
| 81 | 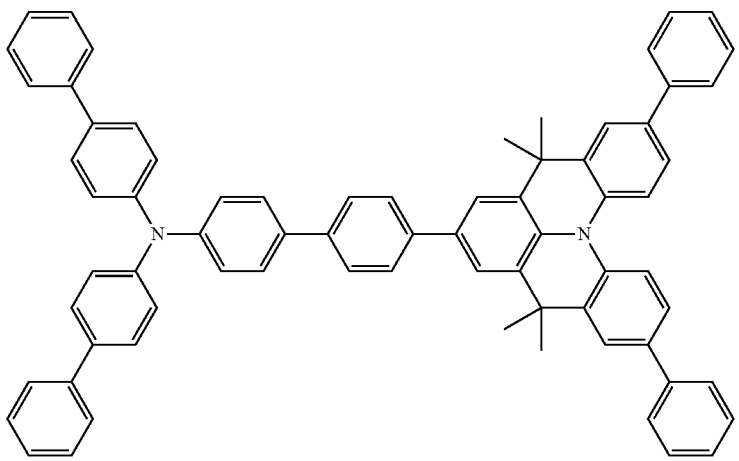 [SMILES: CC1(C)c2cc(-c3ccccc3)ccc2N2c3ccc(-c4ccccc4)cc3C(C)(C)c3cc(-c4ccc(-c5ccc(N(c6ccc(-c7ccccc7)cc6)c6ccc(-c7ccccc7)cc6)cc5)cc4)cc1c32] |
| 82 | 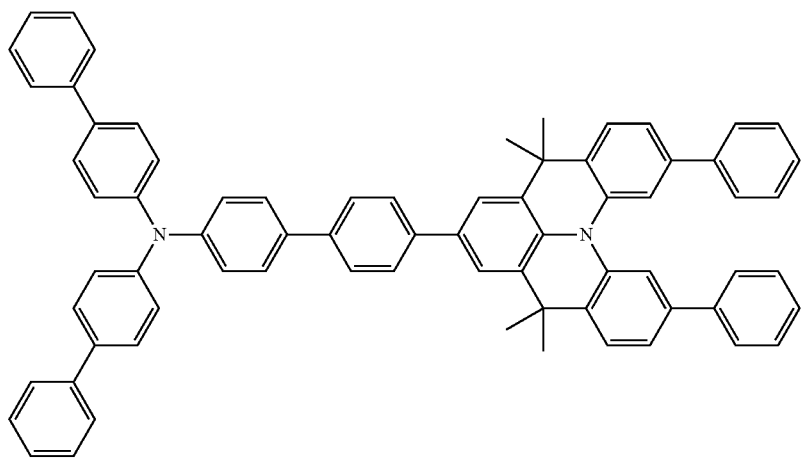 [SMILES: CC1(C)c2ccc(-c3ccccc3)cc2N2c3cc(-c4ccccc4)ccc3C(C)(C)c3cc(-c4ccc(-c5ccc(N(c6ccc(-c7ccccc7)cc6)c6ccc(-c7ccccc7)cc6)cc5)cc4)cc1c32] |

TABLE 4-continued
| No. | Structure |
|---|---|
| 83 | 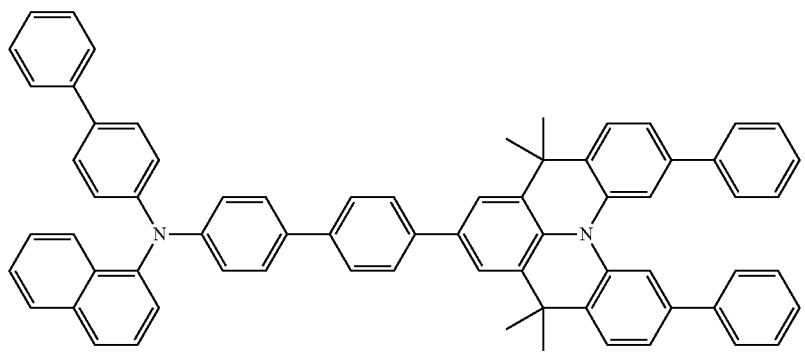 [SMILES: CC1(C)c2ccc(-c3ccccc3)cc2N2c3cc(-c4ccccc4)ccc3C(C)(C)c3cc(-c4ccc(-c5ccc(N(c6ccc(-c7ccccc7)cc6)c6cccc7ccccc67)cc5)cc4)cc1c32] |
| 84 | 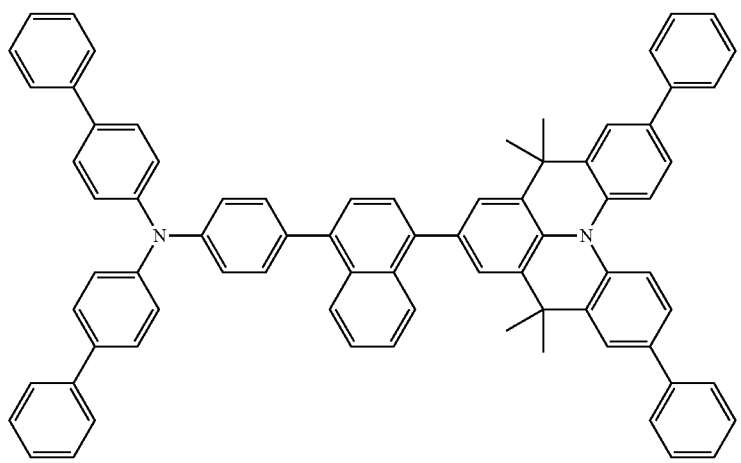 [SMILES: CC1(C)c2cc(-c3ccccc3)ccc2N2c3ccc(-c4ccccc4)cc3C(C)(C)c3cc(-c4ccc(-c5ccc(N(c6ccc(-c7ccccc7)cc6)c6ccc(-c7ccccc7)cc6)cc5)c5ccccc45)cc1c32] |
| 85 | 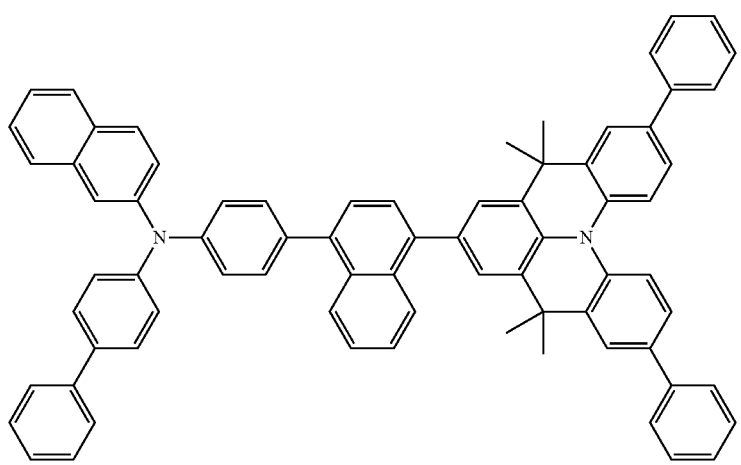 [SMILES: CC1(C)c2cc(-c3ccccc3)ccc2N2c3ccc(-c4ccccc4)cc3C(C)(C)c3cc(-c4ccc(-c5ccc(N(c6ccc(-c7ccccc7)cc6)c6ccc7ccccc7c6)cc5)c5ccccc45)cc1c32] |

TABLE 4-continued
| No. | Structure |
|---|---|
| 86 | 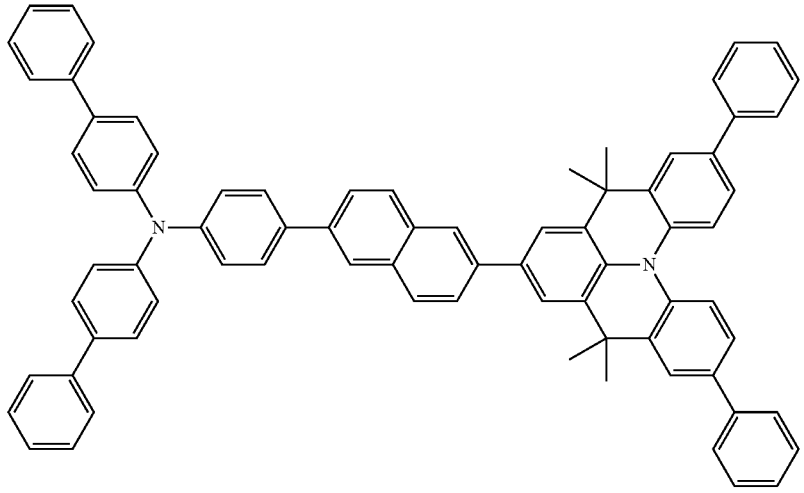 [SMILES: CC1(C)c2cc(-c3ccccc3)ccc2N2c3ccc(-c4ccccc4)cc3C(C)(C)c3cc(-c4ccc5cc(-c6ccc(N(c7ccc(-c8ccccc8)cc7)c7ccc(-c8ccccc8)cc7)cc6)ccc5c4)cc1c32] |
| 87 | 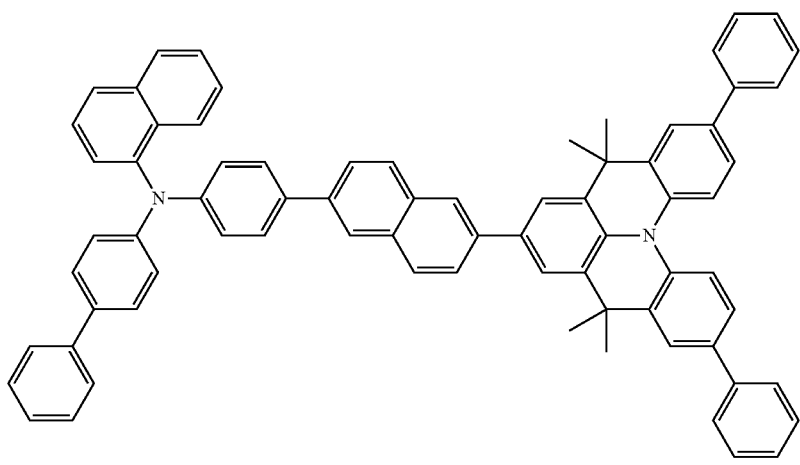 [SMILES: CC1(C)c2cc(-c3ccccc3)ccc2N2c3ccc(-c4ccccc4)cc3C(C)(C)c3cc(-c4ccc5cc(-c6ccc(N(c7ccc(-c8ccccc8)cc7)c7cccc8ccccc78)cc6)ccc5c4)cc1c32] |
| 88 | 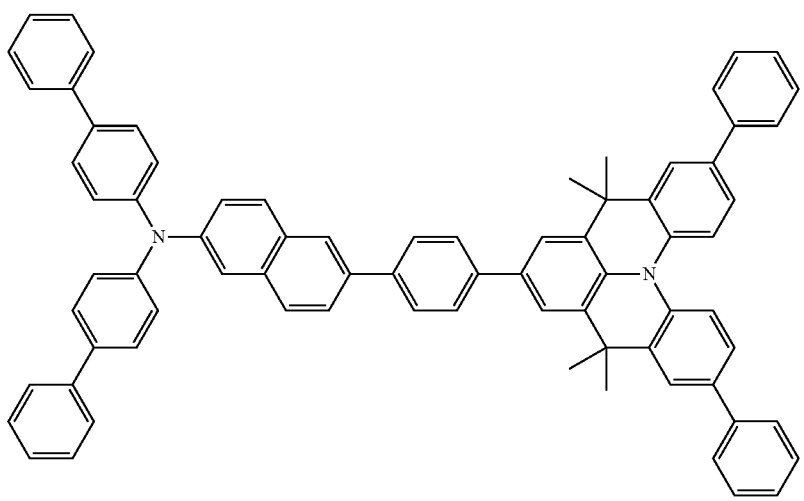 [SMILES: CC1(C)c2cc(-c3ccccc3)ccc2N2c3ccc(-c4ccccc4)cc3C(C)(C)c3cc(-c4ccc(-c5ccc6cc(N(c7ccc(-c8ccccc8)cc7)c7ccc(-c8ccccc8)cc7)ccc6c5)cc4)cc1c32] |

TABLE 4-continued
| No. | Structure |
|---|---|
| 89 | 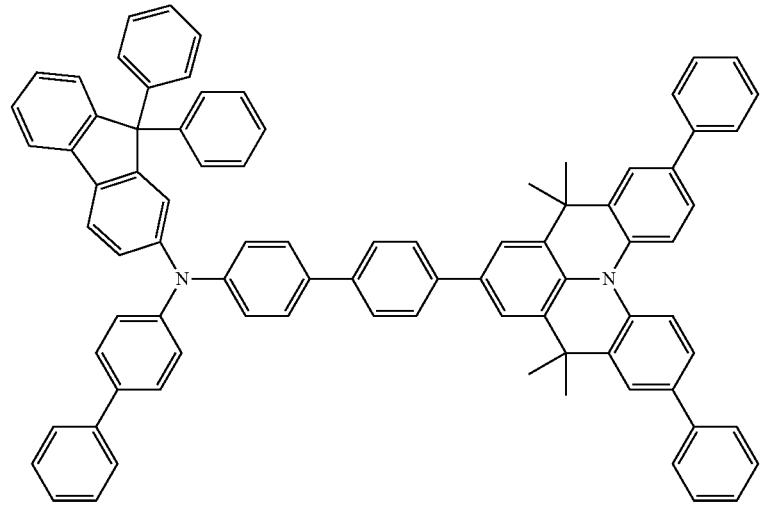 [SMILES: CC1(C)c2cc(-c3ccccc3)ccc2N2c3ccc(-c4ccccc4)cc3C(C)(C)c3cc(-c4ccc(-c5ccc(N(c6ccc(-c7ccccc7)cc6)c6ccc7c(c6)C(c6ccccc6)(c6ccccc6)c6ccccc6-7)cc5)cc4)cc1c32] |
| 90 | 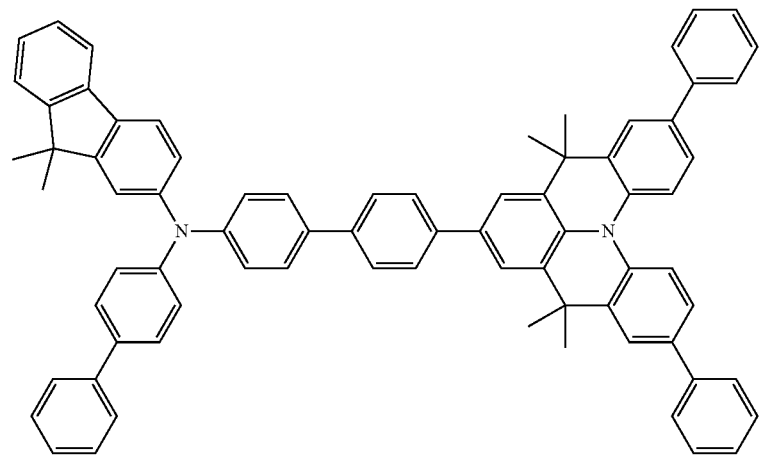 [SMILES: CC1(C)c2ccccc2-c2ccc(N(c3ccc(-c4ccccc4)cc3)c3ccc(-c4ccc(-c5cc6c7c(c5)C(C)(C)c5cc(-c8ccccc8)ccc5N7c5ccc(-c7ccccc7)cc5C6(C)C)cc4)cc3)cc21] |
| 91 | 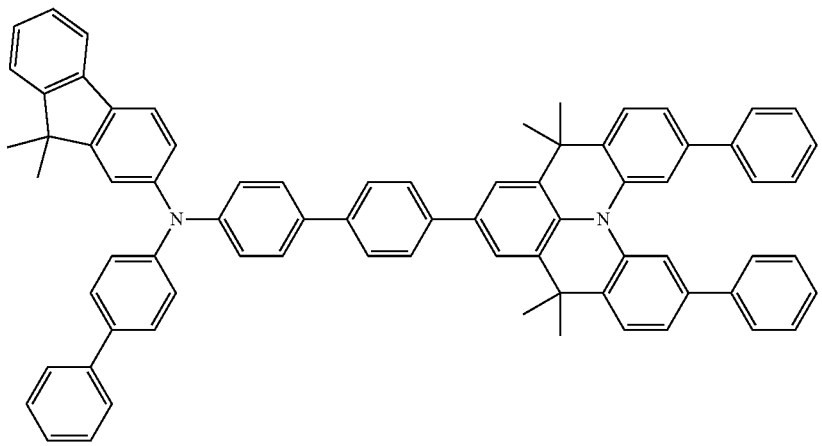 [SMILES: CC1(C)c2ccccc2-c2ccc(N(c3ccc(-c4ccccc4)cc3)c3ccc(-c4ccc(-c5cc6c7c(c5)C(C)(C)c5ccc(-c8ccccc8)cc5N7c5cc(-c7ccccc7)ccc5C6(C)C)cc4)cc3)cc21] |

TABLE 4-continued

| No. | Structure |
|---|---|
| 92 | 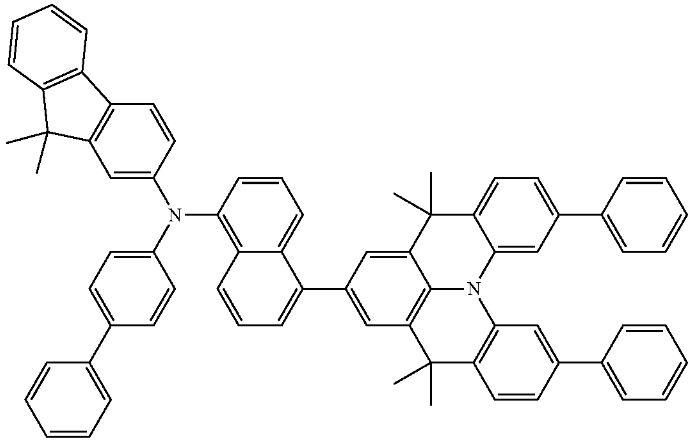 [SMILES: CC1(C)c2ccccc2-c2ccc(N(c3ccc(-c4ccccc4)cc3)c3cccc4c(-c5cc6c7c(c5)C(C)(C)c5ccc(-c8ccccc8)cc5N7c5cc(-c7ccccc7)ccc5C6(C)C)cccc34)cc21] |
| 93 | 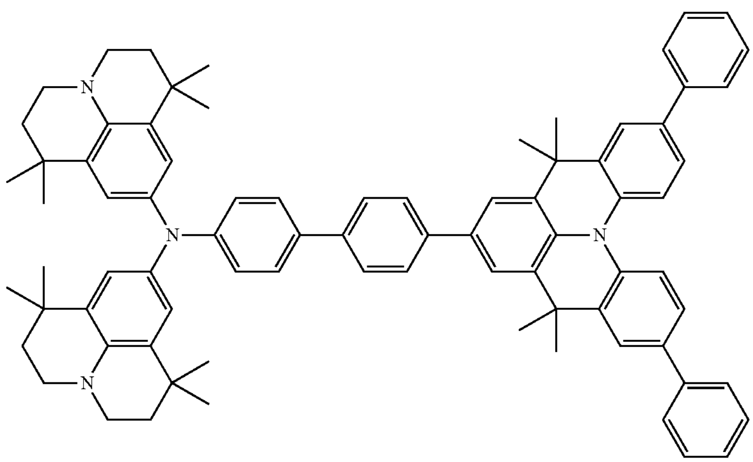 [SMILES: CC1(C)CCN2CCC(C)(C)c3cc(N(c4ccc(-c5ccc(-c6cc7c8c(c6)C(C)(C)c6cc(-c9ccccc9)ccc6N8c6ccc(-c8ccccc8)cc6C7(C)C)cc5)cc4)c4cc5c6c(c4)C(C)(C)CCN6CCC5(C)C)cc1c32] |
| 94 | 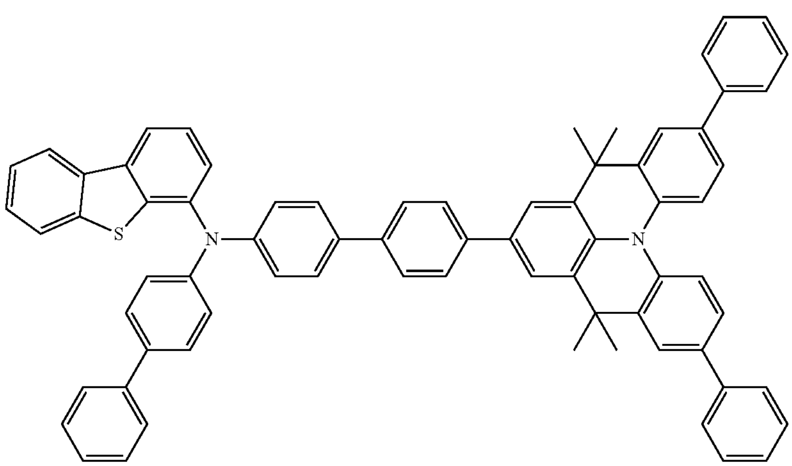 [SMILES: CC1(C)c2cc(-c3ccccc3)ccc2N2c3ccc(-c4ccccc4)cc3C(C)(C)c3cc(-c4ccc(-c5ccc(N(c6ccc(-c7ccccc7)cc6)c6cccc7c6sc6ccccc67)cc5)cc4)cc1c32] |

TABLE 4-continued
| No. | Structure |
|---|---|
| 95 | 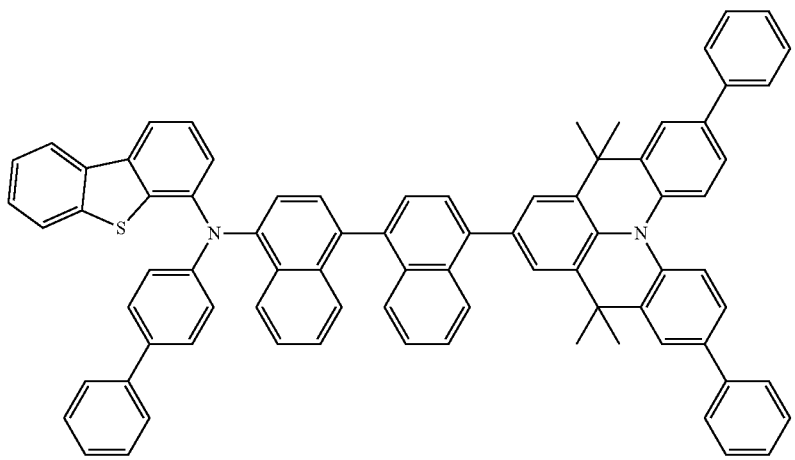 [SMILES: CC1(C)c2cc(-c3ccccc3)ccc2N2c3ccc(-c4ccccc4)cc3C(C)(C)c3cc(-c4ccc(-c5ccc(N(c6ccc(-c7ccccc7)cc6)c6cccc7c6sc6ccccc67)c6ccccc56)c5ccccc45)cc1c32] |
| 96 | 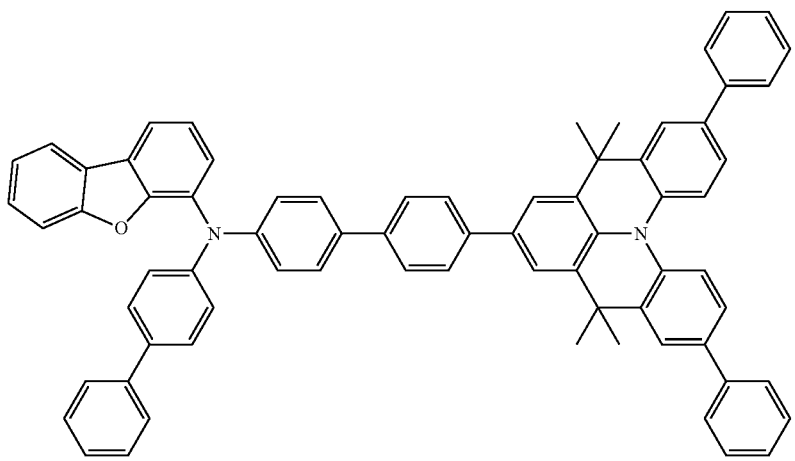 |
| 97 | 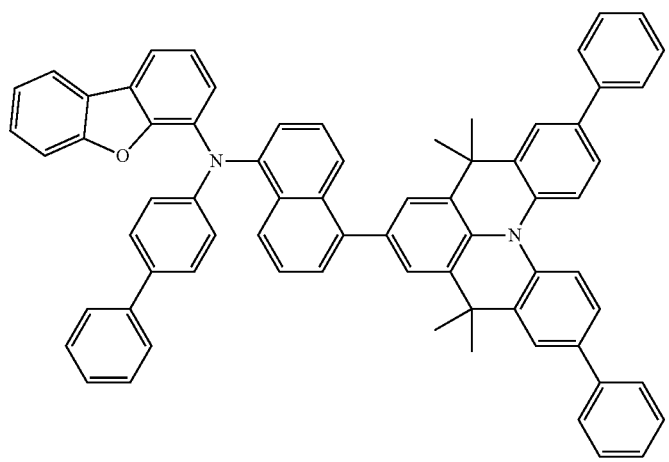 [SMILES: CC1(C)c2cc(-c3ccccc3)ccc2N2c3ccc(-c4ccccc4)cc3C(C)(C)c3cc(-c4cccc5c(N(c6ccc(-c7ccccc7)cc6)c6cccc7c6oc6ccccc67)cccc45)cc1c32] |

TABLE 4-continued
| No. | Structure |
|---|---|
| 98 | 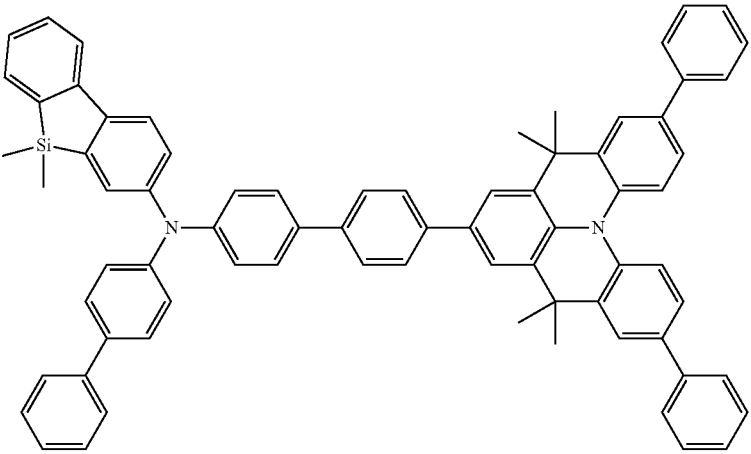 [SMILES: CC1(C)c2cc(-c3ccccc3)ccc2N2c3ccc(-c4ccccc4)cc3C(C)(C)c3cc(-c4ccc(-c5ccc(N(c6ccc(-c7ccccc7)cc6)c6ccc7c(c6)[Si](C)(C)c6ccccc6-7)cc5)cc4)cc1c32] |
| 99 | 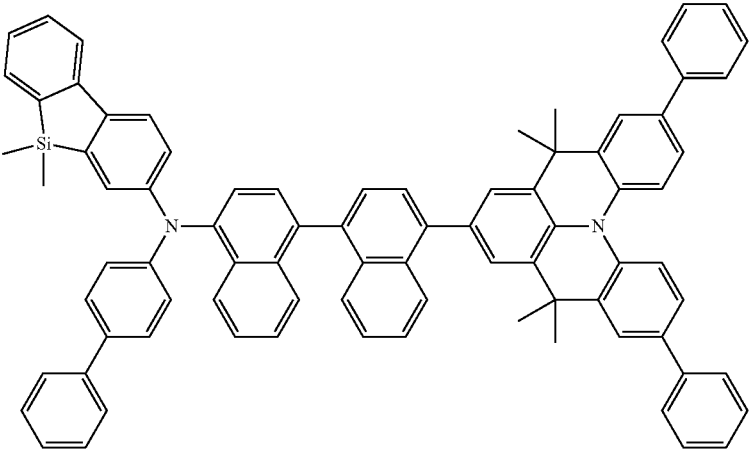 [SMILES: CC1(C)c2cc(-c3ccccc3)ccc2N2c3ccc(-c4ccccc4)cc3C(C)(C)c3cc(-c4ccc(-c5ccc(N(c6ccc(-c7ccccc7)cc6)c6ccc7c(c6)[Si](C)(C)c6ccccc6-7)c6ccccc56)c5ccccc45)cc1c32] |
| 100 | 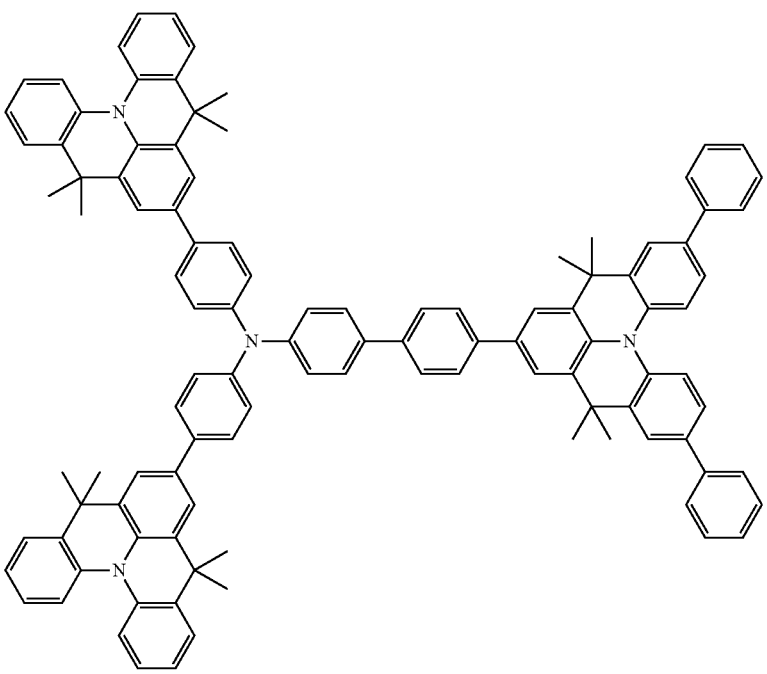 [SMILES: CC1(C)c2ccccc2N2c3ccccc3C(C)(C)c3cc(-c4ccc(N(c5ccc(-c6ccc(-c7cc8c9c(c7)C(C)(C)c7cc(-c%10ccccc%10)ccc7N9c7ccc(-c9ccccc9)cc7C8(C)C)cc6)cc5)c5ccc(-c6cc7c8c(c6)C(C)(C)c6ccccc6N8c6ccccc6C7(C)C)cc5)cc4)cc1c32] |

TABLE 4-continued
| No. | Structure |
|---|---|
| 101 | 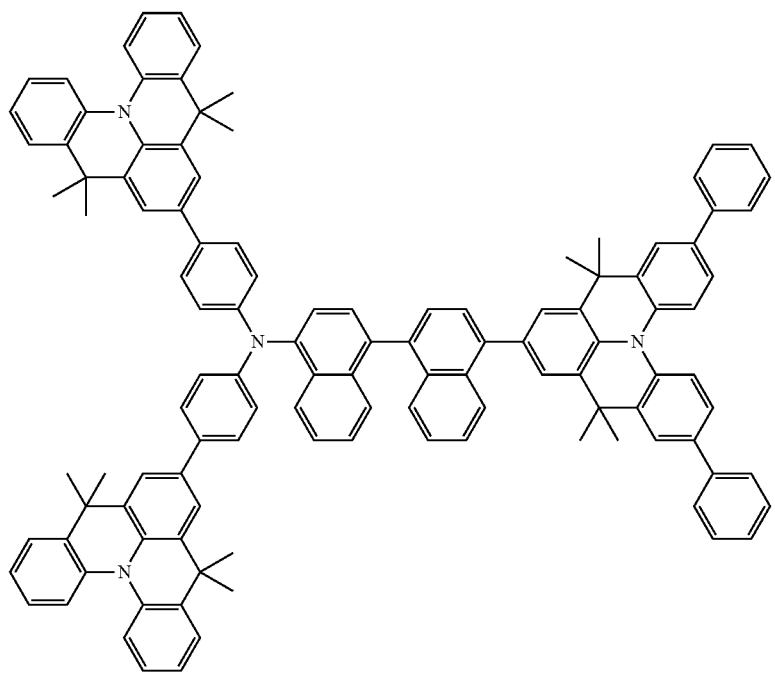 [SMILES: CC1(C)c2ccccc2N2c3ccccc3C(C)(C)c3cc(-c4ccc(N(c5ccc(-c6cc7c8c(c6)C(C)(C)c6ccccc6N8c6ccccc6C7(C)C)cc5)c5ccc(-c6ccc(-c7cc8c9c(c7)C(C)(C)c7cc(-c%10ccccc%10)ccc7N9c7ccc(-c9ccccc9)cc7C8(C)C)c7ccccc67)c6ccccc56)cc4)cc1c32] |
| 102 | 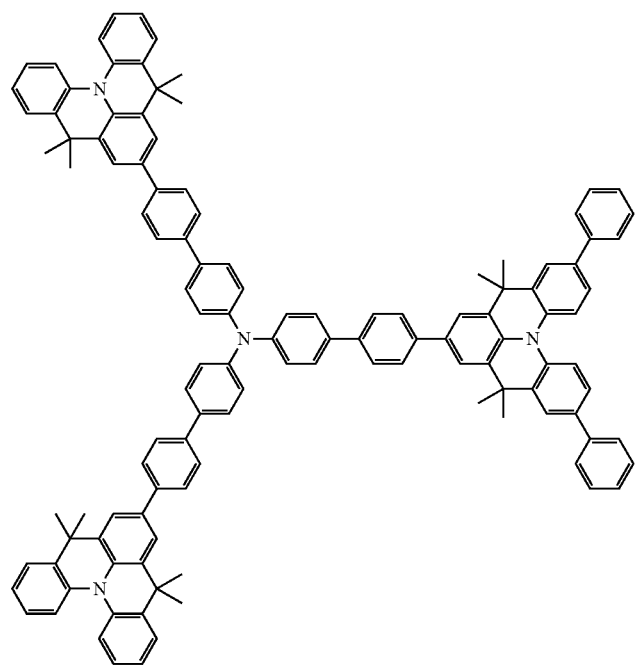 [SMILES: CC1(C)c2ccccc2N2c3ccccc3C(C)(C)c3cc(-c4ccc(-c5ccc(N(c6ccc(-c7ccc(-c8cc9c%10c(c8)C(C)(C)c8ccccc8N%10c8ccccc8C9(C)C)cc7)cc6)c6ccc(-c7ccc(-c8cc9c%10c(c8)C(C)(C)c8cc(-c%11ccccc%11)ccc8N%10c8ccc(-c%10ccccc%10)cc8C9(C)C)cc7)cc6)cc5)cc4)cc1c32] |

TABLE 4-continued
| No. | Structure |
|---|---|
| 103 | 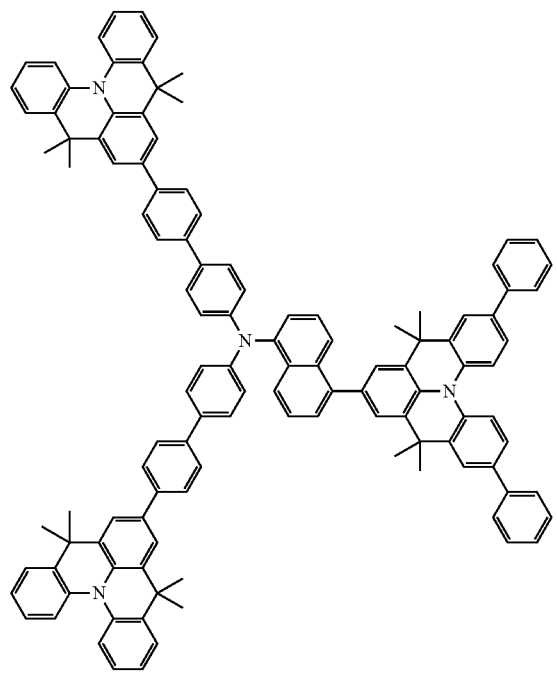 [SMILES: CC1(C)c2ccccc2N2c3ccccc3C(C)(C)c3cc(-c4ccc(-c5ccc(N(c6ccc(-c7ccc(-c8cc9c%10c(c8)C(C)(C)c8ccccc8N%10c8ccccc8C9(C)C)cc7)cc6)c6cccc7c(-c8cc9c%10c(c8)C(C)(C)c8cc(-c%11ccccc%11)ccc8N%10c8ccc(-c%10ccccc%10)cc8C9(C)C)cccc67)cc5)cc4)cc1c32] |
| 104 | 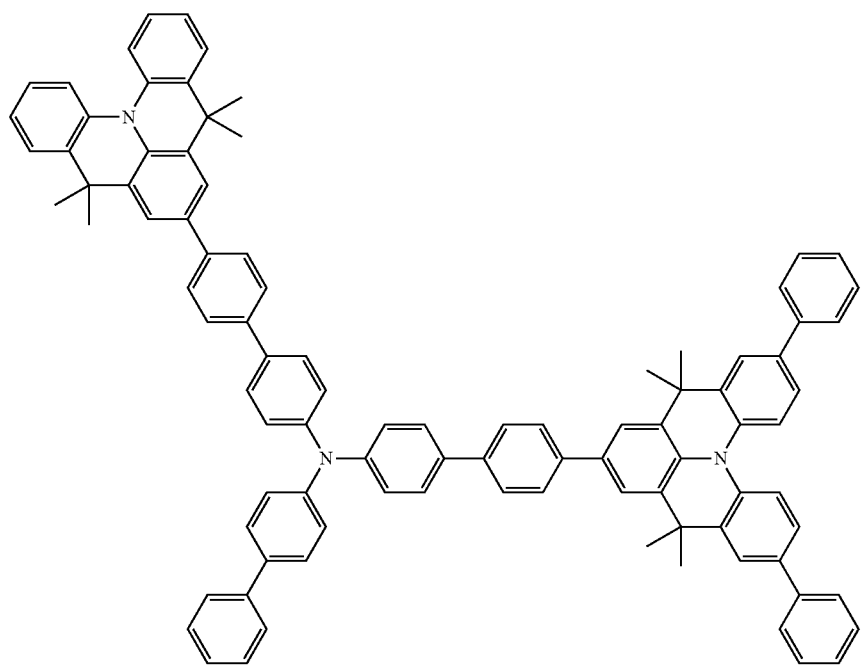 [SMILES: CC1(C)c2ccccc2N2c3ccccc3C(C)(C)c3cc(-c4ccc(-c5ccc(N(c6ccc(-c7ccccc7)cc6)c6ccc(-c7ccc(-c8cc9c%10c(c8)C(C)(C)c8cc(-c%11ccccc%11)ccc8N%10c8ccc(-c%10ccccc%10)cc8C9(C)C)cc7)cc6)cc5)cc4)cc1c32] |

TABLE 4-continued
| No. | Structure |
| --- | --- |
| 105 | 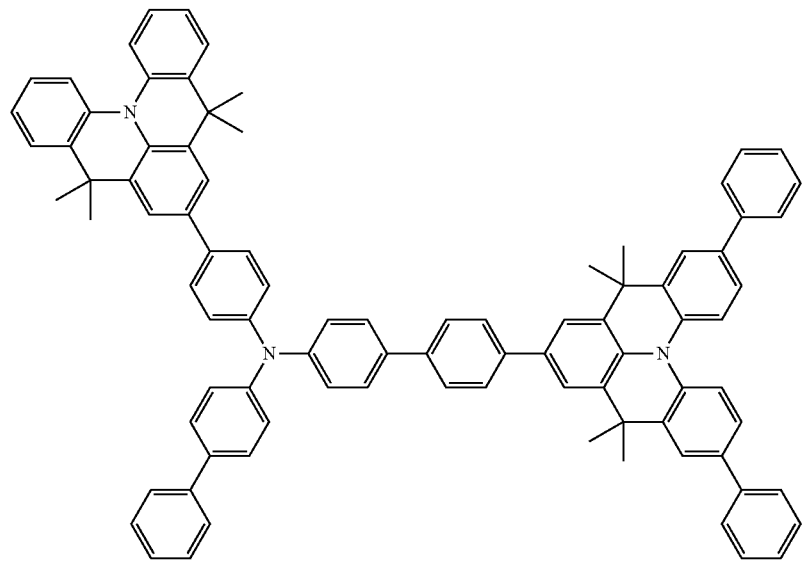 [SMILES: CC1(C)c2ccccc2N2c3ccccc3C(C)(C)c3cc(-c4ccc(N(c5ccc(-c6ccccc6)cc5)c5ccc(-c6ccc(-c7cc8c9c(c7)C(C)(C)c7cc(-c%10ccccc%10)ccc7N9c7ccc(-c9ccccc9)cc7C8(C)C)cc6)cc5)cc4)cc1c32] |
| 106 | 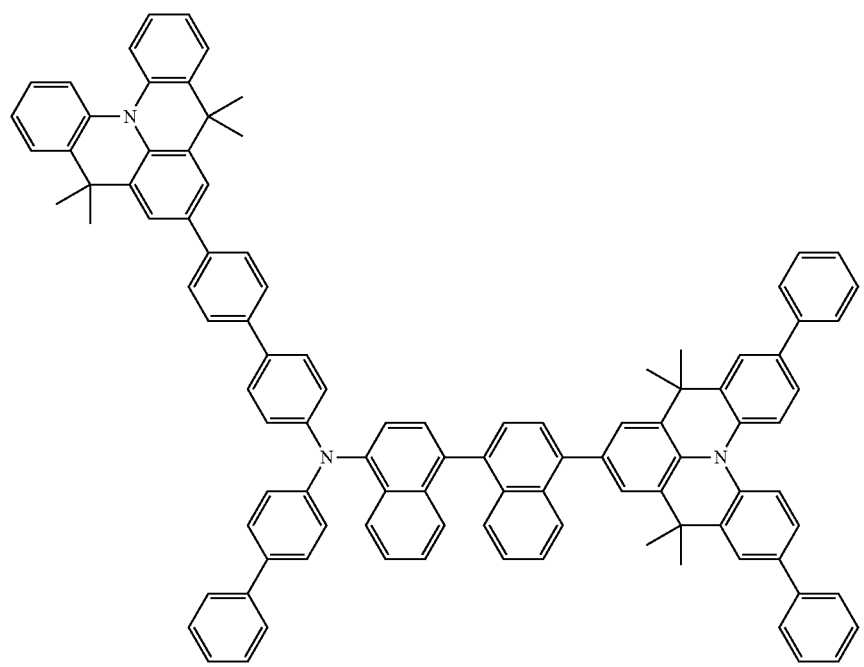 [SMILES: CC1(C)c2ccccc2N2c3ccccc3C(C)(C)c3cc(-c4ccc(-c5ccc(N(c6ccc(-c7ccccc7)cc6)c6ccc(-c7ccc(-c8cc9c%10c(c8)C(C)(C)c8cc(-c%11ccccc%11)ccc8N%10c8ccc(-c%10ccccc%10)cc8C9(C)C)c8ccccc78)c7ccccc67)cc5)cc4)cc1c32] |

TABLE 4-continued

| No. | Structure |
|---|---|
| 107 | 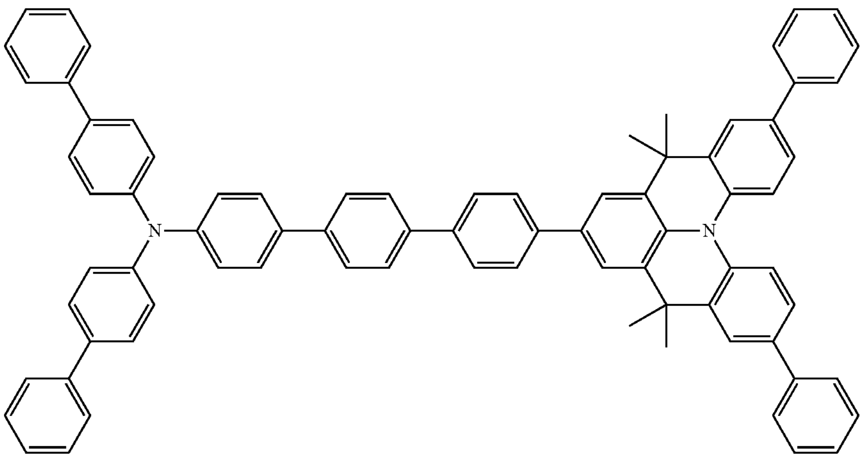 [SMILES: CC1(C)c2cc(-c3ccccc3)ccc2N2c3ccc(-c4ccccc4)cc3C(C)(C)c3cc(-c4ccc(-c5ccc(-c6ccc(N(c7ccc(-c8ccccc8)cc7)c7ccc(-c8ccccc8)cc7)cc6)cc5)cc4)cc1c32] |
| 108 | 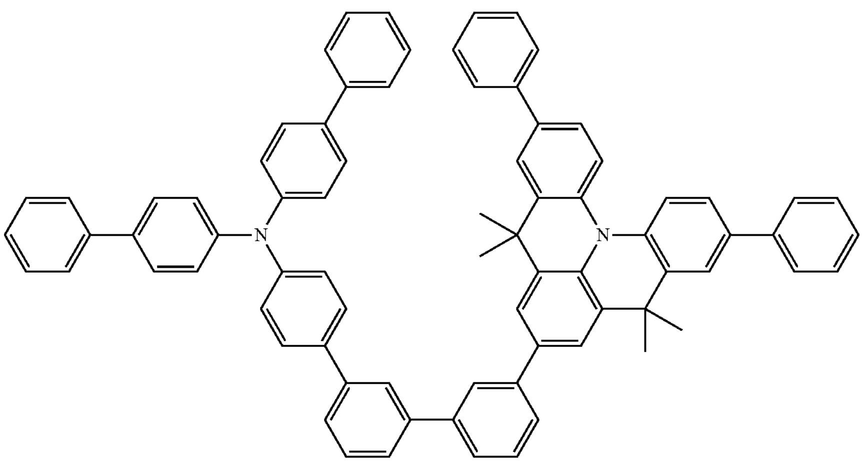 [SMILES: CC1(C)c2cc(-c3ccccc3)ccc2N2c3ccc(-c4ccccc4)cc3C(C)(C)c3cc(-c4cccc(-c5cccc(-c6ccc(N(c7ccc(-c8ccccc8)cc7)c7ccc(-c8ccccc8)cc7)cc6)c5)c4)cc1c32] |
| 109 | 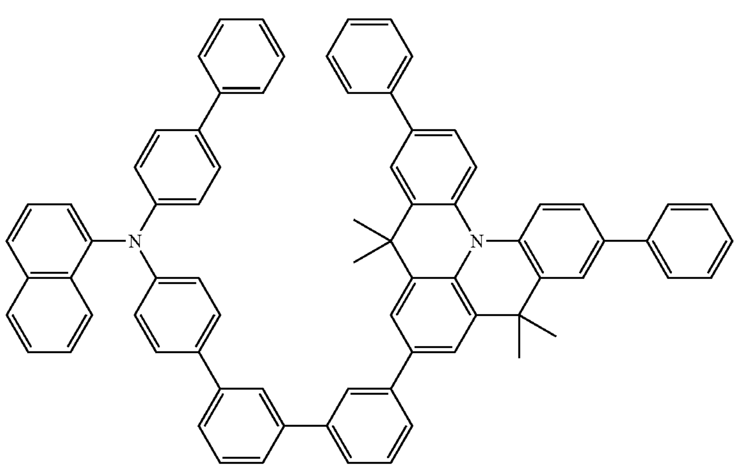 [SMILES: CC1(C)c2cc(-c3ccccc3)ccc2N2c3ccc(-c4ccccc4)cc3C(C)(C)c3cc(-c4cccc(-c5cccc(-c6ccc(N(c7ccc(-c8ccccc8)cc7)c7cccc8ccccc78)cc6)c5)c4)cc1c32] |

TABLE 4-continued
| No. | Structure |
|---|---|
| 110 | 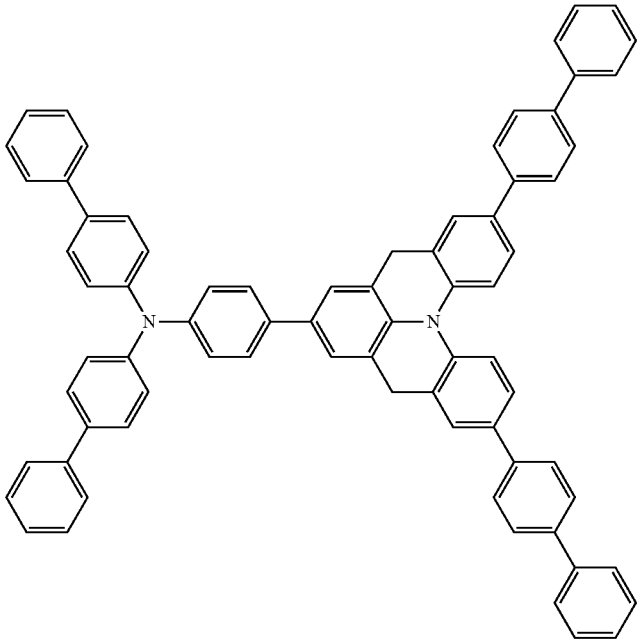 [SMILES: c1ccc(-c2ccc(-c3ccc4c(c3)Cc3cc(-c5ccc(N(c6ccc(-c7ccccc7)cc6)c6ccc(-c7ccccc7)cc6)cc5)cc5c3N4c3ccc(-c4ccc(-c6ccccc6)cc4)cc3C5)cc2)cc1] |
| 111 | 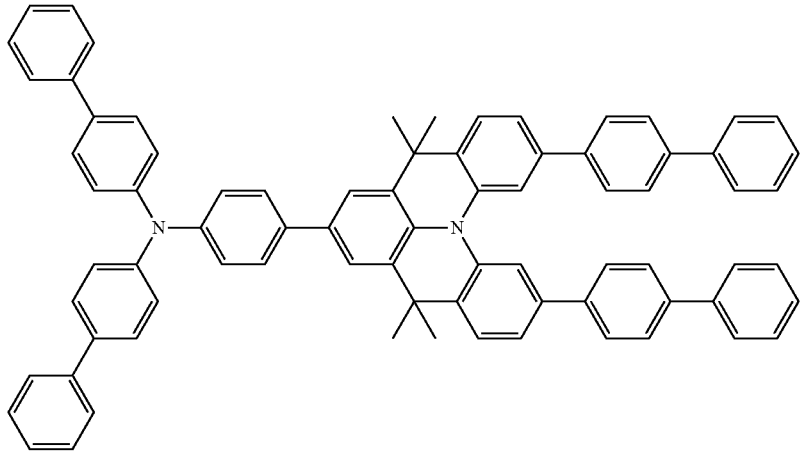 [SMILES: CC1(C)c2ccc(-c3ccc(-c4ccccc4)cc3)cc2N2c3cc(-c4ccc(-c5ccccc5)cc4)ccc3C(C)(C)c3cc(-c4ccc(N(c5ccc(-c6ccccc6)cc5)c5ccc(-c6ccccc6)cc5)cc4)cc1c32] |
| 112 | 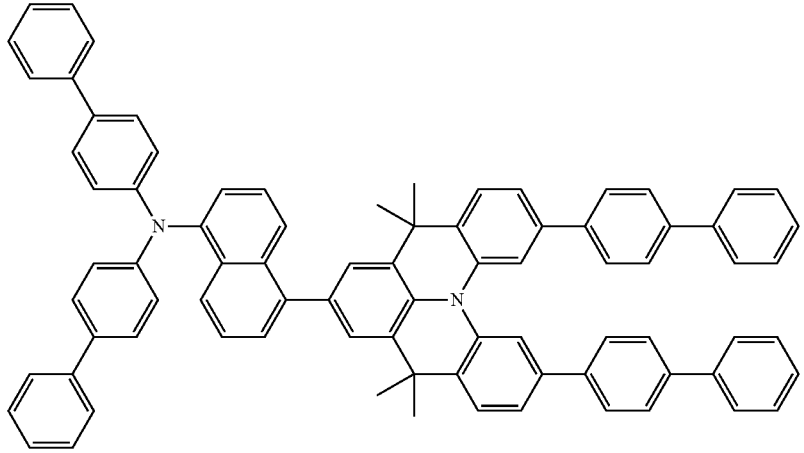 [SMILES: CC1(C)c2ccc(-c3ccc(-c4ccccc4)cc3)cc2N2c3cc(-c4ccc(-c5ccccc5)cc4)ccc3C(C)(C)c3cc(-c4cccc5c(N(c6ccc(-c7ccccc7)cc6)c6ccc(-c7ccccc7)cc6)cccc45)cc1c32] |

TABLE 4-continued
| No. | Structure |
| --- | --- |
| 113 | 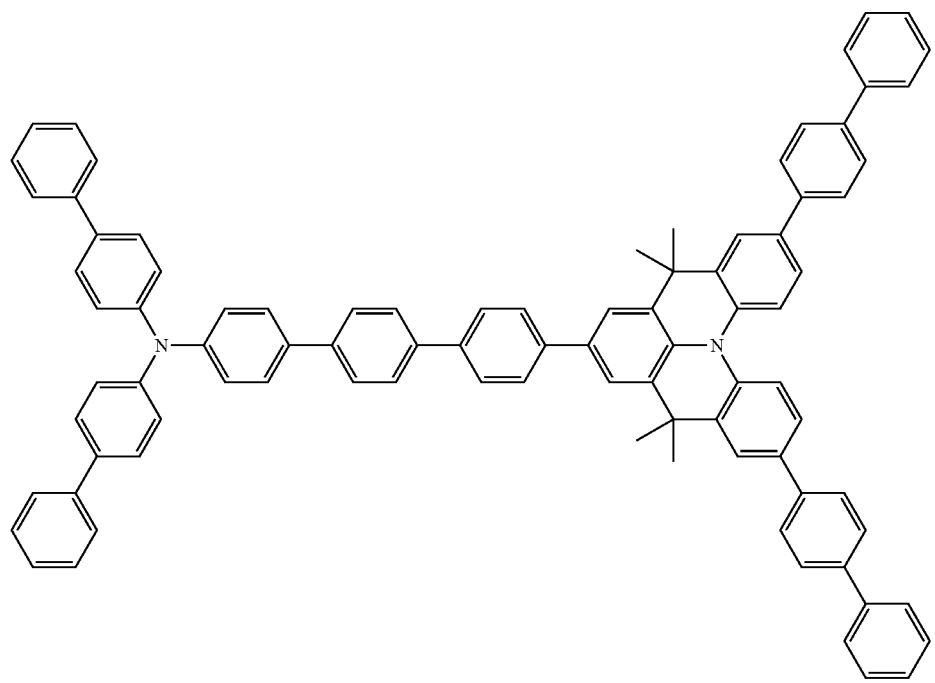 [SMILES: CC1(C)c2cc(-c3ccc(-c4ccccc4)cc3)ccc2N2c3ccc(-c4ccc(-c5ccccc5)cc4)cc3C(C)(C)c3cc(-c4ccc(-c5ccc(-c6ccc(N(c7ccc(-c8ccccc8)cc7)c7ccc(-c8ccccc8)cc7)cc6)cc5)cc4)cc1c32] |
| 114 | 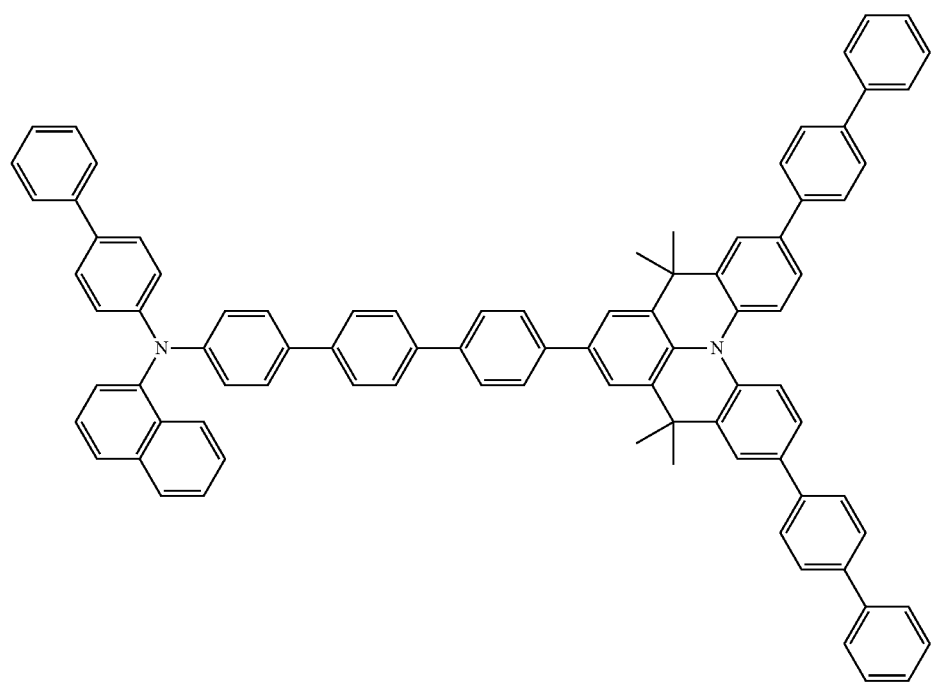 [SMILES: CC1(C)c2cc(-c3ccc(-c4ccccc4)cc3)ccc2N2c3ccc(-c4ccc(-c5ccccc5)cc4)cc3C(C)(C)c3cc(-c4ccc(-c5ccc(-c6ccc(N(c7ccc(-c8ccccc8)cc7)c7cccc8ccccc78)cc6)cc5)cc4)cc1c32] |

TABLE 4-continued
| No. | Structure |
|---|---|
| 115 | 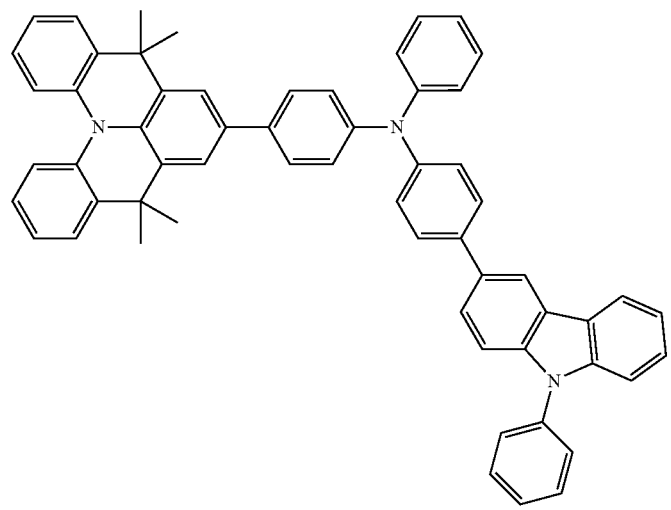 [SMILES: CC1(C)c2ccccc2N2c3ccccc3C(C)(C)c3cc(-c4ccc(N(c5ccccc5)c5ccc(-c6ccc7c(c6)c6ccccc6n7-c6ccccc6)cc5)cc4)cc1c32] |
| 116 | 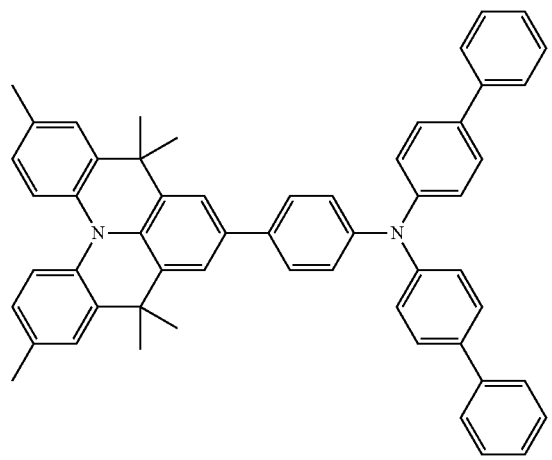 [SMILES: Cc1ccc2c(c1)C(C)(C)c1cc(-c3ccc(N(c4ccc(-c5ccccc5)cc4)c4ccc(-c5ccccc5)cc4)cc3)cc3c1N2c1ccc(C)cc1C3(C)C] |
| 117 | 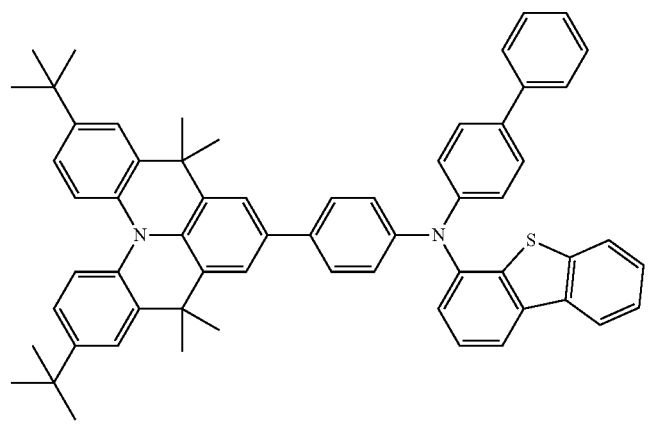 [SMILES: CC(C)(C)c1ccc2c(c1)C(C)(C)c1cc(-c3ccc(N(c4ccc(-c5ccccc5)cc4)c4cccc5c4sc4ccccc45)cc3)cc3c1N2c1ccc(C(C)(C)C)cc1C3(C)C] |

TABLE 4-continued

| No. | Structure |
|---|---|
| 118 | 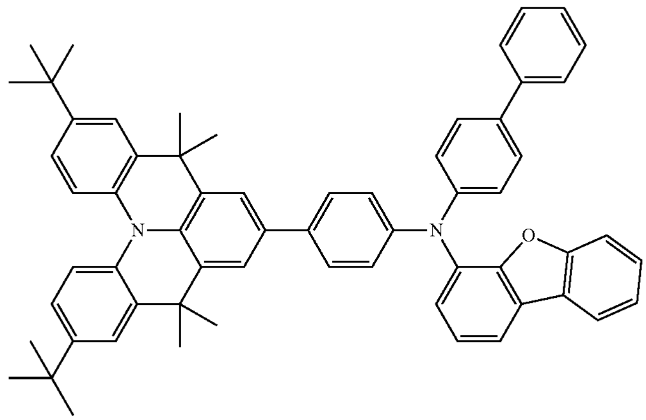 [SMILES: CC(C)(C)c1ccc2c(c1)C(C)(C)c1cc(-c3ccc(N(c4ccc(-c5ccccc5)cc4)c4cccc5c4oc4ccccc45)cc3)cc3c1N2c1ccc(C(C)(C)C)cc1C3(C)C] |
| 119 | 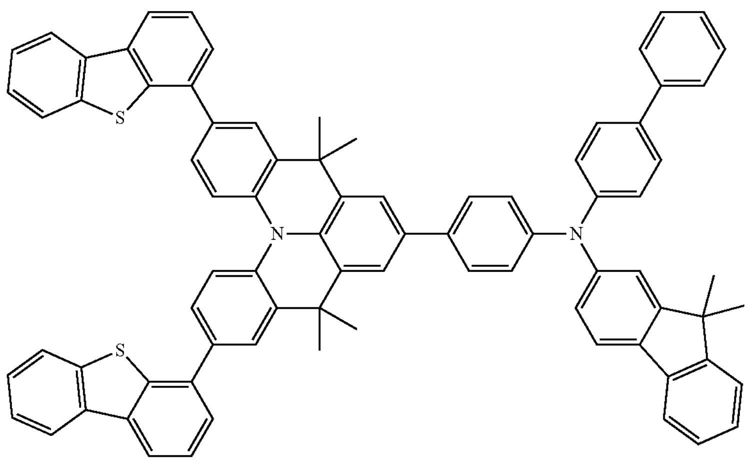 [SMILES: CC1(C)c2ccccc2-c2ccc(N(c3ccc(-c4ccccc4)cc3)c3ccc(-c4cc5c6c(c4)C(C)(C)c4cc(-c7cccc8c7sc7ccccc78)ccc4N6c4ccc(-c6cccc7c6sc6ccccc67)cc4C5(C)C)cc3)cc21] |
| 120 | 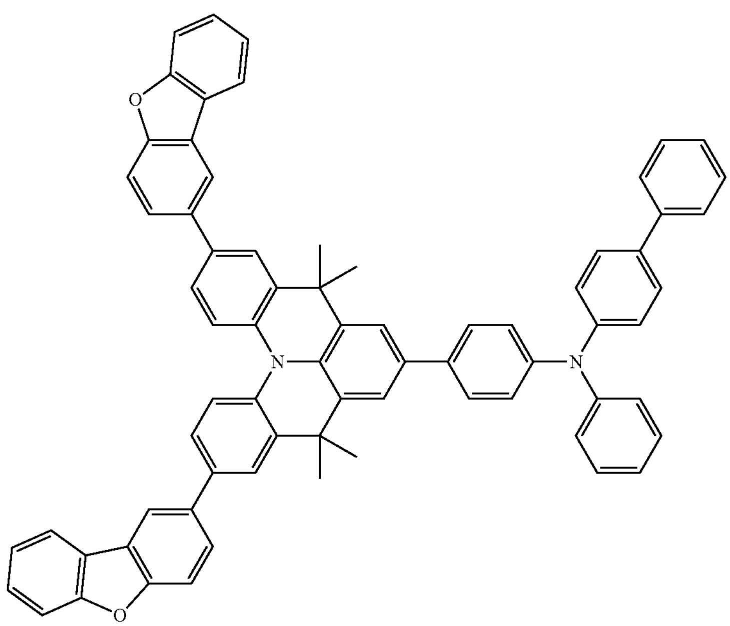 [SMILES: CC1(C)c2cc(-c3ccc4oc5ccccc5c4c3)ccc2N2c3ccc(-c4ccc5oc6ccccc6c5c4)cc3C(C)(C)c3cc(-c4ccc(N(c5ccccc5)c5ccc(-c6ccccc6)cc5)cc4)cc1c32] |

Hereinafter, a light-emitting element including the novel compound according to the present invention will be described with reference to the accompanying drawings. The structure of the light-emitting element including the compound is not limited by the accompanying drawings and the following description.

FIG. 1 is a cross-sectional view for describing a light-emitting element according to an exemplary embodiment of the present invention.

Referring to FIG. 1, a light-emitting element 100 includes a first electrode 20, a hole transporting layer 30, a light-emitting layer 40, and a second electrode 50, which are formed on a base substrate 10. The light-emitting element 100 may be an organic light emitting diode (OLED).

The first electrode 20 may be formed of a conductive material on the base substrate 10. As an example, the first electrode 20 may be a transparent electrode. In this case, the first electrode 20 may be formed of indium tin oxide (ITO). In contrast, the first electrode 20 may be an opaque (reflective) electrode. In this case, the first electrode 20 may have an ITO/silver (Ag)/ITO structure. The first electrode 20 may become an anode of the light-emitting diode 100.

The hole transporting layer 30 is formed on the first electrode 20 to be interposed between the first electrode 20 and the light-emitting layer 40. The hole transporting layer 30 includes a compound represented by the following Formula 1 as a hole transporting compound.

[Formula 1]

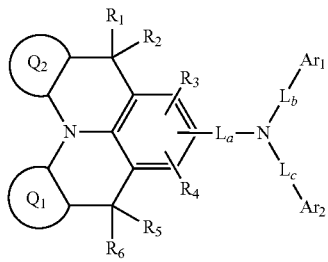

The compound represented by Formula 1 is a novel compound according to the present invention and is substantially the same as those described above. Accordingly, the specific description of each of $R_1$ to $R_6$, $L_a$, $L_b$, $L_c$, $Q_1$, $Q_2$, $Ar_1$, and $Ar_2$ will be omitted.

The wavelength of light which the light-emitting layer 40 emits may vary according to the kind of compound which forms the light-emitting layer 40.

The second electrode 50 may be formed of a conductive material on the light-emitting layer 40. When the first electrode 20 is a transparent electrode, the second electrode 50 may be an opaque (reflective) electrode. In this case, the second electrode 50 may be an aluminum electrode. In contrast, when the first electrode 20 is an opaque electrode, the second electrode 50 may be a transparent or semi-transparent electrode. In this case, the second electrode 50 may have a thickness of 100 Å to 150 Å, and may be an alloy including magnesium and silver. The second electrode 50 may become a cathode of the light-emitting element 100.

Between the light-emitting layer 40 and the second electrode 50, an electron transporting layer and/or an electron injecting layer may be formed as an electron transporting layer.

When current flows between the first and second electrodes 20 and 50 of the light-emitting element 100, a hole injected from the first electrode 20 to the light-emitting layer 40 and an electron injected from the second electrode 50 to the light-emitting layer 40 combine with each other to form an exciton. While the exciton is transferred to a bottom state, light having a wavelength at a specific band is produced. In this case, the exciton may be a singlet exciton, and may also be a triplet exciton. Accordingly, the light-emitting element 100 may provide light to the outside.

Even though not illustrated in the drawing, the light-emitting element 100 may further include an electron transporting layer (ETL) and an electron injecting layer (EIL), which are disposed between the light-emitting layer 40 and the second electrode 50. The electron transporting layer and the electron injecting layer may be sequentially stacked and formed on the light-emitting layer 40.

Further, the light-emitting element 100 may further include a first blocking layer (not illustrated) disposed between the first electrode 20 and the light-emitting layer 40 and/or a second blocking layer (not illustrated) disposed between the light-emitting layer 40 and the second electrode 50.

For example, the first blocking layer may be an electron blocking layer (EBL) which is disposed between the hole transporting layer 30 and the light-emitting layer 40 and thus prevents electrons injected from the second electrode 50 from flowing into the hole transporting layer 30 via the light-emitting layer 40. In addition, the first blocking layer may be an exciton blocking layer which prevents an exciton formed in the light-emitting layer 40 from being diffused in a direction of the first electrode 20 and thus being non-radiatively decayed.

In this case, the first blocking layer may include the compound according to the present invention, which is described above.

The second blocking layer may be a hole blocking layer (HBL) which is disposed between the light-emitting layer 40 and the second electrode 50, specifically, the light-emitting layer 40 and the electron transporting layer, and thus prevents holes from flowing into the electron transporting layer via the light-emitting layer 40 from the first electrode 20. Furthermore, the second blocking layer may be an exciton blocking layer which prevents an exciton formed in the light-emitting layer 40 from being diffused in a direction of the second electrode 50 and thus being non-radiatively decayed.

When the thickness of each of the first and second blocking layers is adjusted so as to be suitable for the resonance length of the light-emitting element 100, the light-emitting efficiency may be increased, and the exciton may be adjusted so as to be formed in the central part of the light-emitting layer 40.

Referring to FIG. 2, a light-emitting element 102 includes a first electrode 20, a hole transporting layer 32, a light-emitting layer 40, and a second electrode 50, which are formed on a base substrate 10. Except for the hole transporting layer 32, the other constituent elements are substantially the same as those described in FIG. 1, and thus the overlapping description thereof will be omitted.

The hole transporting layer 32 includes the compound represented by Formula 1 and a P-type dopant. Since a compound included in the hole transporting layer 32 is substantially the same as that described above, the overlapping specific description thereof will be omitted.

The P-type dopant may include a P-type organic dopant and/or a P-type inorganic dopant.

Specific examples of the P-type organic dopant include compounds represented by the following Formulae 10 to 14, hexadecafluorophthalocyanine (F16CuPc), 11,11,12,12-tetracyanonaphtho-2,6-quinodimethane (TNAP), 3,6-difluoro-2,5,7,7,8,8-hexacyano-quinodimethane (F2-HCNQ), or tetracyanoquinodimethane (TCNQ), and the like. These may be used either alone or in combination of two or more thereof.

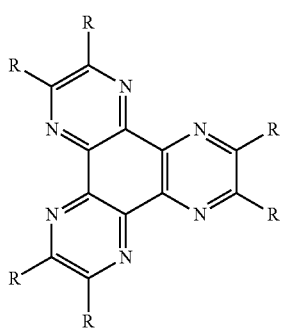

[Formula 10]

In Formula 10, R may represent a cyano group, a sulfone group, a sulfoxide group, a sulfonamide group, a sulfonate group, a nitro group, or a trifluoromethyl group.

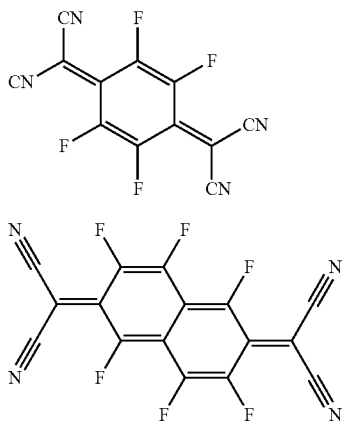

[Formula 11]

[Formula 12]

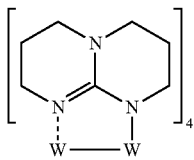

[Formula 13]

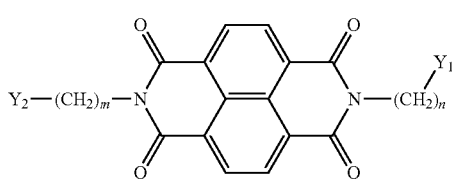

[Formula 14]

In Formula 14, m and n may each independently represent an integer of 1 to 5, and $Y_1$ and $Y_2$ may each independently represent an aryl group having 6 to 20 carbon atoms, or a heteroaryl group having 2 to 20 carbon atoms. In this case, a hydrogen atom of the aryl group or heteroaryl group represented by $Y_1$ and $Y_2$ may be unsubstituted or substituted with an alkyl group having 1 to 5 carbon atoms, an alkoxy group having 1 to 5 carbon atoms, or a hydroxyl group, and hydrogen atoms of substituted or unsubstituted $Y_1$ and $Y_2$ may be each independently unsubstituted or substituted with a halogen group.

For example, the compound represented by Formula 14 may include a compound represented by the following Formula 14a or the following Formula 14b.

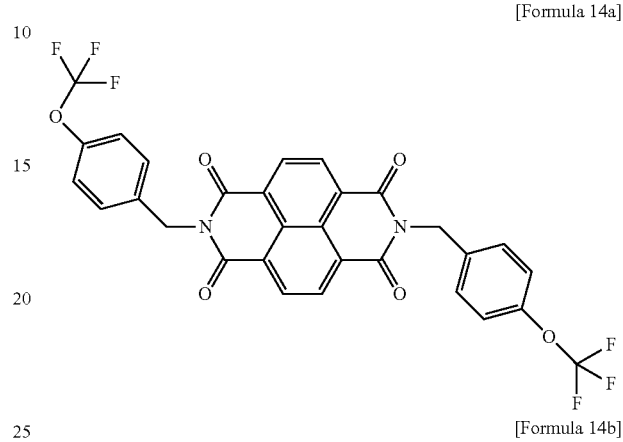

[Formula 14a]

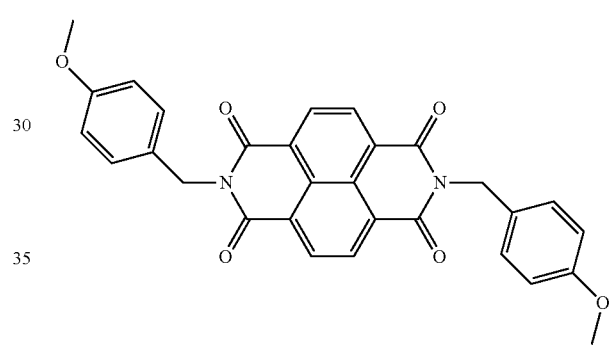

[Formula 14b]

Examples of the P-type inorganic dopant include metal oxide or metal halide, and the like. Specific examples of the P-type inorganic dopant include $MoO_3$, $V_2O_5$, $WO_3$, $SnO_2$, $ZnO$, $MnO_2$, $CoO_2$, $ReO_3$, $TiO_2$, $FeCl_3$, $SbCl_5$ or $MgF_2$, and the like. These may be used either alone or in combination of two or more thereof.

The content of the P-type dopant may be about 0.5 part by weight to about 20 parts by weight based on 100 parts by weight of the novel compound according to the present invention, which is a hole transporting compound. For example, the content of the P-type dopant may be about 0.5 part by weight to about 15 parts by weight, or about 0.5 part by weight to about 5 parts by weight based on 100 parts by weight of the hole transporting compound. In contrast, the content of the P-type dopant may be about 1 part by weight to about 10 parts by weight, about 1 part by weight to about 5 parts by weight, about 1.5 parts by weight to about 6 parts by weight, or about 2 parts by weight to about 5 parts by weight, based on 100 parts by weight of the hole transporting compound.

When the content of the P-type dopant is about 0.5 part by weight to about 20 parts by weight based on 100 parts by weight of the hole transporting compound, the P-type dopant may prevent an excessive leakage current from being generated without degrading physical properties of the hole transporting compound. In addition, the energy barrier at the interface with each of the upper and lower layers, which are brought into contact with the hole transporting layer 32, may be reduced by the P-type dopant.

Even though not illustrated in the drawing, the light-emitting element 102 may further include an electron transporting layer, an electron injecting layer, a first blocking layer, and/or a second blocking layer. Since the layers are substantially the same as those described in the light-emitting element 100 of FIG. 1, the specific description thereof will be omitted. When the light-emitting element 102 includes the first blocking layer, the first blocking layer may include the compound according to the present invention, which is described above.

Meanwhile, the light-emitting element 100 illustrated in FIG. 1 may further include an interlayer (not illustrated). The interlayer may be disposed between the first electrode 20 and the hole transporting layer 30 of FIG. 1, and may be formed of the compound used as the P-type dopant described in FIG. 2.

Referring to FIG. 3, a light-emitting element 104 includes a first electrode 20, a hole transporting layer 34, a light-emitting layer 40, and a second electrode 50, which are formed on a base substrate 10. Except for the hole transporting layer 34, the other constituent elements are substantially the same as those described in FIG. 1, and thus the overlapping description thereof will be omitted.

The hole transporting layer 34 includes a first layer 33a brought into contact with the first electrode 20 and a second layer 33b disposed between the first layer 33a and the light-emitting layer 40. That is, the hole transporting layer 34 may have a two-layer structure. Furthermore, the hole transporting layer 34 may have a multi-layer structure having two or more layers, which includes the first and second layers 33a and 33b.

The first and second layers 33a and 33b may include the same kind of hole transporting compound. Since components of the hole transporting compound to be included in the first layer 33a and the second layer 33b are made identical to each other, physical and chemical defects which may be generated at the interface between different species materials may be reduced, thereby facilitating injection of holes into the light-emitting layer. In another aspect, when the same host material is used for the first layer 33a and the second layer 33b, there are advantages in that the first layer 33a and the second layer 33b may be continuously formed within one chamber, so that the manufacturing process may be simplified and the manufacturing time may be shortened. Furthermore, physical properties such as the glass transition temperature between the layers adjacent to each other become similar to each other, so that there is also an advantage in that durability of the element may be increased.

The first layer 33a includes the novel compound according to the present invention, which is represented by Formula 1 as the hole transporting compound, and a P-type dopant. Except for the thickness, the first layer 33a is substantially the same as the hole transporting layer 32 described in FIG. 2. Therefore, the overlapping description thereof will be omitted.

The second layer 33b includes the novel compound according to the present invention, which is represented by Formula 1, as the hole transporting compound, but the hole transporting compound which constitutes the second layer 33b may be the same as the hole transporting compound which constitutes the first layer 33a. Except for the thickness, the second layer 33b is also substantially the same as the hole transporting layer 30 described in FIG. 1, and thus the overlapping detailed description thereof will be omitted.

In contrast, the first and second layers 33a and 33b may include a different kind of hole transporting compound. The hole transporting compound, which constitutes the first and second layers 33a and 33b, is the novel compound according to the present invention, which is represented by Formula 1, but $R_1$ to $R_6$, $L_a$, $L_b$, $L_c$, $Ar_1$, and $Ar_2$ may be each independently different from each other. In this case, the compound, which constitutes each of the first and second layers 33a and 33b, may be selected so as to have a HOMO value for efficiently transferring holes to the light-emitting layer 40.

Additionally, the second layer 33b may further include a P-type dopant together with the hole transporting compound. In this case, the kinds of P-type dopants doped in the first layer 33a and the second layer 33b may be different from each other, and an amount of doping may vary even though the same kind of P-type dopants are used. For example, a content (P1) of the P-type dopant doped in the first layer 33a and a content (P2) of the P-type dopant doped in the second layer 33b may satisfy the relationship of the following Equation 1.

$$P1/P2 \geq 1 \qquad \text{[Equation 1]}$$

In Equation 1,

"P1" is a content of the P-type dopant doped in the first layer 33a based on 100 parts by weight of the hole transporting compound, and "P2" is a content of the P-type dopant doped in the second layer 33b based on 100 parts by weight of the hole transporting compound.

For example, the content of the P-type dopant doped in the first layer 33a may range from 0.3 to 20 parts by weight, 1 to 15 parts by weight, 2 to 10 parts by weight, or 4 to 6 parts by weight based on 100 parts by weight of the hole transporting compound. Further, the content of the P-type dopant doped in the second layer 33b may range from 0.3 to 20 parts by weight, 0.5 to 10 parts by weight, 1 to 8 parts by weight, or 2 to 4 parts by weight, based on 100 parts by weight of the hole transporting compound.

In addition, even though not illustrated in the drawing, the light-emitting element 104 may further include an electron transporting layer, an electron injecting layer, a first blocking layer, and/or a second blocking layer. Since the layers are substantially the same as those described in the light-emitting element 100 of FIG. 1, the specific description thereof will be omitted.

Each of the light-emitting elements 100, 102, and 104 described above includes the novel compound according to the present invention, which is represented by Formula 1, and thus the light-emitting elements 100, 102, and 104 may have excellent thermal stability, and simultaneously, the light-emitting efficiency thereof may be enhanced and the lifespan thereof may be increased.

FIGS. 1 to 3 illustrate that the light-emitting diodes 100, 102, and 104 are directly formed on the base substrate 10, but a thin film transistor may be disposed as a driving element, which drives pixels, between the first electrode 20 of each of the light-emitting diodes 100, 102, and 104 and the base substrate 10. In this case, the first electrode 20 may become a pixel electrode connected to the thin film transistor. When the first electrode 20 is a pixel electrode, the first electrodes 20 are disposed spaced apart from each other in each of a plurality of pixels, and a partition wall pattern formed along the edge of the first electrode 20 is formed on the base substrate 10, so that layers to be stacked on the first electrode 20, which are disposed on the pixels adjacent to each other may be isolated from each other. That is, even though not illustrated in the drawings, the light-emitting elements 100, 102, and 104 may be used for a display device which displays an image without a backlight.

Furthermore, the light-emitting elements 100, 102, and 104 may be used as a lighting device.

As described above, the light-emitting elements 100, 102, and 104 exemplified in the present invention may be used for various electronic devices such as the display device or the lighting device.

EXAMPLES

Hereinafter, the present invention will be described in more detail through specific Examples of the novel compound according to the present invention. The Examples to be exemplified below are only provided for the detailed description of the invention, but are not intended to limit the right scope thereby.

Example 1

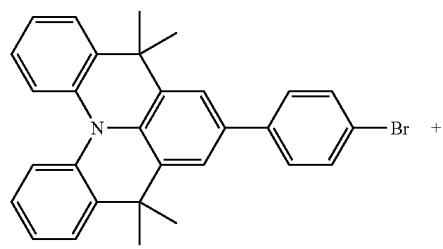

Compound A

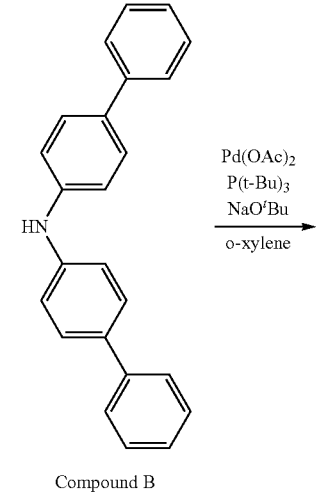

Compound B

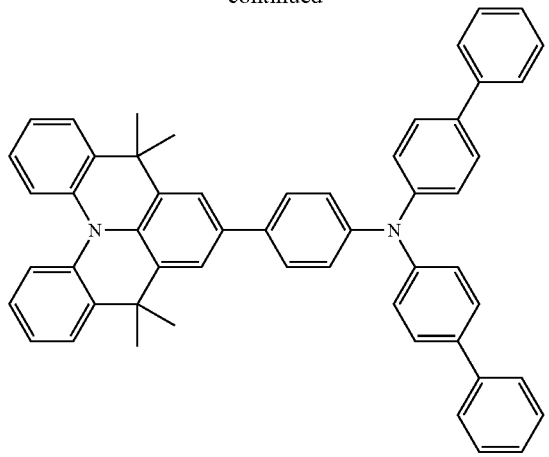

Compound 1

A 250 mL three-neck round-bottom flask was filled with nitrogen, and then Compound A (20 g, 41.6 mmol), Compound B (14.7 g, 45.8 mmol), palladium acetate (Pd(OAc)$_2$) (190 mg, 0.83 mmol), sodium tert-butoxide (4.8 g, 50.0 mmol), 200 mL of o-xylene, and a 1M toluene solution (1.7 ml, 1.7 mmol) of tri-tert-butylphosphine were added thereto, and the resulting mixture was heated at 130° C. for 4 hours. The mixture was cooled to normal temperature and was added to 2,000 mL of methanol, and the resulting mixture was stirred, and then filtered, thereby obtaining 21.0 g of a white solid Compound 1 (yield 70%).

MALDI-TOF: m/z=720.3504 (C$_{54}$H$_{44}$N$_2$=720.35)

Example 2

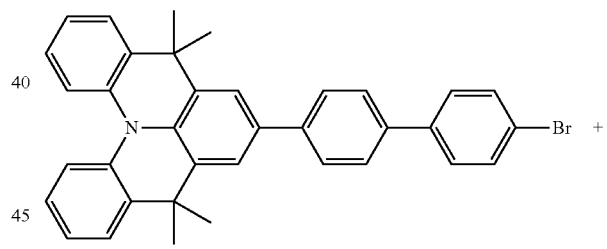

Compound C

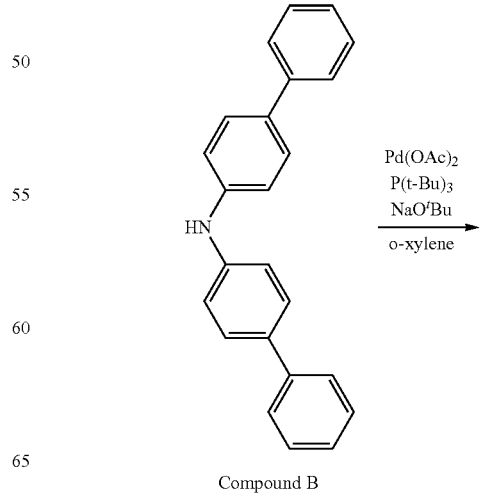

Compound B

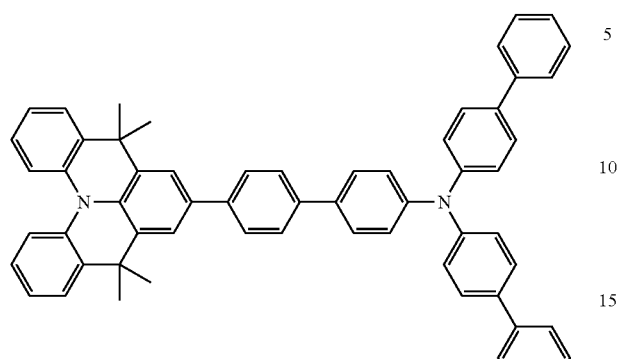

Compound 2

A 250 mL three-neck round-bottom flask was filled with nitrogen, and then Compound C (15 g, 27.0 mmol), Compound B (9.5 g, 29.6 mmol), palladium acetate (Pd(OAc)$_2$) (120 mg, 0.54 mmol), sodium tert-butoxide (3.1 g, 32.3 mmol), 150 mL of o-xylene, and a 1M toluene solution (1.1 ml, 1.1 mmol) of tri-tert-butylphosphine were added thereto, and the resulting mixture was heated at 130° C. for 4 hours. The mixture was cooled to normal temperature and was added to 500 mL of methanol, and the resulting mixture was stirred, and then filtered, thereby obtaining 16.1 g of a pale yellow solid Compound 2 (yield 75%).

MALDI-TOF: m/z=796.3817 (C$_{60}$H$_{48}$N$_2$=796.38)

Example 3

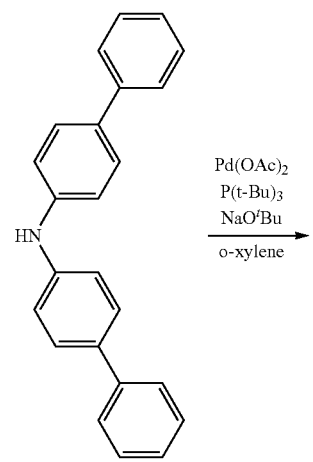

Compound B

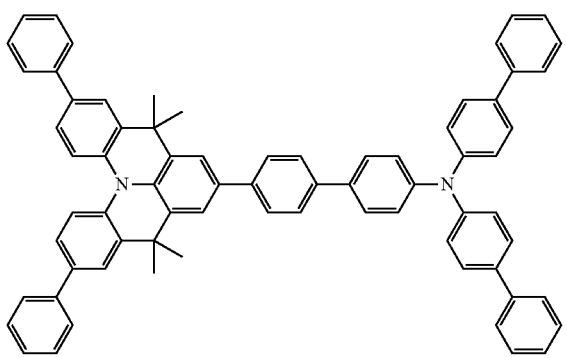

Compound 3

A 250 mL three-neck round-bottom flask was filled with nitrogen, and then Compound D (18 g, 25.4 mmol), Compound B (9.0 g, 27.9 mmol), palladium acetate (Pd(OAc)$_2$) (110 mg, 0.51 mmol), sodium tert-butoxide (2.9 g, 30.5 mmol), 180 mL of o-xylene, and a 1M toluene solution (1.0 ml, 1.0 mmol) of tri-tert-butylphosphine were added thereto, and the resulting mixture was heated at 130° C. for 5 hours. The mixture was cooled to normal temperature and was added to 1,800 mL of methanol, and the resulting mixture was stirred, and then filtered, thereby obtaining 19.3 g of a yellow solid Compound 3 (yield 80%).

MALDI-TOF: m/z=948.4443 (C$_{72}$H$_{56}$N$_2$=948.44)

Example 4

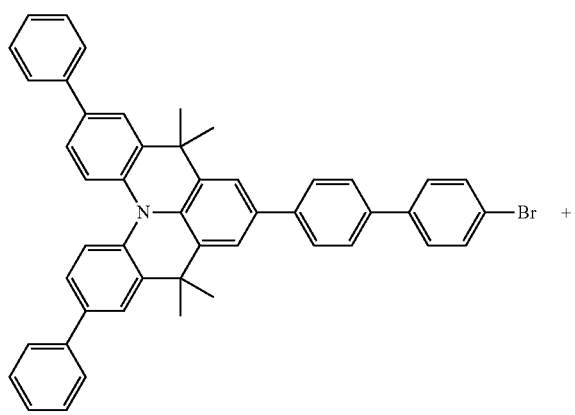

Compound D

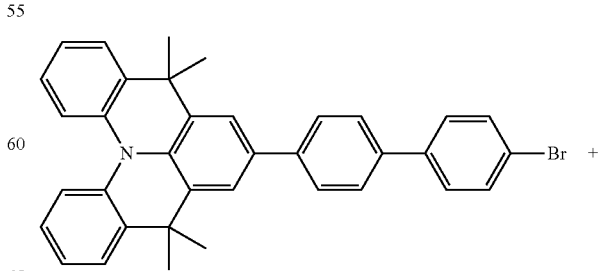

Compound C

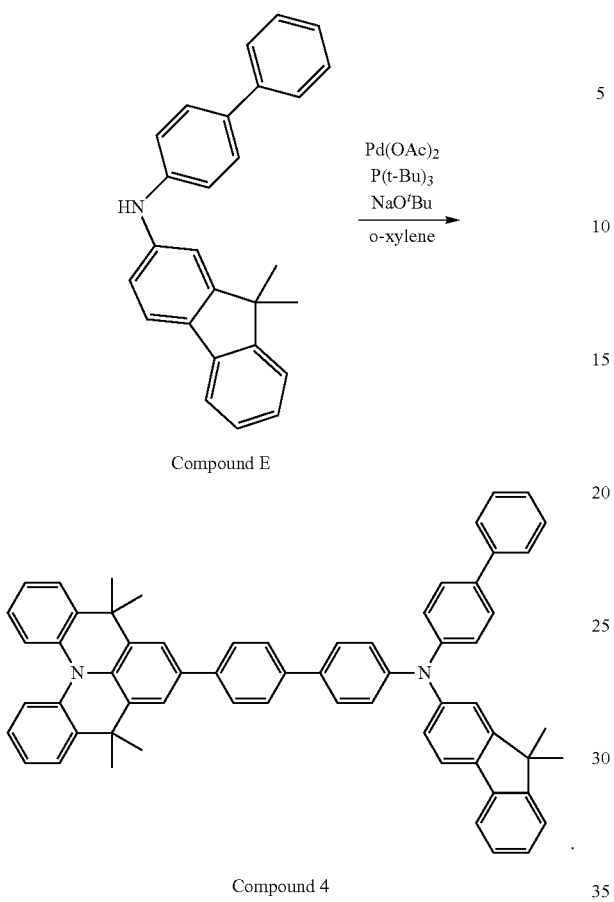

Compound E

Compound 4

A 250 mL three-neck round-bottom flask was filled with nitrogen, and then Compound C (21.0 g, 37.7 mmol), Compound E (15.0 g, 41.5 mmol), palladium acetate (Pd(OAc)$_2$) (170 mg, 0.75 mmol), sodium tert-butoxide (4.4 g, 45.3 mmol), 210 mL of o-xylene, and a 1M toluene solution (1.5 ml, 1.5 mmol) of tri-tert-butylphosphine were added thereto, and the resulting mixture was heated at 130° C. for 4 hours. The mixture was cooled to normal temperature and was added to 2,100 mL of methanol, and the resulting mixture was stirred, and then filtered, thereby obtaining 25.3 g of a pale brown solid Compound 4 (yield 80%).

MALDI-TOF: m/z=836.413 (C$_{63}$H$_{52}$N$_2$=836.41)

Example 5

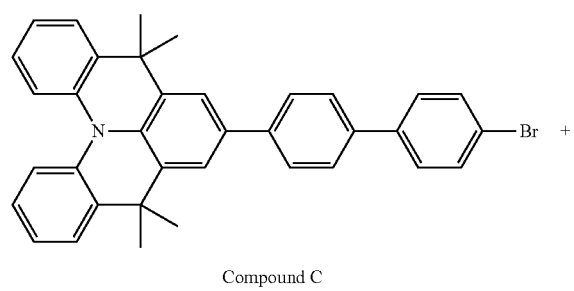

Compound C

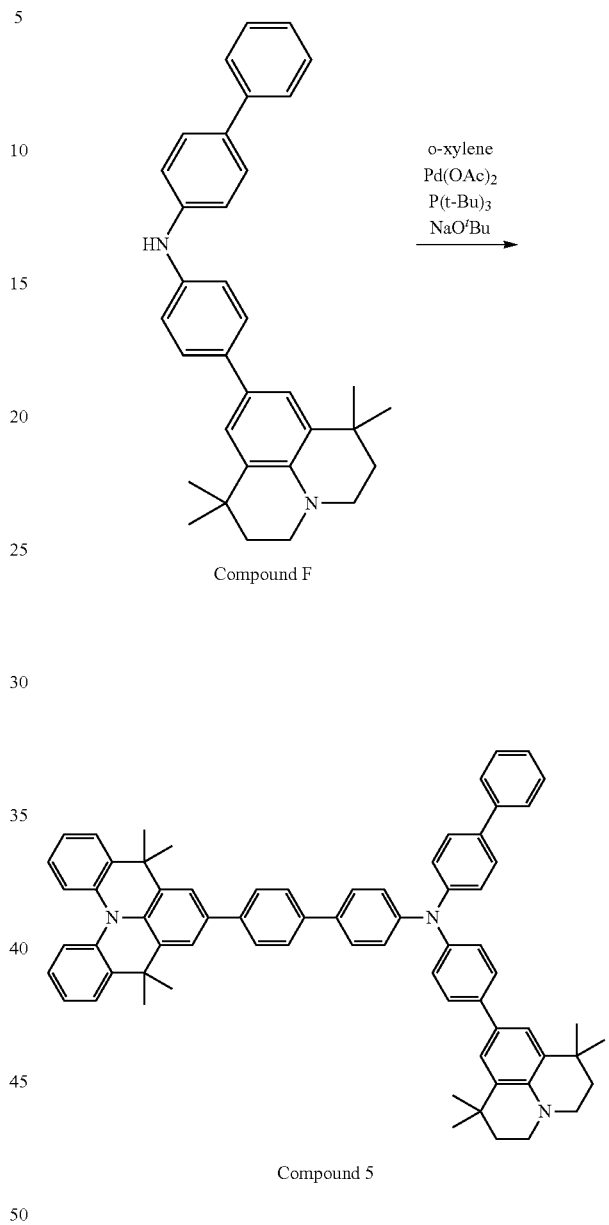

Compound F

Compound 5

A 250 mL three-neck round-bottom flask was filled with nitrogen, and then Compound C (15 g, 27.0 mmol), Compound F (14.0 g, 29.6 mmol), palladium acetate (Pd(OAc)$_2$) (120 mg, 0.54 mmol), sodium tert-butoxide (3.1 g, 32.3 mmol), 150 mL of o-xylene, and a 1M toluene solution (1.1 ml, 1.1 mmol) of tri-tert-butylphosphine were added thereto, and the resulting mixture was heated at 130° C. for 2 hours. The mixture was cooled to normal temperature and was added to 1,500 mL of methanol, and the resulting mixture was stirred, and then filtered, thereby obtaining 21.0 g of a solid Compound 5 (yield 82%).

MALDI-TOF: m/z=947.5178 (C$_{70}$H$_{65}$N$_3$=947.52)

Example 6

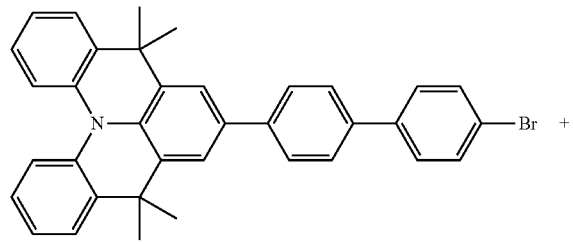

Compound C

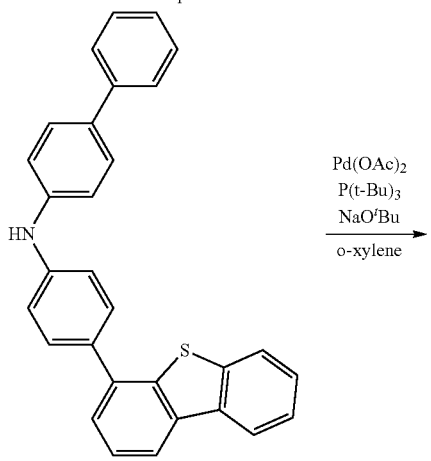

Compound G

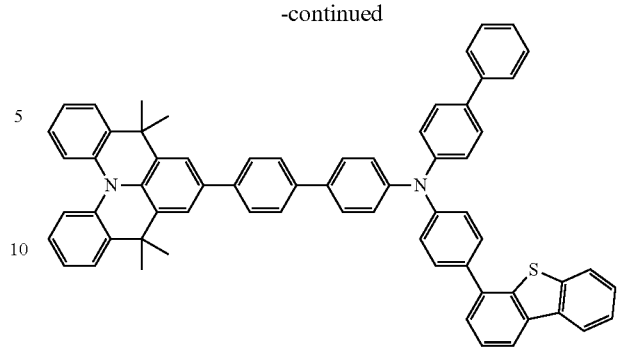

Compound 6

A 250 mL three-neck round-bottom flask was filled with nitrogen, and then Compound C (19 g, 34.1 mmol), Compound G (16.1 g, 37.6 mmol), palladium acetate (Pd(OAc)$_2$) (150 mg, 0.68 mmol), sodium tert-butoxide (3.9 g, 41.0 mmol), 190 mL of o-xylene, and a 1M toluene solution (1.4 ml, 1.4 mmol) of tri-tert-butylphosphine were added thereto, and the resulting mixture was heated at 130° C. for 4 hours. The mixture was cooled to normal temperature and was added to 1,900 mL of methanol, and the resulting mixture was stirred, and then filtered, thereby obtaining 22.2 g of a yellowish green Compound 6 (yield 72%).

MALDI-TOF: m/z=902.3695 (C$_{66}$H$_{50}$N$_2$S=902.36)

Example 7

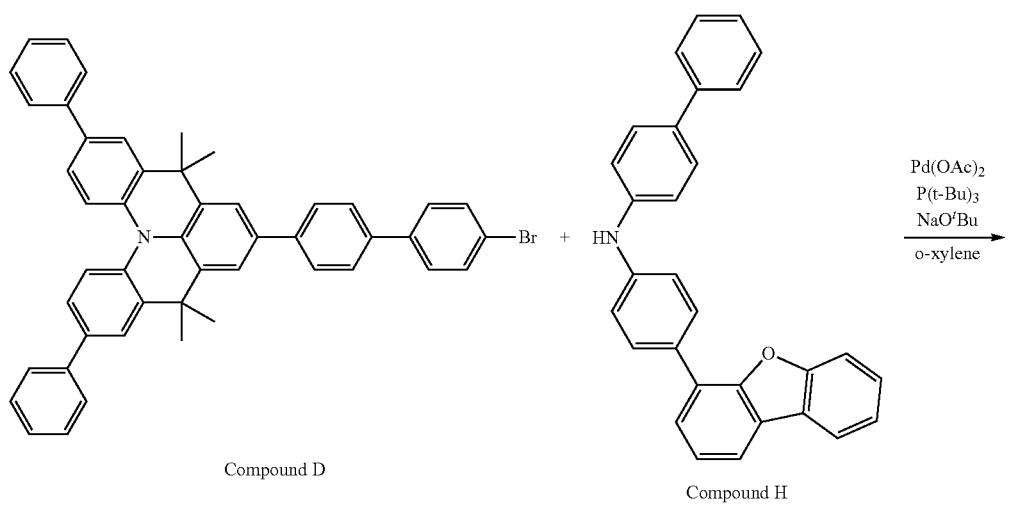

Compound D

Compound H

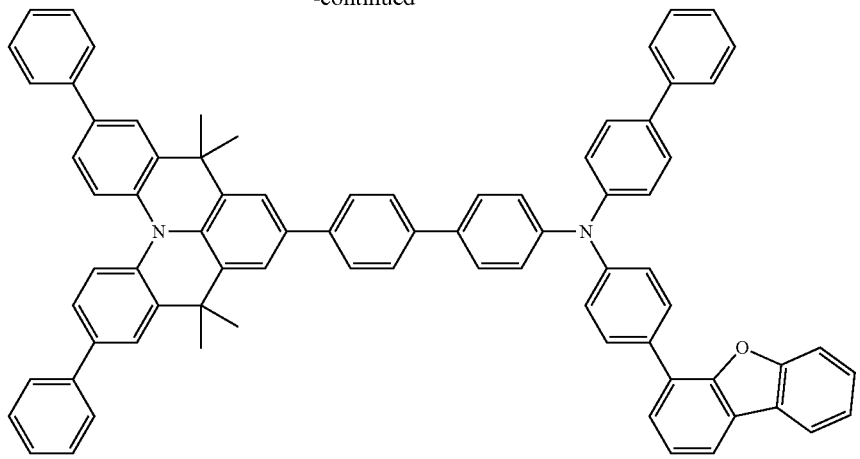

Compound 7

A 250 mL three-neck round-bottom flask was filled with nitrogen, and then Compound D (17 g, 24.0 mmol), Compound H (10.9 g, 26.4 mmol), palladium acetate (Pd(OAc)$_2$) (110 mg, 0.48 mmol), sodium tert-butoxide (2.8 g, 28.8 mmol), 170 mL of o-xylene, and a 1M toluene solution (1.0 ml, 1.0 mmol) of tri-tert-butylphosphine were added thereto, and the resulting mixture was heated at 130° C. for 5 hours. The mixture was cooled to room temperature and was added to 1,700 mL of methanol, and the resulting mixture was stirred, and then filtered, thereby obtaining 19.2 g of a pale brown solid Compound 7 (yield 77%).

MALDI-TOF: m/z=1038.4512 (C$_{78}$H$_{58}$N$_2$O=1038.45)

Example 8

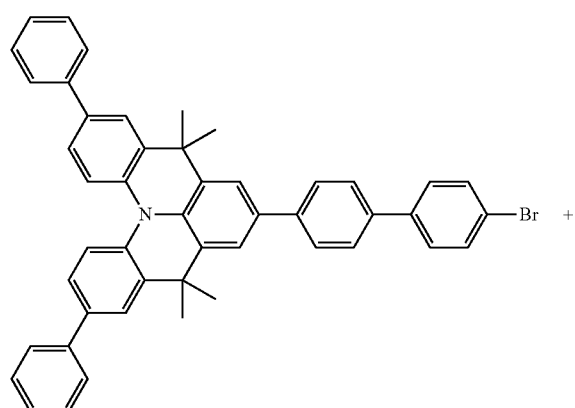

Compound D

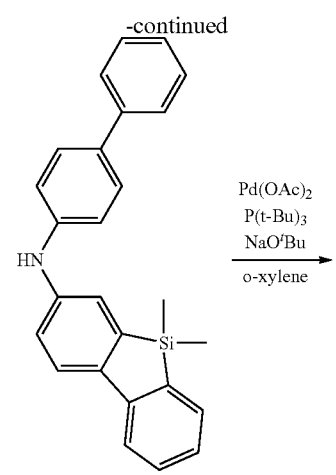

Compound I

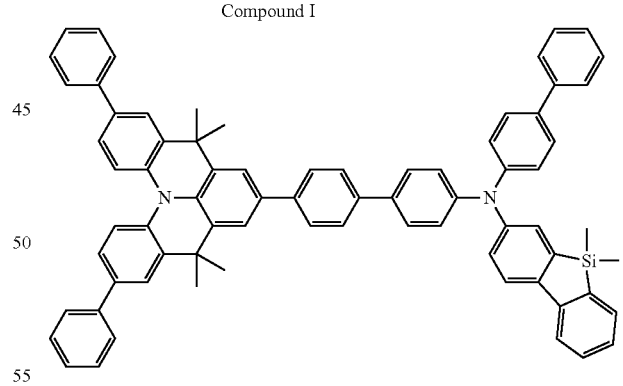

Compound 8

A 250 mL three-neck round-bottom flask was filled with nitrogen, and then Compound D (14.0 g, 19.8 mmol), Compound I (8.2 g, 21.7 mmol), palladium acetate (Pd(OAc)$_2$) (90 mg, 0.40 mmol), sodium tert-butoxide (2.3 g, 23.7 mmol), 140 mL of o-xylene, and a 1M toluene solution (0.8 ml, 0.8 mmol) of tri-tert-butylphosphine were added thereto, and the resulting mixture was heated at 130° C. for 3 hours. The mixture was cooled to room temperature and was added to 1,400 mL of methanol, and the resulting mixture was stirred, and then filtered, thereby obtaining 16.5 g of a white solid Compound 8 (yield 83%).

MALDI-TOF: m/z=1004.4526 ($C_{74}H_{60}N_2Si$=1004.45)

Example 9

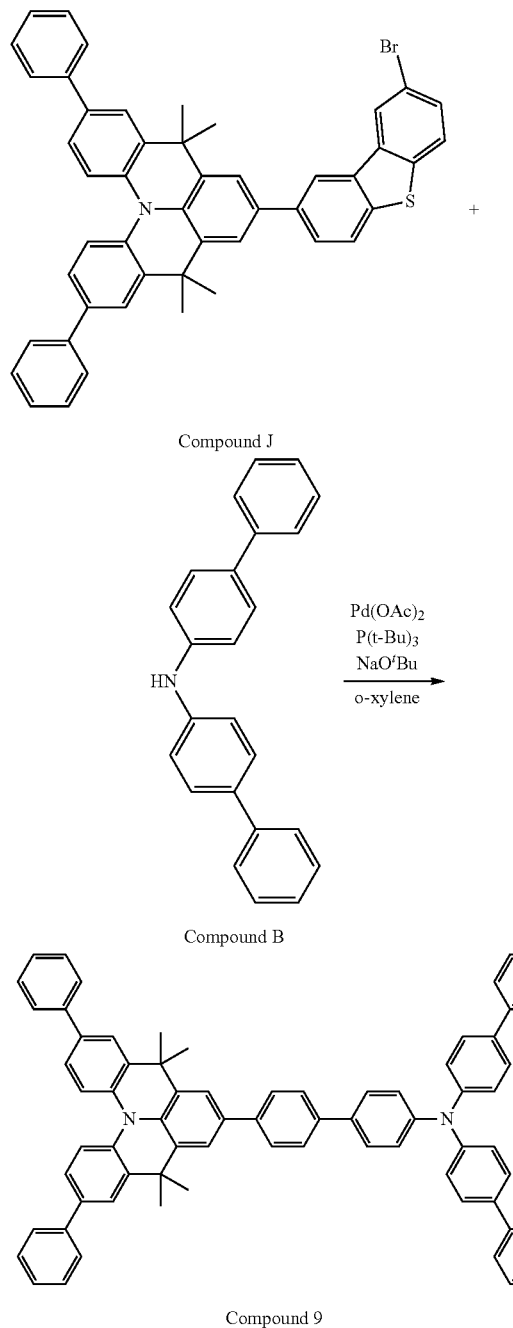

Compound J

Compound B

Compound 9 added to 1,600 mL of methanol, and the resulting mixture was stirred, and then filtered, thereby obtaining 16.8 g of a solid Compound 9 (yield 79%).

MALDI-TOF: m/z=978.4008 ($C_{72}H_{54}N_2S$=978.4)

Example 10

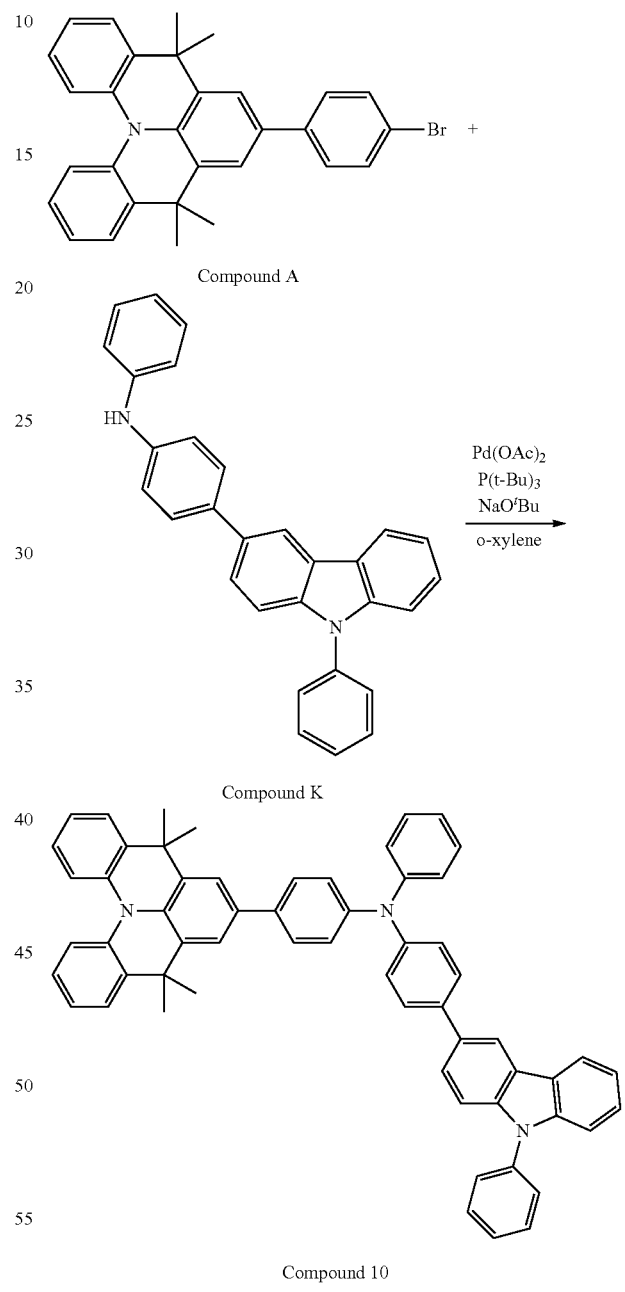

Compound A

Compound K

Compound 10

A 250 mL three-neck round-bottom flask was filled with nitrogen, and then Compound J (16 g, 21.7 mmol), Compound B (7.7 g, 23.8 mmol), palladium acetate (Pd(OAc)$_2$) (100 mg, 0.43 mmol), sodium tert-butoxide (2.5 g, 26.0 mmol), 160 mL of o-xylene, and a 1M toluene solution (0.9 ml, 0.9 mmol) of tri-tert-butylphosphine were added thereto, and the resulting mixture was heated at 130° C. for 5 hours. The mixture was cooled to normal temperature and was A 250 mL three-neck round-bottom flask was filled with nitrogen, and then Compound A (20 g, 41.6 mmol), Compound K (18.8 g, 45.8 mmol), palladium acetate (Pd(OAc)$_2$) (190 mg, 0.83 mmol), sodium tert-butoxide (4.8 g, 50.0 mmol), 200 mL of o-xylene, and a 1M toluene solution (1.7 ml, 1.7 mmol) of tri-tert-butylphosphine were added thereto, and the resulting mixture was heated at 130° C. for 6 hours. The mixture was cooled to room temperature and was added to 2,000 mL of methanol, and the resulting mixture was stirred, and then filtered, thereby obtaining 25 g of a grey solid Compound 10 (yield 74%).

MALDI-TOF: m/z=809.3802 ($C_{60}H_{47}N_3$=809.38)

Comparative Examples 1 to 3

Compounds having the structures of the following Formulae a, b, and c were commercially purchased or prepared and were used as Comparative Examples 1 to 3, respectively.

[Formula a]

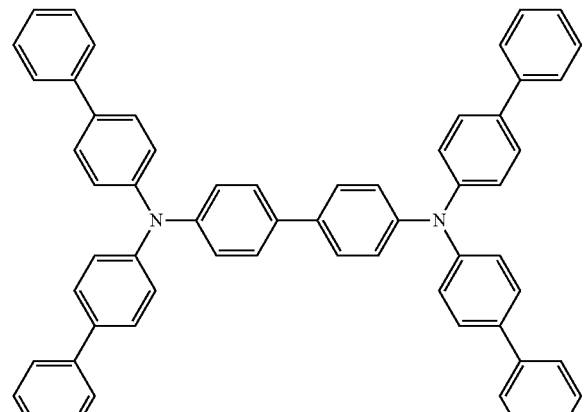

[Formula b]

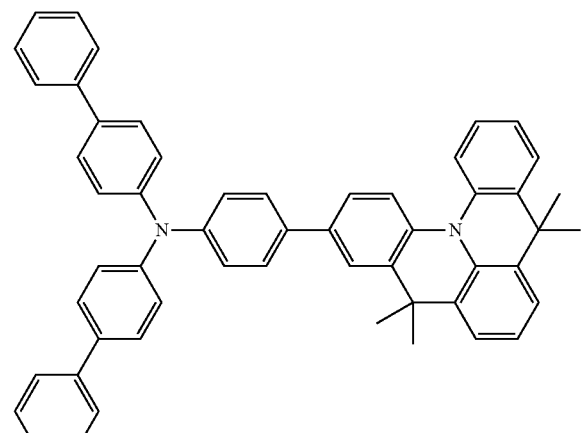

[Formula c]

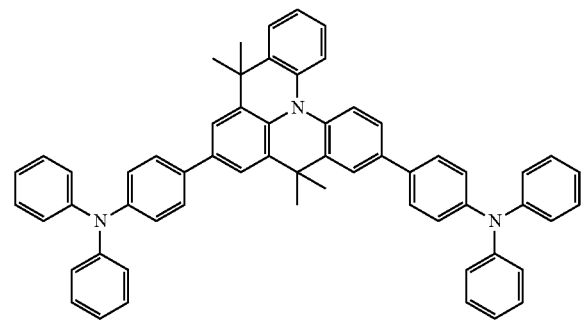

Manufacture of Light-Emitting Elements A-1 to A-10

The compound according to Example 1 as a host material was deposited at a rate of 1 Å/sec, and simultaneously, a P-type dopant (HAT-CN) represented by the following Formula 15 was co-evaporated at a ratio of about 5 parts by weight based on 100 parts by weight of the host material, on a first electrode formed of indium tin oxide (ITO), thereby forming a first layer having a thickness of 100 Å. The compound according to Example 1 was deposited to have a thickness of 300 Å on the first layer, thereby forming a second layer.

mCBP represented by the following Formula 16 and Ir(ppy)$_3$ represented by the following Formula 17 were co-deposited at a weight ratio of 100:9 on the second layer, thereby forming a layer having a thickness of about 300 Å, and mCBP was deposited again to have a thickness of about 50 Å on the light-emitting layer, thereby forming a blocking layer.

And then, Bphen represented by the following Formula 18 and Alq3 represented by the following Formula 19 were co-deposited at a weight ratio of 50:50 on the blocking layer, thereby forming an electron transporting layer having a thickness of about 400 Å. Subsequently, an electron injecting layer having a thickness of about 10 Å was formed on the electron transporting layer by using Liq represented by the following Formula 20.

A second electrode using an aluminum thin film having a thickness of 1,000 Å was formed on the electron injecting layer.

[Formula 15]

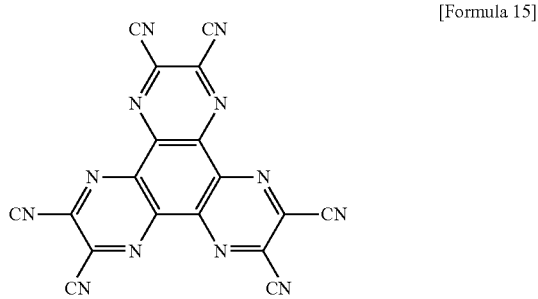

[Formula 16]

[Formula 17]

[Formula 18]

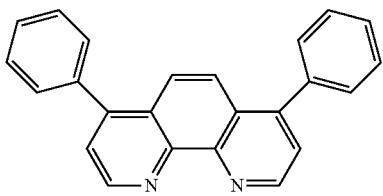

[Formula 19]

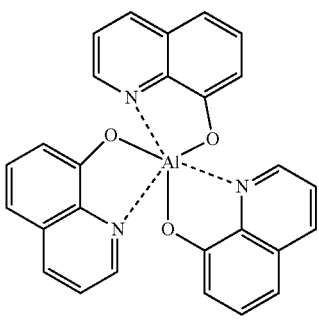

[Formula 20]

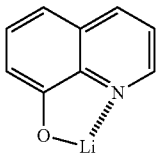

Light-Emitting Element A-1 including the compound according to Example 1 of the present invention was manufactured by the above method.

In addition, Light-Emitting Element A-2 to Light-Emitting Element A-10 were manufactured through a process which is substantially the same as the process of manufacturing Light-Emitting Element A-1, except that a hole transporting layer was formed by using each of the compounds according to Examples 2 to 10 as a host material of the first layer and the second layer.

Manufacture of Comparative Elements 1 to 3

Comparative Elements 1 to 3 were manufactured through a process which is substantially the same as the process of manufacturing Light-Emitting Element A-1, except that a hole transporting layer was formed by using each of the compounds according to Comparative Examples 1 to 3 as a host material of the first layer and the second layer.

Evaluation-1 of Power Efficiency and Lifespan of Light-Emitting Element

For each of Light-Emitting Elements A-1 to A-10 and Comparative Elements 1 to 3, a sealant for UV curing was dispensed at the edge of a cover glass, to which a moisture absorbent (Getter) was attached, in a glove box under a nitrogen atmosphere, and then each of the light-emitting elements and the comparative elements was cohered to the cover glass, and the sealant was cured by irradiating UV light thereon. For each of Light-Emitting Elements A-1 to A-10 and Comparative Elements 1 to 3 thus prepared above, the consumption efficiency was measured based on the value when the brightness was 500 cd/m². The result is shown in Table 5.

Further, the lifespan of each of Light-Emitting Elements A-1 to A-10 and Comparative Elements 1 to 3 was measured by using a lifetime measurement device provided in a measurement oven which was maintained constantly at a temperature of about 85° C. The result is shown in Table 5.

In Table 5, the unit of the result of measuring the power efficiency is lm/W. In addition, in Table 5, $T_{75}$ means a time for brightness of the light-emitting element to become 75% as compared to the initial brightness, when the initial brightness of the light-emitting element is 1,000 cd/m².

TABLE 5

| Element No. | Power efficiency [lm/W] | Lifespan ($T_{75}$@85° C. [hr]) |
|---|---|---|
| Light-Emitting Element A-1 | 20.7 | 419 |
| Light-Emitting Element A-2 | 28.5 | 603 |
| Light-Emitting Element A-3 | 26.7 | 624 |
| Light-Emitting Element A-4 | 29.5 | 579 |
| Light-Emitting Element A-5 | 24.6 | 500 |
| Light-Emitting Element A-6 | 21.1 | 426 |
| Light-Emitting Element A-7 | 20.8 | 430 |
| Light-Emitting Element A-8 | 16.3 | 357 |
| Light-Emitting Element A-9 | 13.5 | 301 |
| Light-Emitting Element A-10 | 17.3 | 385 |
| Comparative Element 1 | 9.2 | 227 |
| Comparative Element 2 | 10.8 | 224 |
| Comparative Element 3 | 8.8 | 218 |

Referring to Table 5, it can be seen that the power efficiency of each of the light-emitting elements manufactured by using the compounds according to Examples 1 to 10 of the present invention is at least 13.5 lm/W or more, and as compared to the power efficiency of 10.8 lm/W or less of Comparative Elements 1 to 3, the power efficiency of the light-emitting elements including the compound according to the present invention is better than those of Comparative Elements 1 to 3.

Furthermore, it can be seen that the lifespan of each of the light-emitting elements manufactured by using the compounds according to Examples 1 to 10 of the present invention is at least 301 hours, and the lifespan of each of Light-Emitting Elements A-2 and A-3 exceeds about 600 hours. In contrast, it can be seen that as compared to about 227 hours or less of the lifespan of Comparative Elements 1 to 3, the lifespan of the light-emitting elements including the compounds according to the present invention is better than those of Comparative Elements 1 to 3.

Further, considering that the evaluation of lifespan characteristics of the light-emitting element was performed under the acceleration condition (harsh condition), through the fact that the lifespan characteristics of the light-emitting elements including the compounds according to Examples 1 to 10 of the present invention are better than those of Comparative Elements 1 to 3, it can be seen that the heat resistance of the light-emitting element manufactured by using the compound according to the present invention is better than those of Comparative Elements 1 and 2.

Manufacture of Light-Emitting Elements B-1 to B-4

HAT-CN represented by Formula 15 was deposited to have a thickness of about 100 Å on a first electrode formed of indium tin oxide (ITO), thereby forming a first layer, and NPB (N,N'-diphenyl-N,N'-bis(1-naphthyl)-1,1'-biphenyl-4,4'-diamine) was formed to have a thickness of about 300 Å on the first layer, thereby forming a second layer.

The compound according to Example 2 was used to form a first blocking layer having a thickness of about 100 Å on the second layer, mCBP represented by Formula 16 and Ir(ppy)₃ represented by Formula 17 were co-deposited on the first blocking layer at a weight ratio of 100:9, thereby forming a light-emitting layer having a thickness of about 300 Å, and mCBP was deposited again to have a thickness of about 50 Å on the light-emitting layer, thereby forming a second blocking layer.

And then, Bphen represented by Formula 18 and Alq3 represented by Formula 19 were co-deposited at a weight ratio of 50:50 on the second blocking layer, thereby forming an electron transporting layer having a thickness of about 400 Å. Subsequently, an electron injecting layer having a thickness of about 10 Å was formed on the electron transporting layer by using Liq represented by Formula 20.

A second electrode was formed on the electron injecting layer by using an aluminum thin film having a thickness of 1,000 Å, thereby manufacturing Light-Emitting Element B-1 including the compound according to Example 2 of the present invention.

Light-Emitting Elements B-2, B-3, and B-4 were manufactured through a process which is substantially the same as the process of manufacturing Light-Emitting Element B-1, except that the first blocking layer was manufactured by using each of the compounds according to Examples 3, 6, and 7 of the present invention.

Manufacture of Comparative Element 4

Comparative Element 4 was manufactured through a process which is substantially the same as the process of manufacturing Light-Emitting Element B-1, except that the first blocking layer was manufactured by using the compound according to Comparative Example 2, which is represented by Formula b.

Evaluation-2 of Power Efficiency and Lifespan of Light-Emitting Element

For each of Light-Emitting Elements B-1 to B-4 and Comparative Element 4 thus prepared above, the power efficiency was measured by the method, which is substantially the same as in the experiment of measuring the power efficiency for Light-Emitting Elements A-1 to A-10, based on the value when the brightness was 500 cd/m$^2$.

Further, the lifespan of each of Light-Emitting Elements B-1 to B-4 and Comparative Element 4 was measured by the method which is substantially the same as in the experiment of evaluating the lifespan for Light-Emitting Elements A-1 to A-10 described above.

The results of the power efficiency and lifespan of each of Light-Emitting Elements B-1 to B-4 and Comparative Element 4 are shown in Table 6. In Table 6, the unit of the result of measuring the power efficiency is lm/W. In addition, in Table 6, $T_{75}$ means a time for brightness of the light-emitting element to become 75% as compared to the initial brightness, when the initial brightness of the light-emitting element is 1,000 cd/m$^2$.

TABLE 6

| Element No. | Power efficiency [lm/W] | Lifespan ($T_{75}$@85° C. [hr]) |
| --- | --- | --- |
| Light-Emitting Element B-1 | 32.4 | 655 |
| Light-Emitting Element B-2 | 28.5 | 683 |
| Light-Emitting Element B-3 | 26.7 | 567 |
| Light-Emitting Element B-4 | 24.6 | 615 |
| Comparative Element 4 | 9.3 | 199 |

Referring to Table 6, the power efficiency of Light-Emitting Element B-1 is about 32.4 lm/W, the power efficiency of Light-Emitting Element B-2 is about 28.5 lm/W, the power efficiency of Light-Emitting Element B-3 is about 26.7 lm/W, and the power efficiency of Light-Emitting Element B-4 is about 24.6 lm/W. It can be seen that the power efficiency of each of Light-Emitting Elements B-1 to B-4 manufactured by using the compounds according to the present invention is at least 24.6 lm/W or more, whereas the power efficiency of Comparative Element 4 is only about 9.3 lm/W. Accordingly, it can be seen that the power efficiency of the light-emitting element using the compound according to the present invention is better than that of Comparative Element 4.

Furthermore, it can be seen that the lifespan of each of Light-Emitting Elements B-1 to B-4 is at least about 567 hours and the lifespan of Light-Emitting Element B-2 is about 683 hours, whereas the lifespan of Comparative Element 4 is about 199 hours. Accordingly, it can be seen that the lifespan of the light-emitting element using the compound according to the present invention is longer than that of Comparative Element 4.

Further, considering that the evaluation of lifespan characteristics of the light-emitting elements and the comparative element was performed under the acceleration condition (harsh condition) of 85° C., through the fact that the lifespan characteristics of the light-emitting element including the compound according to the present invention are better than those of Comparative Element 4, it can be seen that the heat resistance of the light-emitting element manufactured by using the compound according to the present invention is good.

Manufacture of Light-Emitting Elements C-1 to C-4

NPB as a host material was deposited at a rate of 1 Å/sec, and simultaneously, the P-type dopant (HAT-CN) represented by Formula 15 was co-deposited at a ratio of about 5 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer. The compound according to Example 4 was used to form a first blocking layer having a thickness of about 100 Å on the second layer, mCBP represented by Formula 16 and Ir(ppy)$_3$ represented by Formula 17 were co-deposited at a weight ratio of 100:9 on the first blocking layer, thereby forming a light-emitting layer having a thickness of about 300 Å, and mCBP was deposited again to have a thickness of about 50 Å on the light-emitting layer, thereby forming a second blocking layer.

And then, Bphen represented by Formula 18 and Alq3 represented by Formula 19 were co-deposited at a weight ratio of 50:50 on the second blocking layer, thereby forming an electron transporting layer having a thickness of about 400 Å. Subsequently, an electron injecting layer having a thickness of about 10 Å was formed on the electron transporting layer by using Liq represented by Formula 20.

A second electrode was formed on the electron injecting layer by using an aluminum thin film having a thickness of 1,000 Å, thereby manufacturing Light-Emitting Element C-1 including the compound according to Example 4 of the present invention.

Light-Emitting Elements C-2, C-3, and C-4 were manufactured through a process which is substantially the same as the process of manufacturing Light-Emitting Element C-1, except that the first blocking layer was manufactured by using each of the compounds according to Examples 6, 8, and 10 of the present invention.

Manufacture of Comparative Element 5

Comparative Element 5 was manufactured through a process which is substantially the same as the process of manufacturing Light-Emitting Element C-1, except that the first blocking layer was manufactured by using the compound according to Comparative Example 2, which is represented by Formula b.

Evaluation-3 of Power Efficiency and Lifespan of Light-Emitting Element

For each of Light-Emitting Elements C-1 to C-4 and Comparative Element 5 thus prepared above, the power efficiency was measured by the method, which is substantially the same as in the experiment of measuring the power efficiency for Light-Emitting Elements A-1 to A-10, based on the value when the brightness was 500 cd/m².

Furthermore, the lifespan of each of Light-Emitting Elements C-1 to C-4 and Comparative Element 5 was measured by the method which is substantially the same as in the experiment of evaluating the lifespan for Light-Emitting Elements A-1 to A-10 described above.

The results of the power efficiency and lifespan of each of Light-Emitting Elements C-1 to C-4 and Comparative Element 5 are shown in Table 7. In Table 7, the unit of the result of measuring the power efficiency is lm/W. In addition, in Table 7, $T_{75}$ means a time for brightness of the light-emitting element to become 75% as compared to the initial brightness, when the initial brightness of the light-emitting element is 1,000 cd/m².

TABLE 7

| Element No. | Power efficiency [lm/W] | Lifespan ($T_{75}$@85° C. [hr]) |
| --- | --- | --- |
| Light-Emitting Element C-1 | 33.5 | 586 |
| Light-Emitting Element C-2 | 29.5 | 562 |
| Light-Emitting Element C-3 | 17.9 | 413 |
| Light-Emitting Element C-4 | 19.5 | 447 |
| Comparative Element 5 | 9.6 | 193 |

Referring to Table 7, it can be seen that Light-Emitting Elements C-1 to C-4 have a power efficiency of about 33.5 lm/W, about 29.5 lm/W, about 17.9 lm/W, and about 19.5 lm/W, respectively, and thus exhibit power efficiency of at least about 17.9 lm/W or more. In contrast, it can be seen that the power efficiency of Comparative Element 5 is only about 9.6 ml/W. Accordingly, it can be seen that the power efficiencies of the light-emitting elements using the compound according to the present invention are better than that of Comparative Element 5.

Further, it can be seen that the lifespan of each of Light-Emitting Elements C-1 to C-4 is about 586 hours, about 562 hours, about 413 hours, and about 447 hours, whereas the lifespan of Comparative Element 5 is only about 193 hours. Accordingly, it can be seen that the lifespans of the light-emitting elements using the compound according to the present invention are longer than that of Comparative Element 5.

In addition, considering that the evaluation of lifespan characteristics of the light-emitting element was performed under the acceleration condition (harsh condition) of 85° C., through the fact that the lifespan characteristics of the light-emitting elements including the compound according to the present invention are better than those of Comparative Element 5, it can be seen that the heat resistance of the light-emitting element manufactured by using the compound according to the present invention is good.

Manufacture of Light-Emitting Elements D-1 to D-4

The compound according to Example 1 as a host material was deposited at a rate of 1 Å/sec, and simultaneously, the P-type dopant (HAT-CN) represented by Formula 15 was co-deposited at a ratio of about 5 parts by weight based on 100 parts by weight of the host material, on a first electrode formed of indium tin oxide (ITO), thereby forming a first layer having a thickness of 100 Å. NPB was deposited to have a thickness of 300 Å on the first layer, thereby forming a second layer. mCBP represented by Formula 16 and Ir(ppy)₃ represented by Formula 17 were co-deposited at a weight ratio of 100:9 on the second layer, thereby forming a light-emitting layer having a thickness of about 300 Å, and mCBP was deposited again to have a thickness of about 50 Å on the light-emitting layer, thereby forming a blocking layer.

And then, Bphen represented by Formula 15 and Alq3 represented by Formula 19 were co-deposited at a weight ratio of 50:50 on the blocking layer, thereby forming an electron transporting layer having a thickness of about 400 Å. Subsequently, an electron injecting layer having a thickness of about 10 Å was formed on the electron transporting layer by using Liq represented by Formula 20.

A second electrode was formed on the electron injecting layer by using an aluminum thin film having a thickness of 1,000 Å, thereby manufacturing Light-Emitting Element D-1 including the compound according to Example 1 of the present invention.

Light-Emitting Elements D-2, D-3, and D-4 were manufactured through a process which is substantially the same as the process of manufacturing Light-Emitting Element D-1, except that the host material of the first layer was prepared by using each of the compounds according to Examples 4 and 5 of the present invention.

Manufacture of Comparative Element 6

Comparative Element 6 was manufactured through a process which is substantially the same as the process of manufacturing Light-Emitting Element D-1, except that the host material of the first layer was prepared by using the compound according to Comparative Example 2, which is represented by Formula b.

Evaluation-4 of Power Efficiency and Lifespan of Light-Emitting Element

For each of Light-Emitting Elements D-1 to D-4 and Comparative Element 6 thus prepared above, the power efficiency was measured by the method, which is substantially the same as in the experiment of measuring the power efficiency for Light-Emitting Elements A-1 to A-10, based on the value when the brightness was 500 cd/m².

Further, the lifespan of each of Light-Emitting Elements D-1 to D-4 and Comparative Element 6 was measured by the method which is substantially the same as in the experiment of evaluating the lifespan for Light-Emitting Elements A-1 to A-10 described above.

The results of the power efficiency and lifespan of each of Light-Emitting Elements D-1 to D-4 and Comparative Element 6 are shown in Table 8. In Table 8, the unit of the result of measuring the power efficiency is lm/W. In addition, in Table 8, $T_{75}$ means a time for brightness of the light-emitting element to become 75% as compared to the initial brightness, when the initial brightness of the light-emitting element is 1,000 cd/m².

TABLE 8

| Element No. | Power efficiency [lm/W] | Lifespan ($T_{75}$@85° C. [hr]) |
| --- | --- | --- |
| Light-Emitting Element D-1 | 21.4 | 396 |
| Light-Emitting Element D-2 | 19.6 | 372 |
| Light-Emitting Element D-3 | 21.3 | 343 |
| Light-Emitting Element D-4 | 22.7 | 430 |
| Comparative Element 6 | 11.2 | 213 |

Referring to Table 8, it can be seen that the power efficiency of each of Light-Emitting Elements D-1 to D-4 is about 21.4 lm/W, about 19.6 lm/W, about 21.3 lm/W, and about 22.7 lm/W, which are at least 19.6 lm/W or more, whereas the power efficiency of Comparative Element 6 is only about 11.2 lm/W. Accordingly, it can be seen that the power efficiencies of the light-emitting elements including the compound according to the present invention are better than that of Comparative Element 6.

Furthermore, the lifespan of each of Light-Emitting Elements D-1 to D-4 is about 396 hours, about 372 hours, about 343 hours, and about 430 hours, which are at least about 343 hours or more, whereas the lifespan of Comparative Element 6 is about 213 hours, and it can be seen that the lifespan of the light-emitting element using the compound according to the present invention is longer than that of Comparative Element 6.

Further, considering that the evaluation of lifespan characteristics of the light-emitting element was performed under the acceleration condition (harsh condition) of 85° C., through the fact that the lifespan characteristics of the light-emitting element including the compound according to the present invention are better than those of Comparative Element 6, it can be seen that the heat resistance of the light-emitting element manufactured by using the compound according to the present invention is good.

Manufacture of Light-Emitting Elements E-1 to E-4

NPB as a host material was deposited at a rate of 1 Å/sec, and simultaneously, the P-type dopant (HAT-CN) represented by Formula 15 was co-deposited at a ratio of about 5 parts by weight based on 100 parts by weight of the host material, on a first electrode formed of indium tin oxide (ITO), thereby forming a first layer having a thickness of 100 Å. The compound according to Example 2 was deposited to have a thickness of 300 Å on the first layer, thereby forming a second layer. mCBP represented by Formula 16 and Ir(ppy)$_3$ represented by Formula 17 were co-deposited at a weight ratio of 100:9 on the second layer, thereby forming a light-emitting layer having a thickness of about 300 Å, and mCBP was deposited again to have a thickness of about 50 Å on the light-emitting layer, thereby forming a blocking layer.

And then, Bphen represented by Formula 18 and Alq3 represented by Formula 19 were co-deposited at a weight ratio of 50:50 on the blocking layer, thereby forming an electron transporting layer having a thickness of about 400 Å. Subsequently, an electron injecting layer having a thickness of about 10 Å was formed on the electron transporting layer by using Liq represented by Formula 20.

A second electrode was formed on the electron injecting layer by using an aluminum thin film having a thickness of 1,000 Å, thereby manufacturing Light-Emitting Element E-1 including the compound according to Example 2 of the present invention.

Light-Emitting Elements E-2, E-3, and E-4 were manufactured through a process which is substantially the same as the process of manufacturing Light-Emitting Element E-1, except that the second layer was manufactured by using each of the compounds according to Examples 3, 4, and 7 of the present invention.

Manufacture of Comparative Element 7

Comparative Element 7 was manufactured through a process which is substantially the same as the process of manufacturing Light-Emitting Element E-1, except that the second layer was manufactured by using the compound according to Comparative Example 2, which is represented by Formula b.

Evaluation-5 of Power Efficiency and Lifespan of Light-Emitting Element

For each of Light-Emitting Elements E-1 to E-4 and Comparative Element 7 thus prepared above, the power efficiency was measured by the method, which is substantially the same as in the experiment of measuring the power efficiency for Light-Emitting Elements A-1 to A-10, based on the value when the brightness was 500 cd/m$^2$.

Further, the lifespan of each of Light-Emitting Elements E-1 to E-4 and Comparative Element 7 was measured by the method which is substantially the same as in the experiment of evaluating the lifespan for Light-Emitting Elements A-1 to A-10 described above.

The results of the power efficiency and lifespan of each of Light-Emitting Elements E-1 to E-4 and Comparative Element 7 are shown in Table 9. In Table 9, the unit of the result of measuring the power efficiency is lm/W. In addition, in Table 9, T$_{75}$ means a time for brightness of the light-emitting element to become 75% as compared to the initial brightness, when the initial brightness of the light-emitting element is 1,000 cd/m$^2$.

TABLE 9

| Element No. | Power efficiency [lm/W] | Lifespan (T$_{75}$@85° C. [hr]) |
|---|---|---|
| Light-Emitting Element E-1 | 32.8 | 701 |
| Light-Emitting Element E-2 | 30.7 | 730 |
| Light-Emitting Element E-3 | 34.0 | 658 |
| Light-Emitting Element E-4 | 28.3 | 606 |
| Comparative Element 7 | 10.7 | 206 |

Referring to Table 9, it can be seen that the power efficiency of each of Light-Emitting Elements E-1 to E-4 is about 32.8 lm/W, about 30.7 lm/W, about 34.0 lm/W, and about 28.3 lm/W, whereas the power efficiency of Comparative Element 7 is only about 10.7 lm/W. Accordingly, it can be seen that the power efficiencies of the light-emitting elements using the compound according to the present invention are better than that of Comparative Element 7.

Further, it can be seen that the lifespan of each of Light-Emitting Elements E-1 to E-4 is at least about 606 hours or more, whereas the lifespan of Comparative Element 7 is only about 206 hours. Accordingly, it can be seen that the lifespans of the light-emitting elements using the compound according to the present invention are longer than that of Comparative Element 7.

Further, considering that the evaluation of lifespan characteristics of the light-emitting element was performed under the acceleration condition (harsh condition) of 85° C., through the fact that the lifespan characteristics of the light-emitting element including the compound according to the present invention are better than those of Comparative Element 7, it can be seen that the heat resistance of the light-emitting element manufactured by using the compound according to the present invention is good.

According to those described above, it is possible to manufacture a light-emitting element, of which the power efficiency, lifespan, and thermal stability have been improved by using the novel compound according to the present invention.

What is claimed is:

1. A compound represented by the following Formula 1:

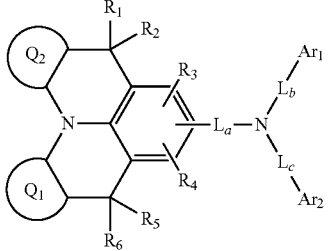

[Formula 1]

in Formula 1, $L_a$ is an arylene group having 6 to 60 carbon atoms or a heteroarylene group having 2 to 60 carbon atoms, $L_b$ and $L_c$ each independently represent a single bond $Ar_1$ and $Ar_2$ each independently represent *-$A_1$-$A_2$-$A_3$-$A_4$, $A_1$, $A_2$, and $A_3$ each independently represent a single bond, an arylene group having 6 to 60 carbon atoms, or a heteroarylene group having 2 to 60 carbon atoms, and $A_4$ represents an aryl group having 6 to 60 carbon atoms, a heteroaryl group having 2 to 60 carbon atoms, the following Formula 2 or the following Formula 3;

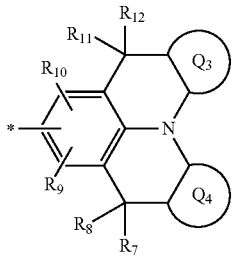

[Formula 2]

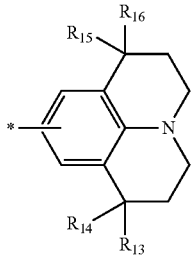

[Formula 3]

$Q_1$, $Q_2$, $Q_3$, and $Q_4$ each independently represent an aryl group having 6 to 60 carbon atoms, which is unsubstituted or substituted with one or more selected from the group consisting of an alkyl group having 1 to 12 carbon atoms, an alkoxy group having 1 to 12 carbon atoms, an aryl group having 6 to 30 carbon atoms, a heteroaryl group having 2 to 30 carbon atoms, a cycloalkyl group having 3 to 30 carbon atoms, a heterocycloalkyl group having 2 to 30 carbon atoms, an adamantyl group, a bicycloalkyl group having 7 to 30 carbon atoms, or an alkenyl group having 2 to 12 carbon atoms, $R_1$, $R_2$, $R_5$, $R_6$, $R_7$, $R_8$, $R_{11}$, $R_{12}$, $R_{13}$, $R_{14}$, $R_{15}$, and $R_{16}$ each independently represents a hydrogen or an alkyl group having 1 to 6 carbon atoms, $R_3$, $R_4$, $R_9$, $R_{10}$ each independently represent hydrogen, and one or more hydrogen atoms of $Q_1$, $Q_2$, $L_a$, $L_b$, $L_c$, $Ar_1$, and $Ar_2$ of Formula 1 are each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

2. The compound of claim 1, wherein the compound represented by Formula 1 is represented by the following Formula 4;

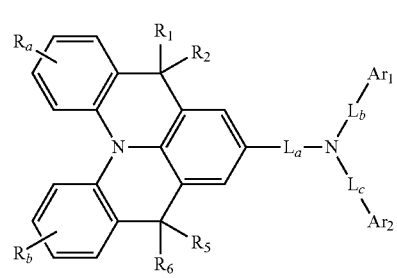

[Formula 4]

in Formula 4, $L_a$ is an arylene group having 6 to 60 carbon atoms or a heteroarylene group having 2 to 60 carbon atoms, $L_b$ and $L_c$ each independently represent $Ar_1$ and $Ar_2$ each independently represent *-$A_1$-$A_2$-$A_3$-$A_4$, $A_1$, $A_2$, and $A_3$ each independently represent a single bond, an arylene group having 6 to 60 carbon atoms, or a heteroarylene group having 2 to 60 carbon atoms, $A_4$ represents an aryl group having 6 to 60 carbon atoms, a heteroaryl group having 2 to 60 carbon atoms, the following Formula 5 or the following Formula 6;

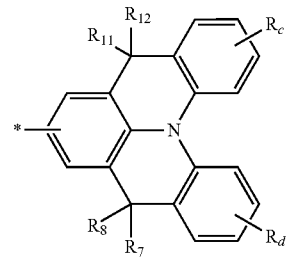

[Formula 5]

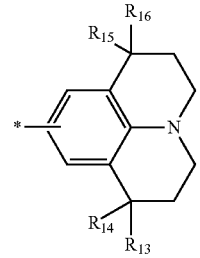

[Formula 6]

$R_1$, $R_2$, $R_5$, $R_6$, $R_7$, $R_8$, $R_{11}$, $R_{12}$, $R_{13}$, $R_{14}$, $R_{15}$, and $R_{16}$ each independently represents a hydrogen or an alkyl group having 1 to 6 carbon atoms, $R_a$, $R_b$, $R_c$, and $R_d$ each independently represent hydrogen, and hydrogen atoms of $R_a$, $R_b$, $L_a$, $L_b$, $L_c$, $Ar_1$, and $Ar_2$ of Formula 4 are each independently unsubstituted or substituted with one selected from the group consisting of an alkyl group having 1 to 6 carbon atoms, an alkenyl group having 1 to 6 carbon atoms, an alkoxy group having 1 to 6 carbon atoms, an aryl group having 6 to 20 carbon atoms, a heteroaryl group having 2 to 20 carbon atoms, an aryloxy group having 6 to 20 carbon atoms, an arylthio group having 6 to 20 carbon atoms, an alkoxycarbonyl group having 1 to 6 carbon atoms, a halogen group, a cyano group, a nitro group, a hydroxyl group, and a carboxyl group.

3. The compound of claim 2, wherein in Formula 4, $R_1$, $R_2$, $R_5$, and $R_6$ are each independently selected from hydrogen or a methyl group $Ar_1$ and $Ar_2$ are each independently selected from the following Substituents 2-1 to 2-12,

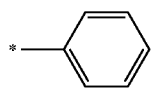

[Substituent 2-1]

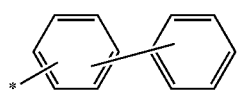

[Substituent 2-2]

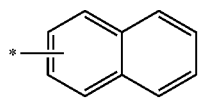

[Substituent 2-3]

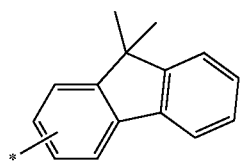

[Substituent 2-4]

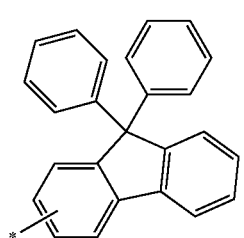

[Substituent 2-5]

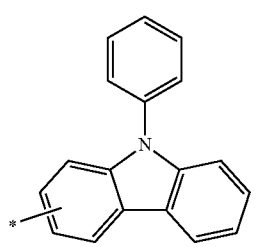

[Substituent 2-6]

-continued

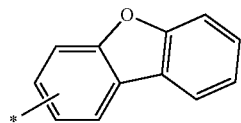

[Substituent 2-7]

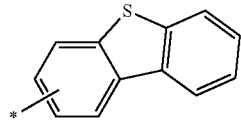

[Substituent 2-8]

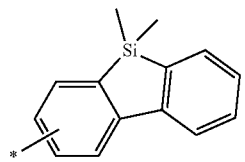

[Substituent 2-9]

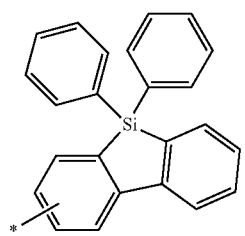

[Substituent 2-10]

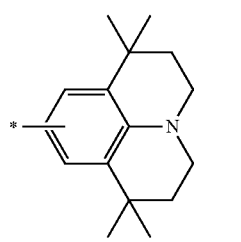

[Substituent 2-11]

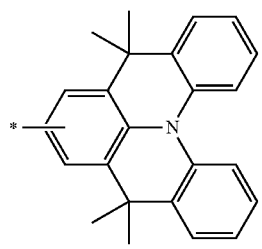

[Substituent 2-12]

$L_a$ is selected from the following Substituents 3-1 to 3-11,

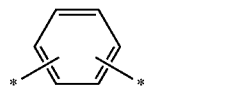

[Substituent 3-1]

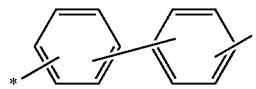

[Substituent 3-2]

-continued

[Substituent 3-3]
[Substituent 3-4]
[Substituent 3-5]
[Substituent 3-6]
[Substituent 3-7]
[Substituent 3-8]
[Substituent 3-9]
[Substituent 3-10]
[Substituent 3-11]

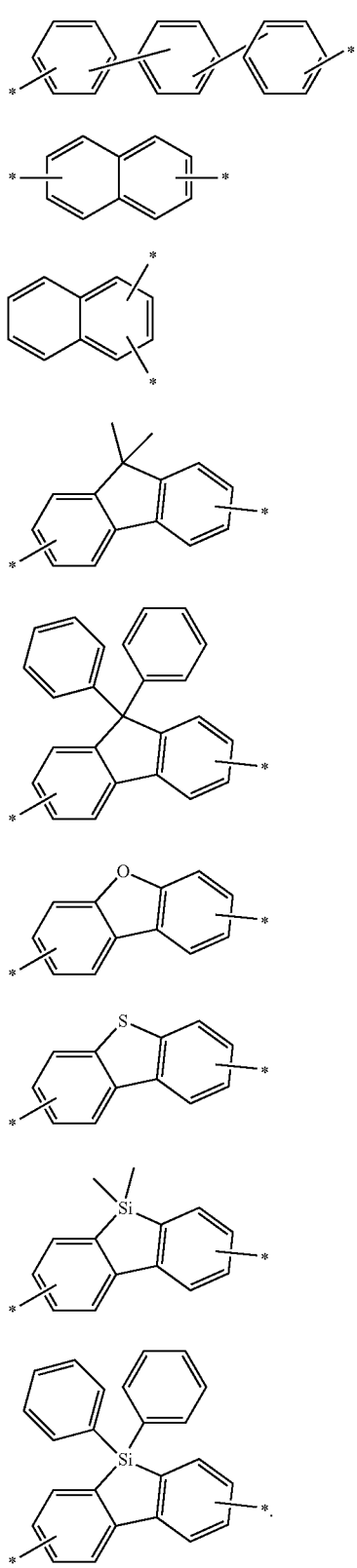

4. The compound of claim 1, wherein the compound represented by Formula 1 is represented by the following Formula 7;

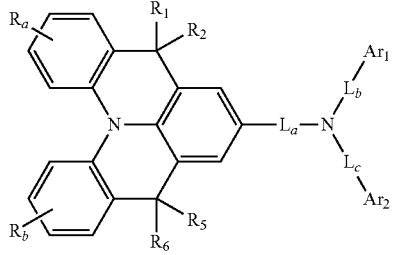

[Formula 7]

in Formula 7, $L_a$ is an arylene group having 6 to 30 carbon atoms or a heteroarylene group having 2 to 30 carbon atoms, $L_b$ and $L_c$ each independently represent a single bond $Ar_1$ and $Ar_2$ each independently represent an aryl group having 6 to 30 carbon atoms, a heteroaryl group having 2 to 30 carbon atoms, the following Formula 8 or the following Formula 9;

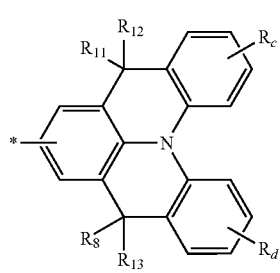

[Formula 8]

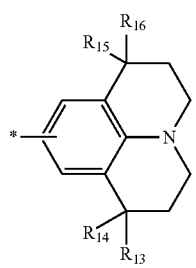

[Formula 9]

$R_1$, $R_2$, $R_5$, $R_6$, $R_7$, $R_8$, $R_{11}$, $R_{12}$, $R_{13}$, $R_{14}$, $R_{15}$, and $R_{16}$ each independently represent hydrogen or an alkyl group having 1 to 6 carbon atoms, $R_a$, $R_b$, $R_c$, and $R_d$ each independently represent hydrogen, and the hydrogen atoms of $R_a$, $R_b$, $L_a$, $L_b$, $L_c$, $Ar_1$, and $Ar_2$ of Formula 7 are each independently unsubstituted or substituted with one selected from the group consisting of an alkyl group having 1 to 6 carbon atoms, an alkoxy group having 1 to 6 carbon atoms, an aryl group having 6 to 20 carbon atoms, a heteroaryl group having 2 to 20 carbon atoms, a halogen group, a cyano group, and a nitro group.

5. A light-emitting element comprising:
a first electrode;
a second electrode;
a light-emitting layer disposed between the first electrode and the second electrode; and
a hole transporting layer disposed between the first electrode and the light-emitting layer, and including the compound of claim 1.

6. The light-emitting element of claim 5, wherein the hole transporting layer further comprises a P-type dopant.

7. The light-emitting element of claim 5, wherein the hole transporting layer comprises:
a first layer comprising the compound and a P-type dopant; and
a second layer comprising the compound.

8. An electronic device comprising the light-emitting element of claim 5.

9. The electronic device of claim 8, wherein the electronic device is a display device or a lighting device.

* * * * *